United States Patent
Ueno et al.

(10) Patent No.: US 6,194,192 B1
(45) Date of Patent: Feb. 27, 2001

(54) METHOD OF PURIFYING AND REMOVING VIRUSES

(75) Inventors: Takashi Ueno; Kimikazu Hashino; Kiyozo Asada; Ikunoshin Kato, all of Otsu (JP)

(73) Assignee: Takara Shuzo Co., Ltd., Kyoto (JP)

( * ) Notice: Subject to any disclaimer, the term of this patent is extended or adjusted under 35 U.S.C. 154(b) by 0 days.

(21) Appl. No.: 09/117,122

(22) PCT Filed: Feb. 19, 1997

(86) PCT No.: PCT/JP97/00457

§ 371 Date: Jul. 23, 1998

§ 102(e) Date: Jul. 23, 1998

(87) PCT Pub. No.: WO97/32010

PCT Pub. Date: Sep. 4, 1997

(30) Foreign Application Priority Data

Feb. 29, 1996 (JP) .................................................. 8-067514

(51) Int. Cl.[7] ..................................................... C12N 7/02
(52) U.S. Cl. ...................... 435/239; 435/235.1; 210/660; 536/118
(58) Field of Search ................................. 435/239, 235.1; 536/118; 210/660

(56) References Cited

U.S. PATENT DOCUMENTS

| | | | |
|---|---|---|---|
| 5,321,133 | * | 6/1994 | Colliec et al. ........................ 536/118 |
| 5,372,820 | * | 12/1994 | Jozefonicz et al. ............... 210/198.2 |
| 5,447,859 | * | 9/1995 | Prussak ................................. 435/239 |
| 5,502,041 | * | 3/1996 | Moen et al. ............................ 514/14 |
| 5,948,405 | * | 9/1999 | Cedro et al. .......................... 424/115 |

FOREIGN PATENT DOCUMENTS

| | | |
|---|---|---|
| 4-91027 | 3/1992 | (JP) . |
| 9634004 | 10/1996 | (WO) . |

OTHER PUBLICATIONS

Abstract in English of Japanese Patent Kokai No. 33879/87.
Abstract in English of Japanese Patent Kokai No. 30752/87.
Abstract in English of Japanese Patent Kokai No. 30753/87.
K. Tamayose et al., "A new strategy for large–scale preparation of high–titer recombinant adeno–associated virus vectors by using packaging cell lines and sulfonated cellulose", Human Gene Therapy, vol. 7, pp. 507–513, Mar. 1, 1996.
P.F O'Neil et al., "Virus Harvesting and Affinity–Based Liquid Chromatography", Bio/Technology, vol. 11, pp. 173–178, Feb. 1993.
B. Huygh4e et al., "Purification of a type 5 recombinant adenovirus encoding human p53 by column chromatography", vol. 6, pp. 1403–1416, Nov. 1995.

* cited by examiner

Primary Examiner—Leon B. Lankford, Jr.
(74) Attorney, Agent, or Firm—Wenderoth Lind & Ponack, L.L.P.

(57) ABSTRACT

The present invention offers a method for the purification or removal of virus characterized in containing a step where the virus in the virus-containing sample is adsorbed with sulfated-fucose-containing polysaccharide(s) and/or degradation product(s) thereof.

15 Claims, 23 Drawing Sheets

METHOD OF PURIFYING AND REMOVING VIRUSES

BACKGROUND OF THE INVENTION

1. Field of the Invention

The present invention relates to a simple and convenient process for treating virus which is applicable in the area of research and pharmaceuticals is also directed to a series of inventions related thereto.

2. Description of the Related Art

Many diseases in mice, cattle, birds, monkeys and human being, etc. are caused by various viruses. An example of the representative virus diseases in human being is influenza and, in recent years, acquired immune deficiency syndrome (AIDS) induced by HIV (human immunodeficiency virus) which is a kind of retrovirus that has become a social problem.

On the other hand, as a development of genetic engineering, various virus vectors for introducing exogenous gene into cells have been developed. As viral vectors for introducing genes into cells of mammals including human being, vectors derived from retrovirus, adenovirus, adeno-associated virus, etc. have been practically used already and, further, a gene therapy as a remedy for human diseases utilizing said art has now been put to practical use. In addition, a means where exogenous gene introduced in insects or insect cells utilizing baculovirus is expressed to produce desired protein in large quantities has been receiving public attention.

Vaccine is one of the means for prevention and therapy of diseases caused by virus. Attenuated virus prepared by inactivating treatment of wild type virus or virus where pathogenicity is lowered and a part of constituting components of virus (such as surface protein of virus) are used as vaccine but, usually, purified virus is used as a material for the manufacture of such a vaccine. Therefore, a process for purification of virus which is applicable in an industrial scale and is highly reliable is needed.

It is necessary that the virus which is used as a vector for introducing the gene into cell keeps a sufficient purity and/or concentration and a simple and convenient process for purification and concentration of virus has a high practical value.

Further, blood for transfusion and pharmaceutical agents such as preparations derived blood may contain virus with which the blood donor was infected and there is a possibility that administration of such an agent to patients induces a viral infection. Contamination of such virus is a very serious problem in therapy and, if at all possible, such virus is to be removed completely. For such a purpose, some treatments for inactivating virus such as by heating the blood or the preparation at 60–80° C. are conducted but heating treatment may inactivate the components which are less stable to heat contained in said pharmaceutical agent and, accordingly, there has been a demand for developing milder and more effective process for removing the virus.

An object of the present invention is to offer an effective process for purifying and removing the virus which is applicable under the various situations as mentioned above and also to offer purified virus, a substance wherefrom virus is removed, and a virus-adsorbing carrier.

SUMMARY OF THE INVENTION

The present invention will be summarized to be as follows. Thus, the first feature of the present invention relates to a process for the purification of virus and is characterized in containing a step where the virus in a virus-containing sample is adsorbed with sulfated-fucose-containing polysaccharide(s) and/or degradation product(s) thereof.

The second feature of the present invention relates to a process for the removal of virus and is characterized in containing a step where the virus in the virus-containing sample is adsorbed with sulfated-fucose-containing polysaccharide(s) and/or degradation product(s) thereof.

The third feature of the present invention relates to a purified virus which is obtained by the process of the first feature and the fourth feature relates to a product where the virus is removed which is obtained by the process of the second feature.

Further, the fifth feature of the present invention relates to a carrier for adsorption of virus containing sulfated-fucose-containing polysaccharide(s) and/or degradation product(s) thereof.

The present inventors have conducted an intensive investigation for finding a process where only virus is isolated and purified or only virus is removed from a virus-containing material by a simple means and have found that sulfated-fucose-containing polysaccharide(s) and/or degradation product(s) thereof have/has a high affinity to various viruses and that the use of an affinity carrier containing the sulfate-fucose-containing polysaccharide or a degraded product thereof is capable of purifying or removing the virus by simple operations and, moreover, in high purity and recovery rate whereupon the present invention has been achieved.

DESCRIPTION OF THE PREFERRED EMBODIMENTS

Figure 1:
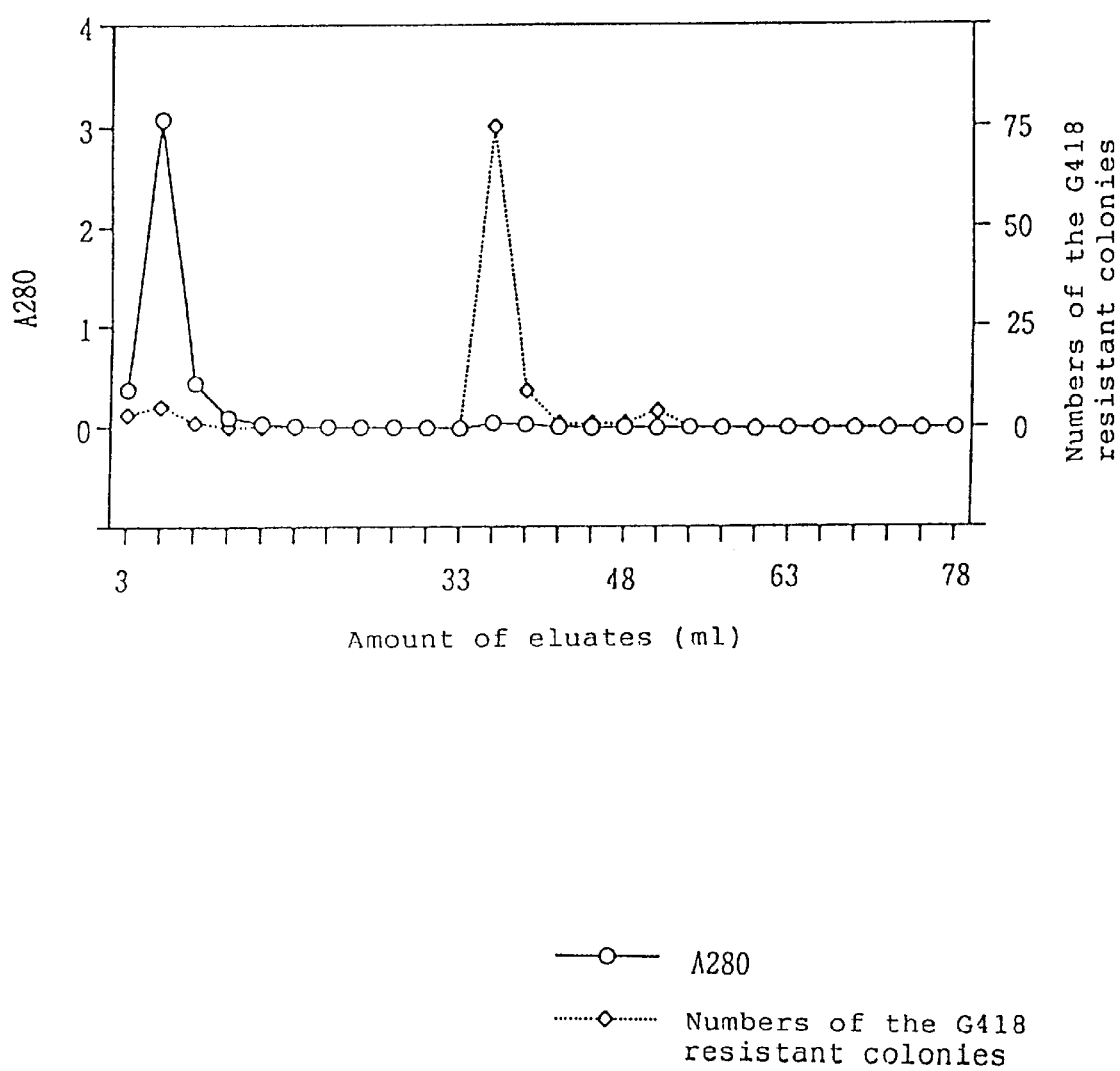
FIG. 1 shows how to purify retrovirus according to process of the present invention.

Now, the present invention will be described in greater detail.

The term "sulfated-fucose-containing polysaccharide" as used herein means a polysaccharide having sulfated fucose in its molecule without particular restriction. Examples thereof include those contained in brown algae and sea cucumber ["Tatorui Kagaku", supervised by Tokuro Soda, edited by Fujio Egami, Kyoritsu Shuppan K.K., Dec. 15, 1955, p. 319, p. 321]. Sulfated-fucose-containing polysaccharides originating in brown algae are commonly called fucoidan, fucoidin and fucan.

As the sulfated-fucose-containing polysaccharides to be used in the present invention, use can be made of sulfated-fucose-containing polysaccharide-containing materials such as brown algae and sea cucumber which have been, for example, dried as such and ground. Alternatively, use can be made of a sulfated-fucose-containing polysaccharide-containing extract obtained from a sulfated-fucose-containing polysaccharide-containing material either as such or in the purified state. The fucose-containing polysaccharide-containing extract may be prepared and purified each by a publicly known method without restriction.

The degradation products of the sulfated-fucose-containing polysaccharides to be used in the present invention are those obtained by degrading the sulfated-fucose-containing polysaccharides by enzymatic, chemical or physical methods and use can be made of publicly known enzymatic, chemical or physical methods therefor.

The sulfated-fucose-containing polysaccharides and degradation products of the sulfated-fucose-containing polysaccharides to be used in the present invention include pharmaceutically acceptable salts thereof. A sulfated-fucose-containing polysaccharide carries in its molecule sulfate groups which react with various bases to thereby form salts. These sulfated-fucose-containing polysaccharides and degradation products of the same become stable when converted into salts thereof. They are usually isolated in the form of sodium and/or potassium salts or the like. The salts of these substances can be converted into free sulfated-fucose-containing polysaccharides and free degradation products of the same by treating with a cation exchange resin such as Dowex 50W. Furthermore, these salts may be subjected to salt exchange reactions in a conventional manner to thereby convert into various desired salts, if necessary. As the salts of the sulfated-fucose-containing polysaccharides and degradation products thereof, use can be made of pharmaceutically acceptable ones, for example, salts of alkali metals such as potassium and sodium, salts of alkaline earth metals such as calcium, magnesium and barium, salts with organic bases such as pyridinium, and ammonium salts.

Examples of the brown algae containing sulfated-fucose-containing polysaccharides from which sulfated-fucose-containing polysaccharide can be prepared include those described in "Colored Illustrations of Marine Algae of Japan" [foreword: Sachio Yamada, written by Sokichi Segawa, Hoikusha Publishing Co., Ltd., 22–52 (1977)] such as *Fucus evanescens, Kjellmaniella crassifolia, Laminaria japonica* and *Undaria pinnatifida*.

As the sea cucumber containing sulfated-fucose-containing polysaccharides from which sulfated-fucose-containing polysaccharides can be prepared, use can be made of, for example, those described in Japanese Patent Laid-Open No. 91027/1992 such as *Stichopus japonicus* and *Holothuria leucospilota*.

Sulfated-fucose-containing polysaccharide is classified into a substance where uronic acid is not substantially contained and the main component of the constituting sugar is fucose, a substance where uronic acid is contained in several % and the constituting sugars include fucose and mannose, and the like. In this specification, the substance containing substantially no uronic acid will be referred to as sulfated-fucose-containing polysaccharide-F while that containing uronic acid will be referred to as sulfated-fucose-containing polysaccharide-U and their mixture will be referred to as sulfated-fucose-containing polysaccharide mixture. Those sulfated-fucose-containing polysaccharide-F, sulfated-fucose-containing polysaccharide-U, sulfated-fucose-containing polysaccharide mixture and degradation products thereof may be used in the present invention.

A powder containing sulfated-fucose-containing polysaccharides may be prepared by drying brown algae, sea cucumber and the like containing sulfated-fucose-containing polysaccharides and then ground.

An extract containing sulfated-fucose-containing polysaccharides may be prepared by extracting the powder containing sulfated-fucose-containing polysaccharides with hot water or a dilute acid.

To extract substances containing sulfated-fucose-containing polysaccharides, the extraction temperature and time may be appropriately selected depending on the purpose respectively from the ranges of 0 to 200° C. and 1 to 360 minutes. The extraction temperature and time are usually selected from the range of 10 to 150° C., preferably 50 to 130° C., and from the range of 5 to 240 minutes, preferably 10 to 180 minutes, respectively.

As a means for purifying the extract so as to elevate the sulfated-fucose-containing polysaccharide content, use can be made of, for example, fractionation of the sulfated-fucose-containing polysaccharides with the use of calcium chloride, barium acetate, etc.; fractionation of the sulfated-fucose-containing polysaccharides with the use of an acidic polysaccharide agglutinating agent such as cetylpyridinium chloride; fractionation of the sulfated-fucose-containing polysaccharides with the use of an acidic polysaccharide agglutinating agent in the presence of salts; gel filtration; and ion exchange chromatography. If necessary, purification may be effected by combining these procedures.

The sulfated-fucose-containing polysaccharides may be degraded by the methods publicly known for degrading sulfated-fucose-containing polysaccharides, for example, use of a sulfated-fucose-containing polysaccharide degrading enzyme, degradation with an acid, and ultrasonication. The degradation products may be purified in accordance with the methods described above.

Brown algae usually contain a number of sulfated-fucose-containing polysaccharides. The brown algae to be used in the present invention are not particularly restricted. For example, use can be made of those originating in Fucus evanescens, Kjellmaniella crassifolia, Laminaria japonica, Undaria pinnatifida and any other brown algae.

To produce the sulfated-fucose-containing polysaccharides, brown algae are first extracted with an aqueous solvent.

The brown algae to be extracted may be used as it is. However, it is advantageous that, prior to the preparation of the extract, the brown algae are dried, powdered, washed with 60 to 100% alcohol or acetone or soaked in an aqueous solution containing formaldehyde, acetaldehyde, glutaraldehyde, ammonia or the like, since the contamination of the sulfated-fucose-containing polysaccharides with coloring matters can be considerably relieved thereby.

When sulfated-fucose-containing polysaccharides are extracted from, for example, brown algae or the alcohol-washing residue thereof, the contamination of the extract with alginic acid can be inhibited by adding soluble calcium acetate, barium acetate, barium chloride, calcium chloride or the like, which facilitates the subsequent purification. When calcium acetate is used for the extraction, it is preferable to extract the sulfated-fucose-containing polysaccharides with a calcium acetate solution of 1 mM to 1 M at a temperature of 50 to 130° C.

When the brown algae are thick and the powder consists of large particles, it is sometimes observed that only a poor extraction efficiency can be achieved by using a calcium acetate solution of a concentration of 0.2 M or more from beginning. In such a case, it is recommended that the sulfated-fucose-containing polysaccharides are first extract with water and then calcium acetate is added to the extract followed by the elimination of the alginic acid thus precipitated.

When the sulfated-fucose-containing polysaccharides are to be extracted together with alginic acid or partly degraded products are to be obtained in the step of the extraction, the solvent and conditions for the extraction are not particularly restricted. In such a case, use can be made of water, aqueous solutions of neutral salts such as sodium chloride and magnesium chloride at various concentrations, acidic aqueous solutions of, for example, citric acid, phosphoric acid and hydrochloric acid at various concentrations, and alkaline aqueous solutions of, for example, sodium hydroxide and potassium hydroxide at various concentrations. Moreover, buffers and preservatives may be added thereto. Also, the pH value of the extract, the extraction temperature and extraction time are not particularly restricted. However, sulfated-fucose-containing polysaccharides have generally little resistant against acids and alkalis. Thus, the degradation tends to easily proceed when an acidic or alkaline solution is employed. Arbitrary degradation products can be prepared by controlling the heating temperature, heating time, pH value, etc. For example, the average molecular weight, molecular weight distribution and the like of the degradation products can be controlled by effecting gel filtration, treating with a molecular weight fractionation membrane, etc.

That is to say, the molecular weights and saccharide compositions of the sulfated-fucose-containing polysaccharide mixture, sulfated-fucose-containing polysaccharide-U, sulfated-fucose-containing polysaccharide-F and degradation products thereof to be used in the present invention vary depending on the harvest time of the sulfated-fucose-containing polysaccharide materials, the method employed for drying the materials, the method employed for storing the materials and the conditions of the extraction of the sulfated-fucose-containing polysaccharides such as heating conditions and pH value. For example, sulfated-fucose-containing polysaccharides are hydrolyzed with acids. Under alkaline conditions, on the other hand, the degradation of sulfated-fucose-containing polysaccharides proceeds as a result of the β-elimination of uronic acid. Accordingly, the molecular weights and molecular weight distributions of the sulfated-fucose-containing polysaccharide-U and the sulfated-fucose-containing polysaccharide-F described herein are each a mere example thereof. The molecular weight and molecular weight distribution can be easily varied by controlling the conditions for treating the sulfated-fucose-containing polysaccharides. For example, the sulfated-fucose-containing polysaccharide-U and the sulfated-fucose-containing polysaccharide-F of about 1,000 to 10,000 in molecular weight distribution can be prepared by heating the starting material at 100° C. for 1 hour under weakly alkaline conditions and using a molecular sieve membrane of 300 in pore size in the step of desalting. The sulfated-fucose-containing polysaccharide-U and the sulfated-fucose-containing polysaccharide-F with arbitrary molecular weight and molecular weight distribution can be prepared by appropriately selecting the treating conditions.

Alginic acid and neutral saccharides may be eliminated from the above-mentioned brown alga extract by, for example, adding an acidic polysaccharide agglutinating agent such as cetylpyridinium chloride in the presence of salts such as sodium chloride at a concentration of 0.2 to 0.6 M until no precipitate is formed any more and then collecting the precipitate. If required, the precipitate is washed with a solution of salts such as 0.2 to 0.6 M of sodium chloride and the cetylpyridinium chloride contained in the precipitate is washed away with a saturated alcoholic solution of sodium chloride to thereby give a sulfated-fucose-containing polysaccharide mixture. To eliminate coloring matters from the sulfated-fucose-containing polysaccharide mixture thus obtained, the precipitate may be dissolved and then treated with an anion exchange resin or a polysaccharide resin or subjected to ultrafiltration. When the precipitate is desalted and freeze-dried, a dry preparation can be obtained. When it is needed to efficiently produce the sulfated-fucose-containing polysaccharide-F alone, the salt concentration in the step of the agglutination with, for example, cetylpyridinium chloride is regulated not to 0.2 to 0.6 M but to, for example, 2 M. Thus the obtained precipitate contains exclusively the sulfated-fucose-containing polysaccharide-F. Also, the sulfated-fucose-containing polysaccharide-U can be separated from an aqueous solution of a sulfated-fucose-containing polysaccharide mixture.

First, one or more salts are added to the aqueous solution of the sulfated-fucose-containing polysaccharide mixture in such a manner as to give a total salt concentration of 0.6 to 2 M. As the salts to be added, use can be made of, for example, sodium chloride and calcium chloride without restriction.

Usually, the sulfated-fucose-containing polysaccharide-F can be separated from the sulfated-fucose-containing polysaccharide-U at a salt concentration of about 1.5 M (see, the illustration of FIG. 3 as will be given hereinbelow). For example, the salt concentration of the above-mentioned salt(s) is adjusted to 1.5 M and then an acidic polysaccharide agglutinating agent such as cetylpyridinium chloride is added until no precipitate is formed any more. Thus the sulfated-fucose-containing polysaccharide-F is precipitated. By removing the precipitate, the solution of the sulfated-fucose-containing polysaccharide-U can be obtained. This solution is concentrated, if necessary, and then the sulfated-fucose-containing polysaccharide-U contained therein is precipitated by adding, for example, 4 times as much ethanol thereto. Next, the cetylpyridinium chloride in the precipitate is washed away with a saturated alcoholic solution of sodium chloride to thereby give the sulfated-fucose-containing polysaccharide-U of the present invention. The sulfated-fucose-containing polysaccharide-U thus obtained may be dissolved and then subjected to ultrafiltration to thereby remove coloring matters therefrom. By desalting and freeze-drying the sulfated-fucose-containing polysaccharide-U, a dry preparation can be obtained. It is also possible to add preservatives and the like during the process.

The sulfated-fucose-containing polysaccharide-F is the sulfated-fucose-containing polysaccharides having the following physicochemical properties and can be obtained according to Referential Examples 3 to 5 that will be described later. The physicochemical properties of the sulfated-fucose-containing polysaccharide-F are as follows:

(1) constituting saccharide: substantially being free from uronic acid; and (2) substantially incapable of being degraded by the fucoidanase produced by Flavobacterium sp. SA-0082 (FERM BP-5402).

The sulfated-fucose-containing polysaccharide-U is the sulfated-fucose-containing polysaccharides having the following physicochemical properties and can be obtained according to Referential Examples 5 and 6 that will be described later. The physicochemical properties of the sulfated-fucose-containing polysaccharide-U are as follows:

(1) constituting saccharide: containing uronic acid; and (2) being degraded by the fucoidanase produced by Flavobacterium sp. SA-0082 (FERM BP-5402).

Next, the sulfated-fucose-containing polysaccharide-F to be used in the present invention and a method for producing the same will further be described in detail. The sulfated-fucose-containing polysaccharide-F to be used in the present invention may be produced in the following manner. A sulfated-fucose-containing polysaccharide mixture is treated with a degrading enzyme capable of degrading the sulfated-fucose-containing polysaccharide-U. After the completion of the enzymatic reaction, the sulfated-fucose-containing polysaccharide-U thus degraded is eliminated by ultrafiltration, etc. As the above-mentioned degrading enzyme, any enzyme may be used so long as it can selectively degrade the sulfated-fucose-containing polysaccharide-U. As a particular example thereof, citation can be made of the above-mentioned endofucoidanase produced by Flavobacterium sp. SA-0082 (FERM BP-5402) described in WO96/34004.

In the treatment with this enzyme, the substrate concentration, temperature, pH value, etc. may be appropriately selected so that the enzymatic reaction can proceed advantageously. It is usually desirable that the substrate concentration ranges from about 0.1 to 10%, the temperature ranges from about 20 to 40° C. and the pH value ranges from about 6 to 9.

It is also possible that a microorganism capable of producing a degrading enzyme having the ability to degrade the sulfated-fucose-containing polysaccharide-U is incubated in a medium to which a sulfated-fucose-containing polysaccharide mixture has been added and then the sulfated-fucose-containing polysaccharide-F is purified from the medium. The microorganism to be used therefor may be an arbitrary one, so long as it is capable of producing a degrading enzyme having the ability to degrade the sulfated-fucose-containing polysaccharide-U. As a particular example thereof, citation can be made of Flavobacterium sp. SA-0082 (FERM BP-5402) as described above and *Fucoidanobacter marinus* SI-0098 (FERM BP-5403) described in WO96/34004.

The above-mentioned Flavobacterium sp. SA-0082 has been deposited at National Institute of Bioscience and Human-Technology, Agency of Industrial Science and Technology (1–3, Higashi 1-chome, Tsukuba-shi, Ibaraki-ken 305, JAPAN) under the accession number FERM P-14872 since Mar. 29, 1995 and deposited at National Institute of Bioscience and Human-Technology as described above under the accession number FERM BP-5402 (transfer to international deposition being requested on Feb. 15, 1996).

The above-mentioned *Fucoidanobacter marinus SI*-0098 has been deposited at National Institute of Bioscience and Human-Technology, Agency of Industrial Science and Technology (1–3, Higashi 1-chome, Tsukuba-shi, Ibaraki-ken 305, JAPAN) under the accession number FERM P-14873 since Mar. 29, 1995 and deposited at National Institute of Bioscience and Human-Technology as described above under the accession number FERM BP-5403 (transfer to international deposition being requested on Feb. 15, 1996).

As mentioned above, the sulfated-fucose-containing polysaccharide-F and the sulfated-fucose-containing polysaccharide-U showed entirely different behavior to an acidic polysaccharide aggregator in the presence of one or more salt(s) having a concentration of 0.6 to 3 M.

Therefore, the sulfated-fucose-containing polysaccharide-F can be separated from an aqueous solution of a sulfated-fucose-containing polysaccharide mixture.

First, one or more salts are added to the aqueous solution of the sulfated-fucose-containing polysaccharide mixture in such a manner as to give a total salt concentration of 0.6 to 3 M. As the salts to be added, use can be made of, for example, sodium chloride and calcium chloride without restriction. After the salt concentration is adjusted as such, an acidic polysaccharide aggregator such as cetylpyridinium chloride is added until no more precipitate is formed and then the precipitate is collected to give the sulfated-fucose-containing polysaccharide-F used in the present invention.

Care must be taken, however, when the above salt concentration is made more than 2 M since the sulfated-fucose-containing polysaccharide-F of the present invention hardly forms a precipitate with cetylpyridinum chloride. For an object of separating sulfated-fucose-containing polysaccharide-F and sulfated-fucose-containing polysaccharide-U used in the present invention, said object can be usually achieved at the salt concentration of around 1.5 M.

Figure 3:
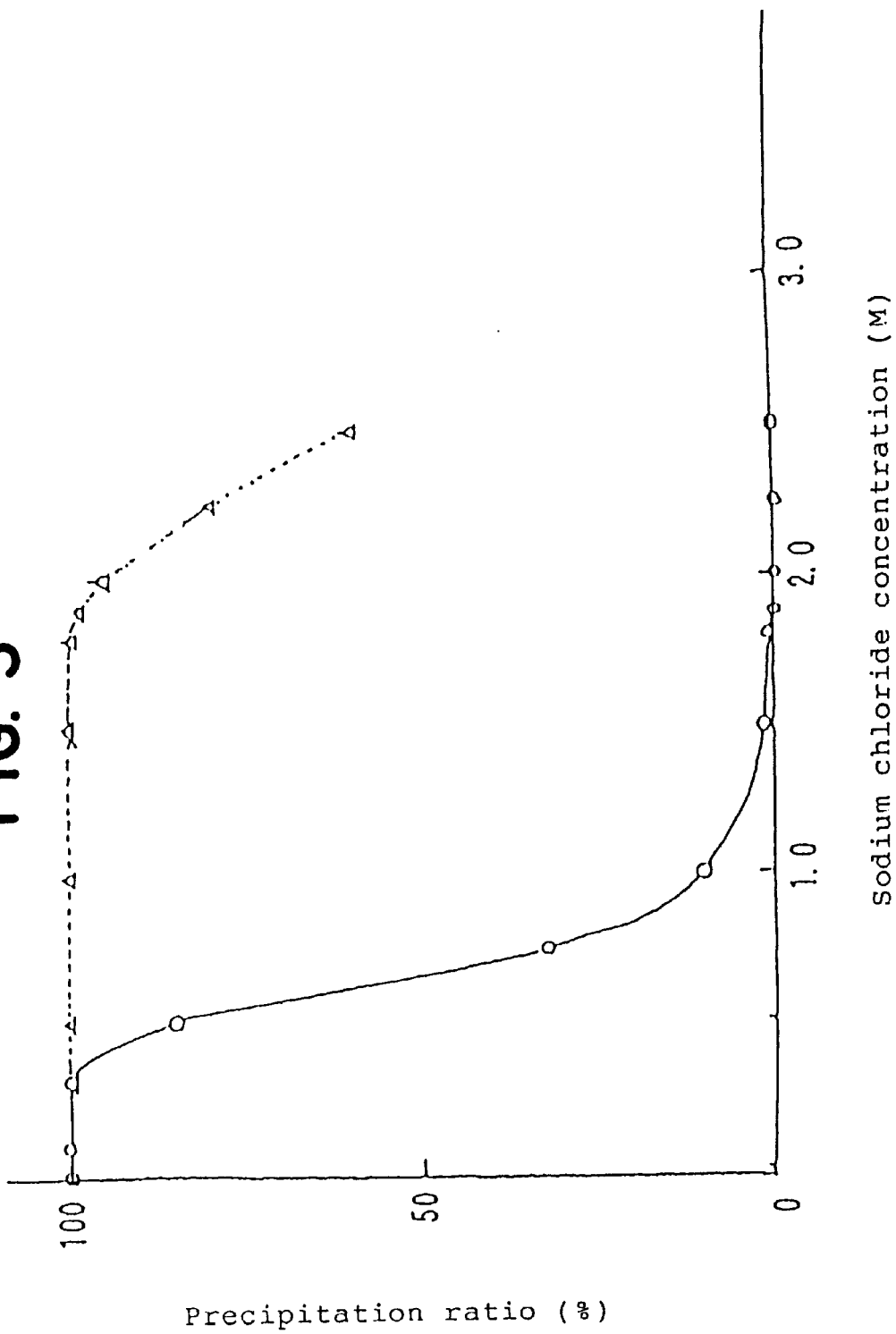
FIG. 3 shows the precipitation ratios of sulfated-fucose-containing polysaccharides.

FIG. 3 shows the precipitation ratio of this sulfated-fucose-containing polysaccharide-F and that of the sulfated-fucose-containing polysaccharide-U at various sodium chloride concentrations in the presence of cetylpyridinium chloride in excess.

In FIG. 3, the ordinate refers to the precipitation ratio (%) while the abscissa refers to the concentration (M) of sodium chloride. The dotted line and open triangle stand for the precipitation ratio of the sulfated-fucose-containing polysaccharide-F at various sodium chloride concentrations (M), while the solid line and open circle stand for the precipitation ratio of the sulfated-fucose-containing polysaccharide-U at various sodium chloride concentrations (M).

The precipitation ratios are determined at a solution temperature of 37° C. in the following manner.

The sulfated-fucose-containing polysaccharide-U and the sulfated-fucose-containing polysaccharide-F are each dissolved in water and 4 M of sodium chloride at a concentration of 2%. Then these solutions are mixed at various ratios to thereby give 125 µl portions of sulfated-fucose-containing polysaccharide-U and sulfated-fucose-containing polysaccharide-F solutions having various sodium chloride concentrations. Next, cetylpyridinium chloride was dissolved in water and 4 M of sodium chloride at a concentration of 2.5% and the obtained solutions are mixed at various ratios to thereby give 1.25% solutions of cetylpyridinium chloride with various sodium chloride concentrations.

3.2 times by volume of as much the 1.25% solution of cetylpyridinium chloride is needed to completely precipitate the sulfated-fucose-containing polysaccharide-U and sulfated-fucose-containing polysaccharide-F each dissolved in water at a concentration of 2%. To 125 µl portions of 2% solutions of the sulfated-fucose-containing polysaccharide-U and the sulfated-fucose-containing polysaccharide-F with various sodium chloride concentrations were added to 400 µl portions of cetylpyridinium chloride solutions with various sodium chloride concentrations. After thoroughly stirring and allowing to stand for 30 minutes, each mixture is centrifuged and the saccharide content of the supernatant is determined by the phenol-sulfuric acid method [Analytical Chemistry, 28, 350 (1956)] followed by the calculation of the precipitation ratio of each sulfated-fucose-containing polysaccharide at each sodium chloride concentration.

Next, this precipitate is washed, if necessary, and then the cetylpyridinium chloride in the precipitate is washed away with a saturated alcoholic solution of sodium chloride to thereby give the sulfated-fucose-containing polysaccharide-F. The sulfated-fucose-containing polysaccharide-F thus obtained may be dissolved and then subjected to ultrafiltration to thereby remove coloring matters therefrom. By desalting and freeze-drying the sulfated-fucose-containing polysaccharide-F, a dry preparation can be obtained. It is also possible to add preservatives and the like during the process.

When sulfated-fucose-containing polysaccharides are purified with the use of an anion exchange resin in the presence of a divalent cation, the amount of the sulfated-fucose-containing polysaccharides adsorbed onto the resin per unit area can be increased and thus the sulfated-fucose-containing polysaccharides can be separated more efficiently. To produce the sulfated-fucose-containing polysaccharide-F to be used in the present invention, therefore, a chemical serving as a divalent cation source is added preferably at a concentration of 1 mM or more to the sulfated-fucose-containing polysaccharide mixture. Next, the anion exchange resin is equilibrated with a solution containing the divalent cation preferably at a concentration of 1 mM or more and the above-mentioned sulfated-fucose-containing polysaccharide mixture is adsorbed thereby.

After thoroughly washing the anion exchange resin with the solution employed in the equilibration, the sulfated-fucose-containing polysaccharide-F is developed by linear gradient elution with, for example, sodium chloride. In the practice of this method, the divalent cation may be added so as to give a concentration of 1 mM or more. As the chemical serving as the divalent cation source to be used in this method, calcium salts and barium salts exhibit particularly excellent effects. However, the present invention is not restricted thereto and use can be also made of magnesium sulfate, manganese chloride, etc. therefor.

The sulfated-fucose-containing polysaccharide-F to be used in the present invention can be obtained by, for example, the method described in Referential Example 3. Next, the physicochemical properties of this sulfated-fucose-containing polysaccharide-F will be illustrated, though the sulfated-fucose-containing polysaccharide-F of the present invention is not restricted thereto.

Figure 4:
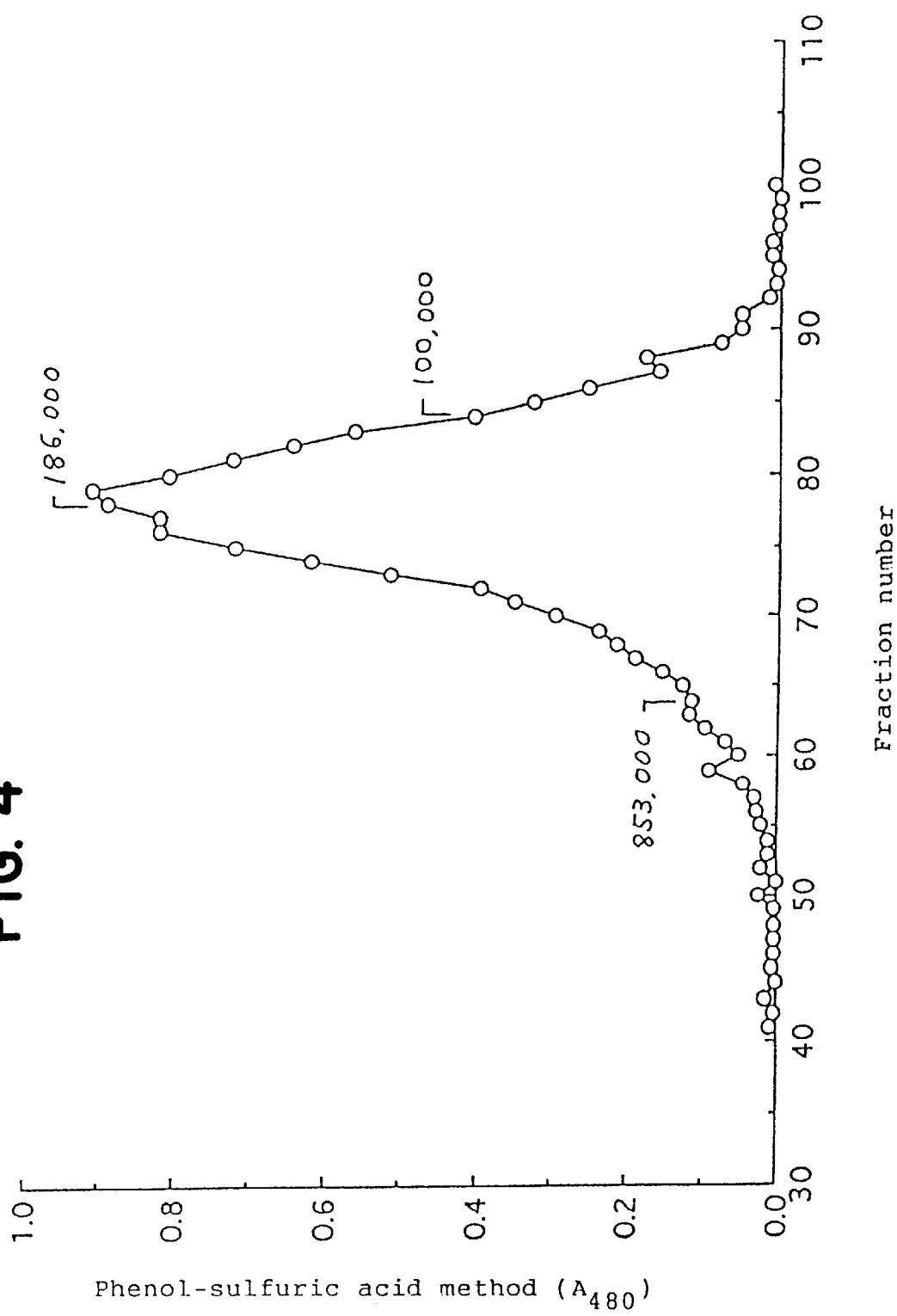
FIG. 4 shows the molecular weight distribution of the sulfated-fucose-containing polysaccharide-F determined by the gel filtration method with the use of Sephacryl S-500.

The molecular weight of the sulfated-fucose-containing polysaccharide-F thus obtained is determined by the gel filtration method with the use of Sephacryl S-500 (mfd. by Pharmacia). As a result, it shows a molecular weight distribution around about 190,000 (FIG. 4). In FIG. 4, the ordinate refers to the saccharide content in the sample determined by the phenol-sulfuric acid method which is expressed in the absorbance at 480 nm while the abscissa refers to the fraction number.

The gel filtration is performed under the following conditions:

| | |
|---|---|
| column size | 3.08 × 162.5 cm; |
| solvent | 10 mM sodium phosphate buffer (pH 6.0) containing 0.2 M of sodium chloride and 10% of ethanol; |
| flow rate | 1.5 ml/min; |
| sample concentration | 0.25%; |
| sample volume | 20 ml; |
| molecular weight standard | Shodex STANDARD P-82 (mfd. by Showa Denko, K.K.) |

Next, the components of the sulfated-fucose-containing polysaccharide-F thus obtained are analyzed.

First, the fucose content is determined in accordance with the method described in Journal of Biological Chemistry, 175, 595 (1948).

Next, the dry preparation of the sulfated-fucose-containing polysaccharide-F thus obtained is dissolved in 1 N hydrochloric acid to give a concentration of 0.5% and treated at 110° C. for 2 hours to thereby hydrolyze it into constituting monosaccharides. Subsequently, the reducing ends of the monosaccharides obtained by the hydrolysis are pyridyl-(2)-aminated (PA) by using GlycoTAG and GlycoTAG Reagent Kit (both mfd. by Takara Shuzo Co., Ltd.) and the composition ratio of the constituting monosaccharides is analyzed by HPLC. The HPLC is performed under the following conditions:

| | |
|---|---|
| apparatus | Model L-6200 (mfd. by Hitachi, Ltd.); |
| column | PALPAK Type A (4.6 mm × 150 mm); |
| eluent | 700 mM borate buffer (pH 9.0): acetonitrile = 9:1; |

| | -continued |
|---|---|
| detection | Fluorometric Detector F-1150 (mfd. by Hitachi, Ltd.), excitation wavelength: 310 nm, fluorescent wavelength: 380 nm; |
| flow rate | 0.3 ml/min; |
| column temperature | 65° C. |

Next, the content of uronic acid is determined in accordance with the method described in Analytical Biochemistry, 4, 330 (1962).

Subsequently, the content of sulfuric acid is determined in accordance with the method described in Biochemical Journal, 84, 106 (1962).

As a result, it is found out that the constituting saccharides of the sulfated-fucose-containing polysaccharide-F obtained above are fucose and galactose at a molar ratio of about 10:1. Neither uronic acid nor any other neutral saccharide is substantially contained therein. The molar ratio of fucose to sulfate is about 1:2.

Next, 16 ml of a 1% solution of the sulfated-fucose-containing polysaccharide-F, 12 ml of a 50 mM phosphate buffer (pH 8.0), 4 ml of 4 M sodium chloride and 8 ml of a 32 mU/ml solution of the endofucoidanase originating in Flavobacterium sp. SA-0082 (FERM BP-5402) described in WO96/34004 are mixed together and reacted at 25° C. for 48 hours. As a result, no degradation product is formed and the substrate is not degraded.

Figure 5:
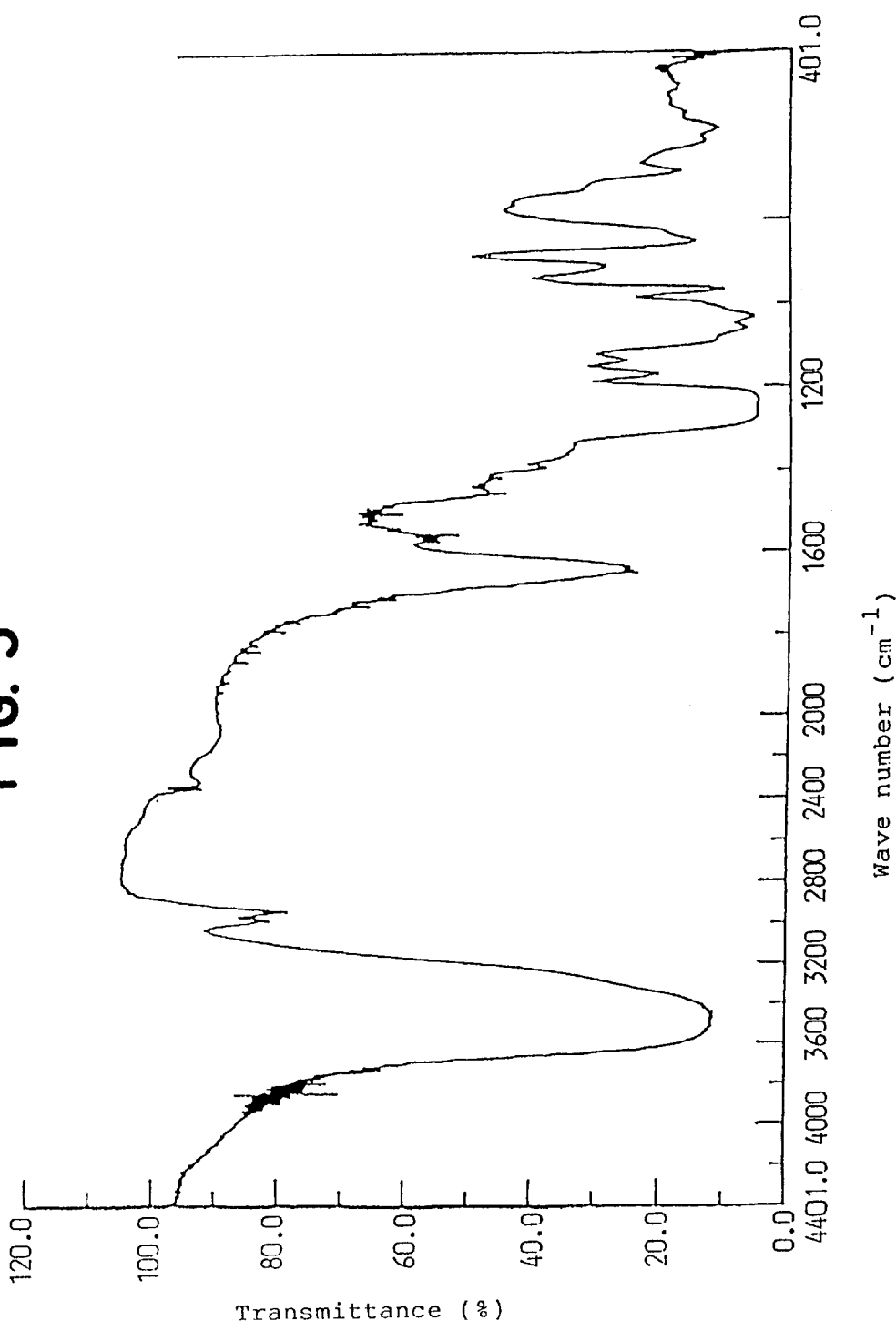
FIG. 5 is the IR spectrum of the sulfated-fucose-containing polysaccharide-F.

Then the IR spectrum of the sulfated-fucose-containing polysaccharide-F calcium salt is measured with a Fourier transform infrared spectrometer JIR-DIAMOND 20 (mfd. by JEOL Ltd.). Thus the spectrum as shown in FIG. 5 is obtained. In FIG. 5, the ordinate refers to the transmittance (%) while the abscissa refers to the wave number (cm$^{-1}$).

Next, the NMR spectrum of sodium salt of the sulfated-fucose-containing polysaccharide-F of the present invention is measured with a nuclear magnetic resonance spectrometer Model JNM-α500 (500 MHz; mfd. by JEOL Ltd.). Thus the spectrum as shown in FIG. 6 is obtained.

Figure 6:
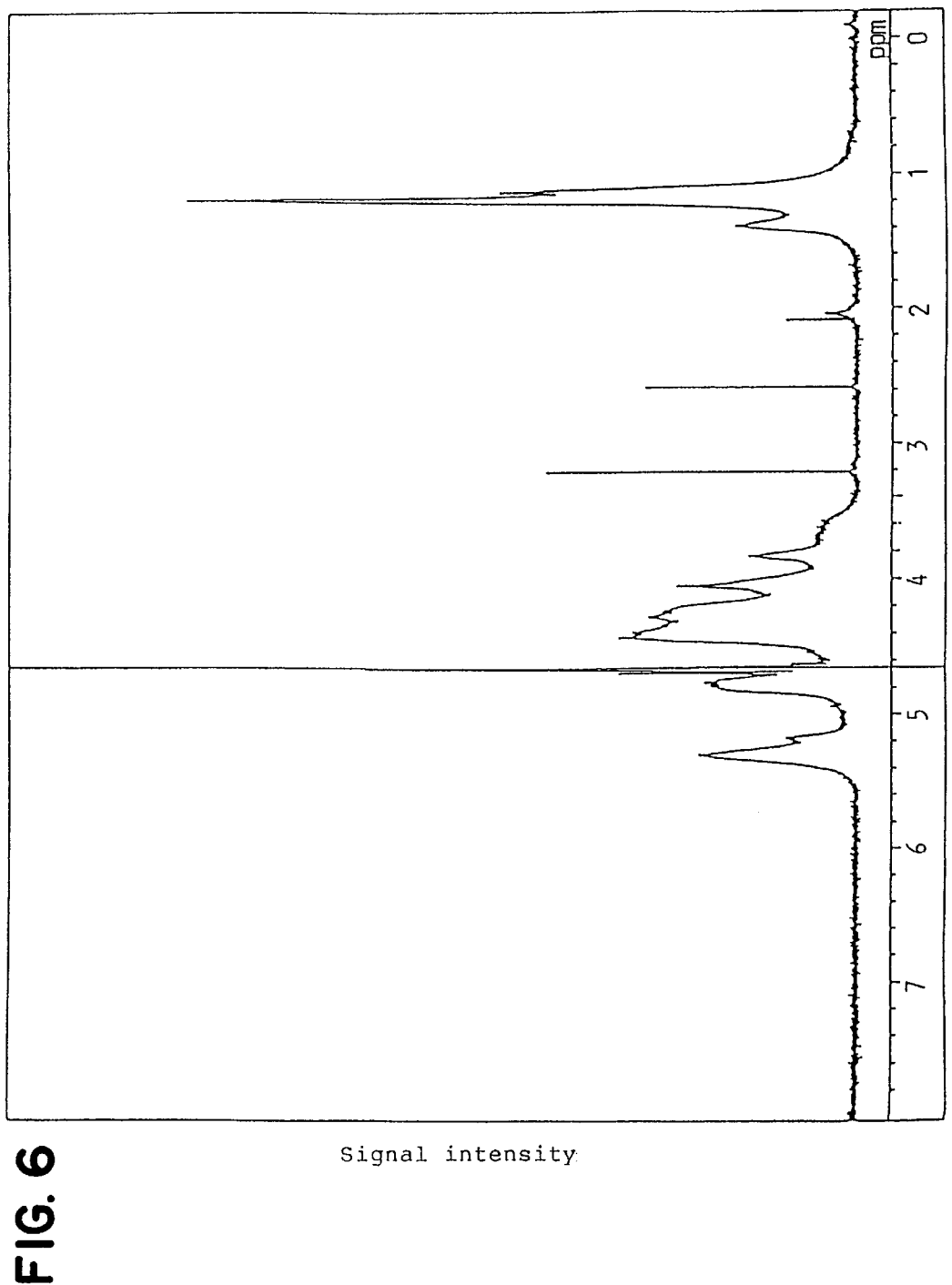
FIG. 6 is the $^1$H-NMR spectrum of the sulfated-fucose-contain polysaccharide-F.

In FIG. 6, the ordinate refers to the signal intensity while the abscissa refers to the chemical shift (ppm). The chemical shifts in $^1$H-NMR are expressed by taking the chemical shift of HOD as 4.65 ppm.

$^1$H-NMR (D$_2$O):

5.30 (H at the 1-position of fucose), 1.19 (H in CH$_3$ at the 5-position of fucose).

When measured with a high-speed, high-sensitivity polarimeter SEPA-300 (mfd. by Horiba Seisakusho), the freeze-dried product of the sulfated-fucose-containing polysaccharide-F has a specific rotation of −135°.

As such, the sulfated-fucose-containing polysaccharide-F, which has been separated from the sulfated-fucose-containing polysaccharide-U and purified, is provided. The sulfated-fucose-containing polysaccharide-F to be used in the present invention substantially contains no uronic acid as the constituting saccharide and is not degraded by the fucoidanase produced by Flavobacterium sp. SA-0082 (FERM BP-5402). The sulfated-fucose-containing polysaccharide-F is not restricted in the molecular weight, molecular weight distribution or saccharide composition. Namely, sulfated-fucose-containing polysaccharide-F having arbitrary molecular weight and molecular weight distribution may be prepared and sulfated-fucose-containing polysaccharides having definitely clarified physicochemical properties such as the saccharide composition and reducing end and an extremely high degree of sulfation can be used in the present invention.

When an enzyme which selectively degrades sulfate-fucose-containing polysaccharide-F is used, low-molecular degraded product of the sulfated-fucose-containing polysaccharide-F is offered.

With regard to the microorganism which is a source of such an enzyme, any strain may be used so far as it has an ability of producing an endo-sulfated-fucose-containing polysaccharide-F degrading enzyme. A specific example of the strains having an ability of producing an endo-sulfated-fucose-containing polysaccharide-F degrading enzyme is Alteromonas sp. SN-1009 strain which is mentioned, for example, in the Japanese Patent Application No. 204187/1996. When sulfated-fucose-containing polysaccharide-F is treated with the endo-sulfated-fucose-containing polysaccharide-F degrading enzyme derived from said strain, molecularly reduced sulfated-fucose-containing polysaccharide-F by an enzymatical means is prepared.

This strain was named as Alteromonas sp. SN-1009 and has been deposited at National Institute of Bioscience and Human-Technology, Agency of Industrial Science and Technology (1-3, Higashi 1-chome, Tsukuba-shi, Ibaraki-ken 305, JAPAN) under the accession number FERM P-15436 since Feb. 13, 1996 and deposited at National Institute of Bioscience and Human-Technology as described above under the accession number FERM BP-5747 (transfer to international deposition being requested on Nov. 15, 1996).

The nutrients to be added to the medium for incubating the strain employed in the present invention may be arbitrary ones so long as the strain can utilize them so as to produce the endo-sulfated-fucose-containing polysaccharide-F degrading enzyme. Appropriate examples of the carbon source include sulfated-fucose-containing polysaccharides, marine alga powder, alginic acid, fucose, galactose, glucose, mannitol, glycerol, saccharose and maltose, while appropriate examples of the nitrogen source include yeast extract, peptone, casamino acids, corn steep liquor, meat extract, defatted soybean, ammonium sulfate and ammonium chloride. The medium may further contain inorganic matters and metal salts such as sodium salts, phosphates, potassium salts, magnesium salts and zinc salts.

Also, this strain grows very well in seawater or artificial seawater containing the above nutrients.

In the incubation of the strain producing this endo-sulfated-fucose-containing polysaccharide-F degrading enzyme, the yield varies depending on the incubation conditions. Generally speaking, the maximum yield of the endo-sulfated-fucose-containing polysaccharide-F degrading enzyme can be achieved by incubating the strain at a temperature of from 15 to 30° C. and at a pH value of the medium of 6 to 9 under aeration/agitation for 5 to 72 hours.

Needless to say, the incubation conditions should be selected depending on the strain employed, the medium composition, etc. so that the yield of the endo-sulfated-fucose-containing polysaccharide-F degrading enzyme can attain the maximum level. The endo-sulfated-fucose-containing polysaccharide-F degrading enzyme is contained in both of the cells and the culture supernatant.

The above-mentioned Alteromonas sp. SN-1009 is incubated in an appropriate medium and the cells are harvested and disrupted by a means commonly employed for disrupting cells such as ultrasonication. Thus a cell-free extract can be obtained.

Subsequently, the extract is purified by a purification procedure commonly employed in the art to thereby give a purified enzyme preparation. For example, the purification may be effected by salting out, ion exchange chromatography, hydrophobic bond column chromatography, gel filtration or the like to thereby give the purified endo-sulfated-fucose-containing polysaccharide-F degrading enzyme free from any other fucoidanase.

The culture supernatant obtained by eliminating the cells from the above-mentioned culture medium also contains a large amount of this enzyme which can be purified by the same means as those employed for purifying the intracellular enzyme.

The chemical and physicochemical properties of the endo-sulfated-fucose-containing polysaccharide-F degrading enzyme of the present invention are as follows:

(I) function: acting on sulfated-fucose-containing polysaccharides having the following physicochemical properties, i.e., the sulfated-fucose-containing polysaccharide-F and degrading the sulfated-fucose-containing polysaccharide-F:

(a) constituting saccharide: substantially being free from uronic acid; and (b) substantially incapable of being degraded by the fucoidanase produced by Flavobacterium sp. SA-0082 (FERM BP-5402);

but not acting on sulfated-fucose-containing polysaccharides having the following physicochemical properties, i.e., the sulfated-fucose-containing polysaccharide-U:

(c) constituting saccharide: containing uronic acid; and (d) being degraded by the fucoidanase produced by Flavobacterium sp. SA-0082 (FERM BP-5402) to thereby form at least one of the compounds selected from those represented by the following formulae (I), (II) and (III):

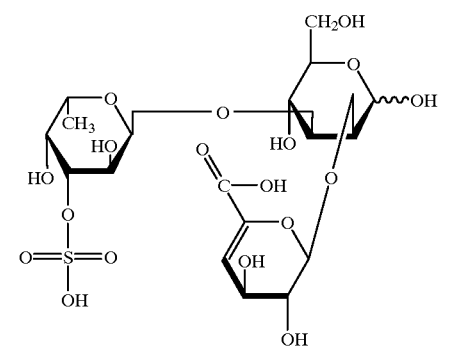

(I)

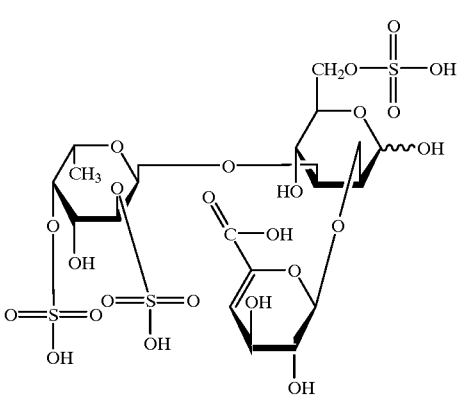

(II)

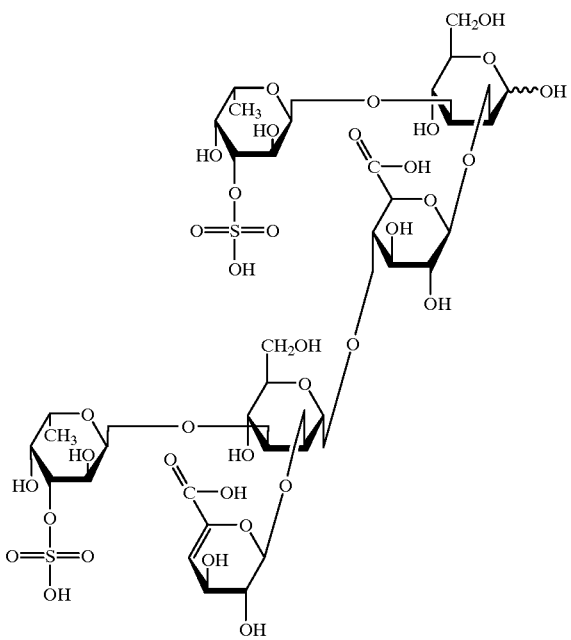

(III)

Figure 7:
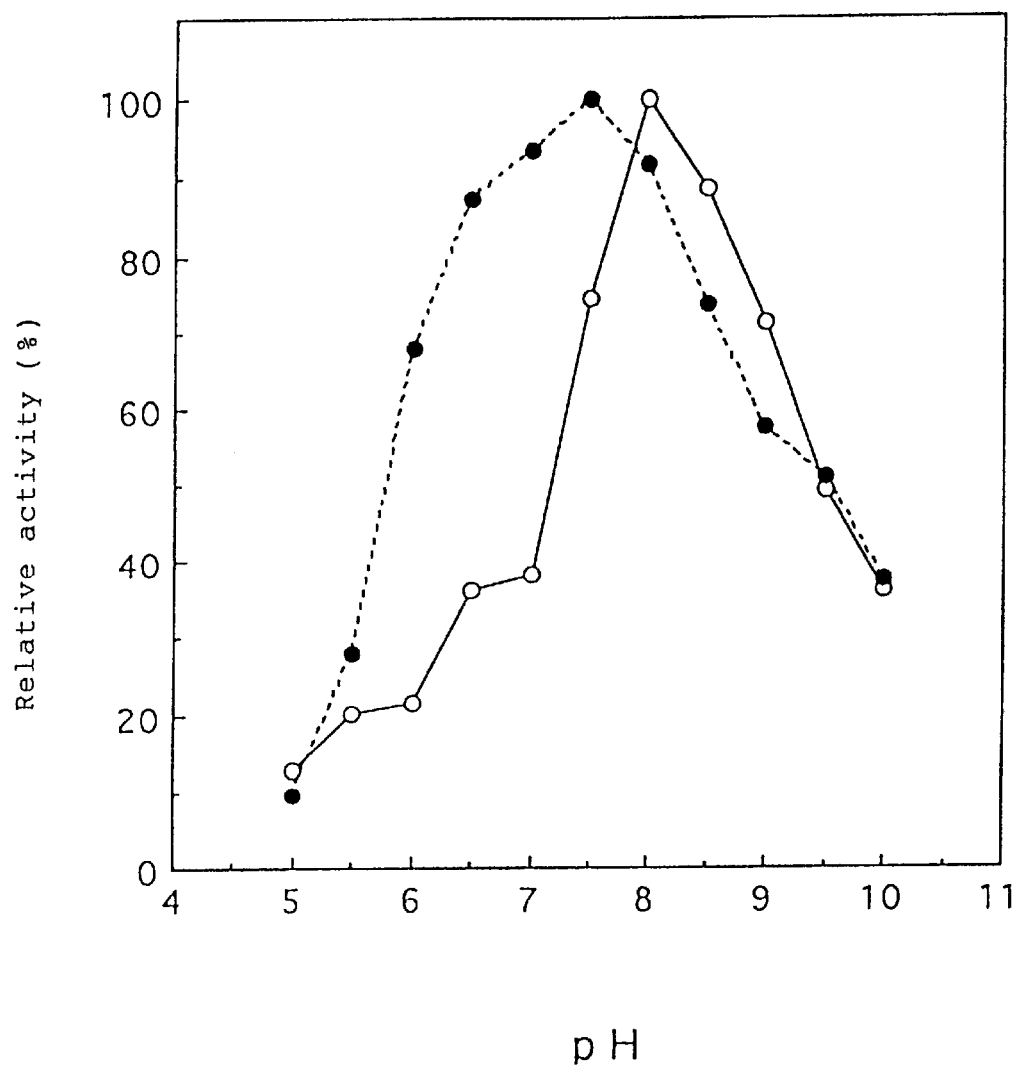
FIG. 7 is a graph which shows the relationship between the relative activity of the endo-sulfated-fucose-containing polysaccharide degrading enzyme and the pH value.

(II) optimum pH value: being from about pH 7 to 8 (FIG. 7).

FIG. 7 is a graph which shows the relationship between the relative activity of this enzyme and the pH value wherein the ordinate refers to the relative activity (%) while the abscissa refers to the pH value. The solid line is obtained by using the sulfated-fucose-containing polysaccharide-F with PA-reducing end (PA-FF) as the substrate while the dotted line is obtained by using the native sulfated-fucose-containing polysaccharide-F as the substrate.

(III) optimum temperature:being about 30 to 35° C. (FIG. 8).

Figure 8:
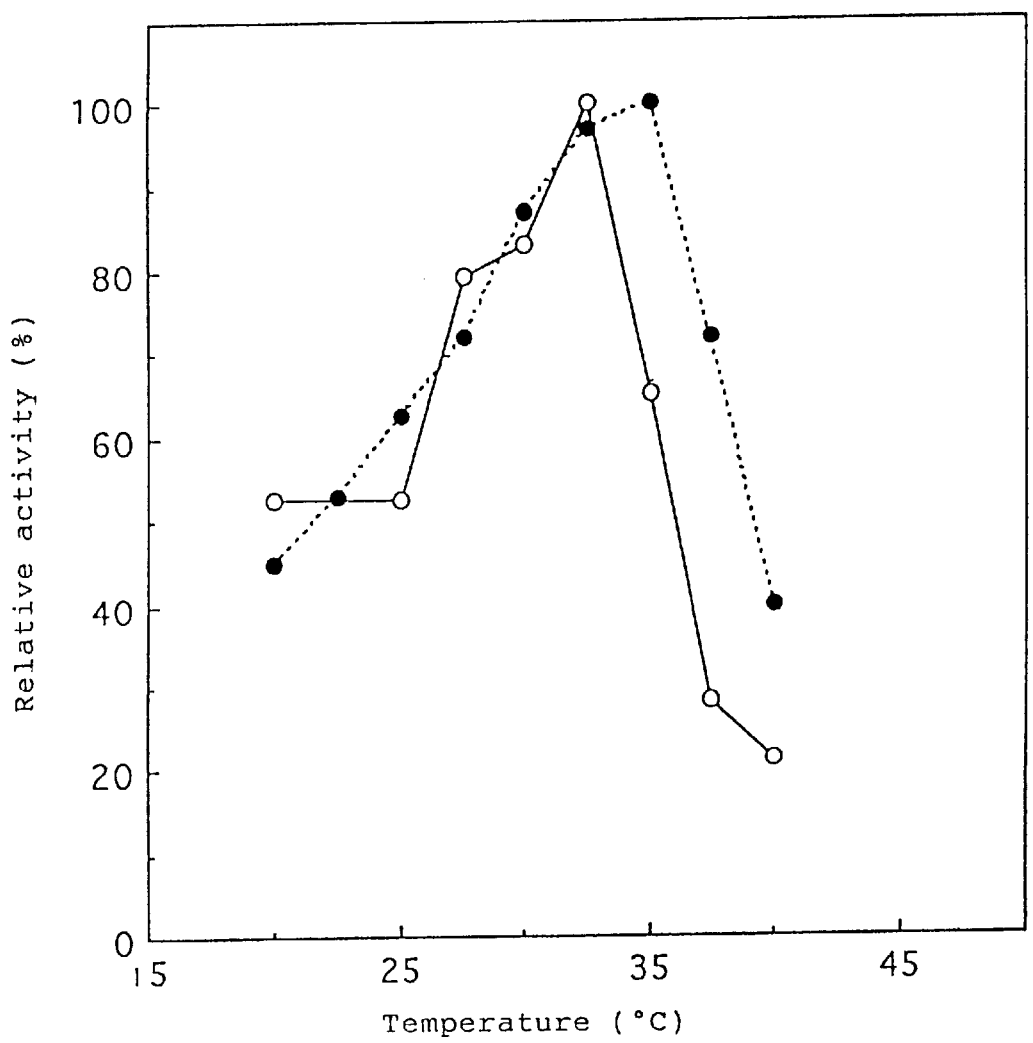
FIG. 8 is a graph which shows the relationship between the relative activity of the endo-sulfated-fucose-containing polysaccharide degrading enzyme and the temperature.

FIG. 8 is a graph which shows the relationship between the relative activity of this enzyme and the temperature wherein the ordinate refers to the relative activity (%) while the abscissa refers to the temperature (° C). The solid line is obtained by using the sulfated-fucose-containing polysaccharide-F with PA-reducing end (PA-FF) as the substrate while the dotted line is obtained by using the native sulfated-fucose-containing polysaccharide-F as the substrate.

(IV) molecular weight: the molecular weight of this enzyme determined by gel filtration with the use of Sephacryl S-200 (mfd. by Pharmacia) is about 100,000;

(V) method for measuring enzymatic activity:

The activity of the endo-sulfated-fucose-containing polysaccharide-F degrading enzyme is measured in the following manner.

First, the sulfated-fucose-containing polysaccharide-F and PA-FF serving as the substrate of the endo-sulfated-fucose-containing polysaccharide-F degrading enzyme are prepared in the following steps (1) to (3).

(1) Preparation of *Kjellmaniella crassifolia* Sulfated-fucose-containing Polysaccharide Mixture:

2 kg of dry *Kjellmaniella crassifolia* is ground with a free mill Model M-2 (mfd. by Nara Kikai Seisakusho) and treated in 4.5 times as much 80% ethanol at 80° C. for 2 hours. Then it is filtered and the residue is further subjected to the above procedures, i.e., the extraction with 80% ethanol and filtration thrice to thereby give 1,870 g of the residue after ethanol-washing. To this residue is added 36 l of water and the mixture is treated at 100° C. for 2 hours and then filtered to thereby give an extract. The salt concentration of the extract is adjusted to the same level as that of a 400 mM solution of sodium chloride. Then 5% of cetylpyridinium chloride is added thereto until no precipitate is formed any more. After centrifuging, the precipitate is repeatedly washed with 80% ethanol to thereby completely eliminate the cetylpyridinium chloride therefrom. Next, it is dissolved in 3 l of a 2 M solution of sodium chloride. After removing the insoluble matters by centrifugation, 100 ml of DEAE-Cellulofine A-800 (mfd. by Seikagaku Kogyo) equilibrated with 2 M sodium chloride is suspended therein. The suspension is stirred and then filtered to thereby remove the resin. The filtrate is fed into a 100 ml DEAE-Cellulofine A-800 column equilibrated with 2 M sodium chloride and the fraction passing therethrough is desalted and low-molecular weight matters are removed therefrom by using an ultrafiltration membrane (exclusion molecular weight of membrane: 100,000). The precipitate thus formed is eliminated by centrifugation. The supernatant is freeze-dried to thereby give 82.2 g of a purified *Kjellmaniella crassifolia* sulfated-fucose-containing polysaccharide mixture.

(2) Preparation of Sulfated-Fucose-Containing Polysaccharide-F:

6 g of the above-mentioned sulfated-fucose-containing polysaccharide mixture originating in *Kjellmaniella crassifolia* is dissolved in 600 ml of 20 mM of sodium acetate (pH 6.0) containing 0.2 M of calcium chloride. Then the solution is fed into a 3600 ml DEAE-Sepharose FF (mfd. by Pharmacia) column preliminarily equilibrated with 20 mM of sodium acetate (pH 6.0) containing 0.2 M of calcium chloride. Then the column is thoroughly washed with 20 mM of sodium acetate (pH 6.0) containing 0.2 M of calcium chloride and developed by linear gradient elution with sodium chloride of 0 to 2 M.

The sulfated-fucose-containing polysaccharide-F fractions eluted at sodium chloride concentrations of 0.75 M and above are collected and desalted by using an ultrafilter provided with an ultrafiltration membrane of exclusion molecular weight of 100,000. After freeze-drying, 3.3 g of a freeze-dried preparation of the sulfated-fucose-containing polysaccharide-F is obtained.

(3) Preparation of PA-FF:

12 mg of the above-mentioned freeze-dried preparation of the sulfated-fucose-containing polysaccharide-F is dissolved in 480 µl of water and 12 µl portions of the obtained solution are pipetted into 36 tubes. After freeze-drying, the reducing end is pyridyl-(2)-aminated (PA) by using Glyco-TAG and GlycoTAG Reagent Kit to thereby give PA-FF. The PA-FF thus obtained is dissolved in a 10 mM solution of ammonium acetate containing 15 ml of 10% methanol and subjected to gel filtration with the use of a Cellulofine GCL-300 (mfd. by Seikagaku Kogyo) column (40×900 mm). The high-molecular weight fractions are collected and desalted by thoroughly dialyzing with the use of a dialysis membrane of 3500 in pore size. Subsequently, it is concentrated to 5 ml with an evaporator to thereby give PA-FF to be used as the substrate of the endo-sulfated-fucose-containing polysaccharide-F degrading enzyme.

The quantity of PA-FF thus obtained is estimated as about 40 nmol through the comparison with the fluorescence intensity of marketed pyridyl-(2)-aminated fucose (mfd. by Takara Shuzo Co., Ltd.; excitation wavelength: 320 nm, fluorescent wavelength: 400 nm).

By using the sulfated-fucose-containing polysaccharide-F obtained by the above steps (1) and (2), the activity of the endo-sulfated-fucose-containing polysaccharide degrading enzyme is determined in the following manner.

Namely, 12 µl of a 2.5% solution of the sulfated-fucose-containing polysaccharide-F, 6 µl of a 1 M solution of calcium chloride, 12 µl of a 1 M solution of sodium chloride, 72 µl of a buffer (pH 7.5) containing 50 mM of acetic acid, imidazole and Tris hydrochloride and 18 µl of the endo-sulfated-fucose-containing polysaccharide-F degrading enzyme are mixed together and reacted at 30° C. for 3 hours. Then the reaction mixture is treated at 100° C. for 10 minutes and centrifuged. Then the degree of degradation is measured by analyzing a 100 µl portion of the reaction mixture by HPLC.

As controls, use is made of a reaction mixture prepared by the same method but substituting the endo-sulfated-fucose-containing polysaccharide-F degrading enzyme by the buffer used to prepare the endo-sulfated-fucose-containing polysaccharide-F degrading enzyme solution and another reaction mixture prepared by the same method but substituting the sulfated-fucose-containing polysaccharide-F solution by water alone. These controls are also analyzed by HPLC.

The amount of the enzyme by which the fucosyl bonds in 1 µmol of the sulfated-fucose-containing polysaccharide-F can be cleaved in one minute is taken as one U. The fucosyl bonds thus cleaved are calculated in accordance with the following equation:

| | |
|---|---|
| Activity (U/ml) = {(12 × 2.5)/(100 × MF)} × {(MF/M) − 1} × {0.12/(180 × 0.01)} (12 × 2.5)/100 | sulfated-fucose-containing polysaccharide-F (mg) added to reaction system; |
| MF | average molecular weight of substrate (sulfated-fucose-containing polysaccharide-F); |
| M | average molecular weight of reaction product; |
| (MF/M) − 1 | number of cleavages by enzyme in one molecule of sulfated-fucose-containing polysaccharide-F; |
| 180 | reaction time (min); |
| 0.01 | volume (ml) of enzyme solution; and |
| 0.12 | volume (ml) of whole reaction mixture. |

The HPLC is performed under the following conditions:

| | |
|---|---|
| apparatus | Model L-6200 (mfd. by Hitachi, Ltd.); |
| column | OHpack KB-804 (8 mm × 300 mm, mfd. by Showa Denko K.K.); |
| eluent | 25 mM imidazole buffer (pH 8) containing 5 mM of sodium azide, 25 mM of calcium chloride and 50 mM of sodium chloride; |
| detection | differential refractometric detector (Shodex RI-71, mfd. by Showa Denko K.K.); |
| flow rate | 1 ml/min; |
| column temperature | 25° C. |

To measure the average molecular weight of the reaction product, marketed pullulan with a known molecular weight (STANDARD P-82, mfd. by Showa Denko K.K.) is analyzed by HPLC under the same conditions as those described above. Then a curve showing the relationship between the molecular weight of the pullulan and the retention time on the OHpak KB-804 is prepared and employed as the standard curve for determining the molecular weight of the above-mentioned enzymatic reaction product.

By using the PA-FF obtained by the above steps (1) to (3), the activity of the endo-sulfated-fucose-containing polysaccharide-F degrading enzyme of the present invention is determined in the following manner.

Namely, 2 μl of an 8 pmol/μl solution of the PA-FF, 5 μl of a 1 M solution of calcium chloride, 10 μl of a 1 M solution of sodium chloride, 23 μl of water, 50 μl of a buffer (pH 8.2) containing 50 mM of acetic acid, imidazole and Tris hydrochloride and 10 μl of the endo-sulfated-fucose-containing polysaccharide-F degrading enzyme are mixed together and reacted at 30° C. for 3 hours. Then the reaction mixture is treated at 100° C. for 10 minutes and centrifuged. Then the degree of degradation is measured by HPLC using 80 μl of the sample thus prepared.

As controls, use is made of a reaction mixture prepared by the same method but substituting the endo-sulfated-fucose-containing polysaccharide-F degrading enzyme by the buffer used to prepare the endo-sulfated-fucose-containing polysaccharide degrading enzyme solution and another reaction mixture prepared by the same method but substituting the PA-FF solution by water alone. These controls are also analyzed by HPLC.

The amount of the enzyme by which the fucosyl bonds in 1 μmol of the sulfated-fucose-containing polysaccharide-F can be cleaved in one minute is taken as one U. The fucosyl bonds thus cleaved are calculated in accordance with the following equation:

| | |
|---|---|
| Activity (U/ml) = $16 \times 10^{-6} \times \{(MF/M) - 1\} \times \{1/(180 \times 0.01)\}$ | amount (μmol) of PA-FF added to reaction system; |
| $16 \times 10^{-6}$ | |
| MF | average molecular weight of substrate (sulfated-fucose-containing polysaccharide-F); |
| M | average molecular weight of reaction product; |
| (MF/M) − 1 | number of cleavages by enzyme in one molecule of sulfated-fucose-containing polysaccharide-F; |
| 180 | reaction time (min); and |
| 0.01 | volume (ml) of enzyme solution. |

The HPLC is performed under the following conditions:

| | |
|---|---|
| apparatus | Model L-6200 (mfd. by Hitachi, Ltd.); |
| column | OHpak SB-803 (8 min × 300 mm, mfd. by Showa Denko K.K.) |
| eluent | 200 mM sodium chloride solution containing 5 mM of sodium azide and 10% of dimethyl sulfoxide; |
| detection | Fluorometric Detector F-1150 (mfd. by Hitachi, Ltd.), excitation wavelength: 320 nm, fluorescent wavelength: 400 nm; |
| flow rate | 1 ml/min; and |
| column temperature | 50° C. |

To measure the average molecular weight of the reaction product, the reducing end of marketed pullulan with a known molecular weight (STANDARD P-82, mfd. by Showa Denko K.K.) is pyridyl-(2)-aminated (PA) by using GlycoTAG and GlycoTAG Reagent Kit to thereby give PA-pullulans of various molecular weights. These PA-pullulans with various molecular weights are then analyzed by HPLC under the same conditions as those described above. Then a curve showing the relationship between the molecular weight of the pullulan and the retention time on the OHpak SB-803 is prepared and employed as the standard curve for determining the molecular weight of the above-mentioned enzymatic reaction product.

The protein is determined by measuring the absorbance of the enzyme solution at 280 nm. Calculation is made by taking the absorbance of a 1 mg/ml protein solution as 1.0.

Next, the action mechanism of the endo-sulfated-fucose-containing polysaccharide-F degrading enzyme was clarified and the degradation products was prepared in the following manner.

(1) Degradation of Sulfated-fucose-containing Polysaccharide-F endo-sulfated-fucose-containing Polysaccharide-F Enzyme and Preparation of Degradation Product:

Purified sulfated-fucose-containing polysaccharide-F originating in *Kjellmaniella crassifolia* is treated with the endo-sulfated-fucose-containing polysaccharide-F degrading enzyme to thereby prepare the degradation products thereof.

First, the sulfated-fucose-containing polysaccharide-F degrading enzyme is produced. Namely, Alteromonas sp. SN-1009 (FERM BP-5747) is inoculated into 600 ml of a medium comprising artificial seawater (pH 8.2, mfd. by Jamarin Laboratory) containing 0.25% of glucose, 1.0% of peptone and 0.05% of yeast extract which has been sterilized (120° C., 20 minutes) and pipetted into a 2-l Erlenmeyer flask. Then the strain is incubated therein at 25° C. for 26 hours to thereby give a seed culture. Into a 30-l jar fermenter is fed 20 l of a medium comprising artificial seawater (pH 8.0) containing 1.0% of peptone, 0.02% of yeast extract, 0.2% of the above-mentioned sulfated-fucose-containing polysaccharide-F originating from *Kjellmaniella crassifolia* and 0.01% of a defoaming agent (KM70 mfd. by Shin-Etsu Chemical Co., Ltd.) and sterilized at 120° C. for 20 minutes. After cooling, the medium is inoculated with 600 ml of the above-mentioned seed culture, which is then incubated therein at 24° C. for 24 hours under aerating at a rate of 10 l/min and agitating at 250 rpm. After the completion of the incubation, the culture medium is centrifuged to thereby give the cells and the culture supernatant. The culture supernatant thus obtained is concentrated with an ultrafilter with a fractional molecular weight of 10,000 and salted out with the use of 85% ammonium sulfate. The precipitate thus formed is taken up by centrifugation and thoroughly dialyzed against a 20 mM Tris hydrochloride buffer (pH 8.2) containing artificial seawater diluted 10-fold. Thus 600 ml of a crude enzyme is obtained.

40 ml of the crude enzyme thus obtained, 44 ml of artificial seawater, 510 mg of the above-mentioned sulfated-fucose-containing polysaccharide-F and 36 ml of water are mixed together and the pH value of the mixture is adjusted to 8. After reacting at 25° C. for 48 hours, the reaction mixture is subjected to gel filtration by using Cellulofine GCL-300 and thus divided into four fractions which are referred to, in order of molecular weight, as F-Fd-1 (molecular weight: more than 25,000), F-Fd-2 (molecular weight: 12,000–25,000), F-Fd-3 (molecular weight: 6,500–12,000) and F-Fd-4 (molecular weight: 65,000 or less). These fractions are desalted and freeze-dried to thereby give 170, 270, 300 and 340 mg of the dry preparations respectively.

Figure 9:
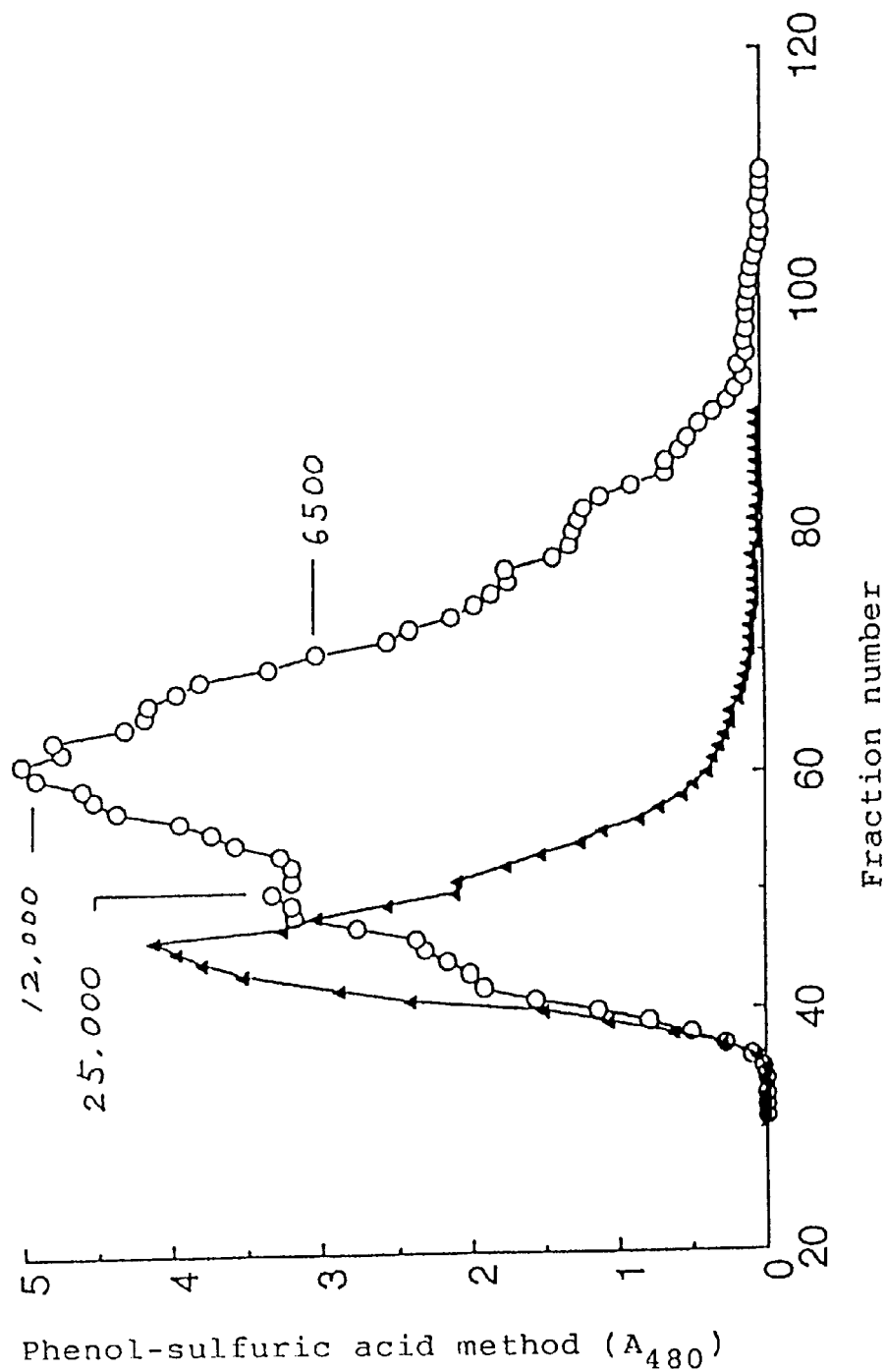
FIG. 9 shows the molecular weight distributions of the sulfated-fucose-containing polysaccharide-F determined by the gel filtration method with the use of Cellulofine GCL-300 before and after degrading with the endo-sulfated-fucose-containing polysaccharide degrading enzyme.

FIG. 9 shows the results of gel filtration with Cellulofine GCL-300 of the enzymatic digestion products of the sulfated-fucose-containing polysaccharide-F, i.e., the degradation products. In FIG. 9, the ordinate refers to the absorbance at 480 nm (color development determined by the phenol-sulfuric acid method) while the abscissa refers to the fraction number. Each fraction has 10 ml of the eluate. The column is 1,075 ml in volume and a 0.2 M solution of ammonium acetate containing 10% of ethanol is employed as the eluent.

In FIG. 9, the open circle shows the result of the gel filtration of the sulfated-fucose-containing polysaccharide-F which has been degraded with the enzyme, while the solid triangle stands for the results of the gel filtration of the sulfated-fucose-containing polysaccharide-F prior to the enzymatic degradation.

From the above-mentioned results of the Cellulofine GCL-300 gel filtration, the reaction product of the sulfated-fucose-containing polysaccharide-F degrading enzyme has a molecular weight distribution ranging from about 1,000 to 30,000.

(2) Analysis on Reducing-end Saccharide and Neutral Saccharide Composition in Enzymatic Reaction product:

A portion of each of the above-mentioned F-Fd-1, F-Fd-2, F-Fd-3 and F-Fd-4 is sampled and the reducing end thereof is pyridyl-(2)-aminated (PA) by using GlycoTAG and GlycoTAG Reagent Kit. The (PA-F-Fd-1), (PA-F-Fd-2), (PA-F-Fd-3) and (PA-F-Fd-4) thus obtained are hydrolyzed by treating with 4 N hydrochloric acid at 100° C. for 3 hours and the reducing-end saccharides are examined by HPLC.

The HPLC is performed under the following conditions:

| | |
|---|---|
| apparatus | Model L-6200 (mfd. by Hitachi, Ltd.); |
| column | PALPAK Type A (4.6 mm × 150 mm) (mfd. by Takara Shuzo Co., Ltd.); |
| eluent | 700 mM borate buffer (pH 9.0) acetonitrile = 9:1; |
| detection | Fluorometric Detector F-1150 (mfd. by Hitachi, Ltd.), excitation wavelength: 310 nm, fluorescent wavelength: 380 nm; |
| flow rate | 0.3 ml/min; |
| column temperature | 65° C. |

As a result, it is found out that (PA-F-Fd-1), (PA-F-Fd-2), (PA-F-Fd-3) and (PA-F-Fd-4) all carry fucose as the reducing-end saccharide.

Further, the neutral saccharide compositions of F-Fd-1, F-Fd-2, F-Fd-3 and F-Fd-4 are determined in the following manner. The sulfated-fucose-containing polysaccharide-F employed as the substrate is hydrolyzed with sulfuric acid and the reducing ends of the constituting saccharides thereof are pyridyl-(2)-aminated (PA) by using GlycoTAG and GlycoTAG Reagent Kit and then analyzed by HPLC under the same conditions as those employed in the analysis of the above enzymatic reaction products. As a result, only fucose and galactose having L- and D-configurations respectively are detected. Thus only L-fucose and D-galactose are examined regarding the products.

Namely, the contents of D-galactose, which is one of the constituting saccharides, are determined in the following manner. By using F-Kit Lactose/Galactose (mfd. by Boehringer Mannheim-Yamanouchi), a reaction system by which D-galactose alone can be determined is constructed in accordance with the manufacturer's description. Separately, F-Fd-1, F-Fd-2, F-Fd-3 and F-Fd-4 are hydrolyzed with 4 N hydrochloric acid at 100° C. for 2 hours and, after neutralization, subjected to the determination in this reaction system.

On the other hand, the contents of L-fucose, which is another constituting saccharide, are determined in the following manner. In accordance with the method described in Clinical Chemistry, 36, 474–476 (1990), F-Fd-1, F-Fd-2, F-Fd-3 and F-Fd-4 are hydrolyzed with 4 N hydrochloric acid at 100° C. for 2 hours and, after neutralization, subjected to the determination in this reaction system.

As a result, it is found out that F-Fd-1, F-Fd-2, F-Fd-3 and F-Fd-4 show L-fucose to D-galactose ratios of 100:44, 100:27, 100:5 and 100:1, respectively.

These results may be summarized as follows. The endo-sulfated-fucose-containing polysaccharide-F degrading enzyme acts on the sulfated-fucose-containing polysaccharide-F and hydrolyzes the fucosyl bonds, thus forming degradation products of about 1,000 to 30,000 in molecular weight. Among these degradation products, one having a higher molecular weight shows a larger galactose content. All of these degradation products have L-fucose as the reducing end.

Next, the substrate specificity of this enzyme is examined by treating the sulfated-fucose-containing polysaccharide-U with the sulfated-fucose-containing polysaccharide-F degrading enzyme.

Namely, 12 μl of a 2.5% solution of the sulfated-fucose-containing polysaccharide-U, 6 μl of a 1 M solution of calcium chloride, 12 μl of a 1 M solution of sodium chloride, 72 μl of a 50 mM imidazole buffer (pH 7.5) and 18 μl of the endo-sulfated-fucose-containing polysaccharide-F degrading enzyme (1.6 mU/ml) are mixed together and reacted at 30° C. for 3 hours. Then the reaction mixture is treated at 100° C. for 10 minutes and centrifuged. Then the degree of degradation is measured by analyzing a 100 μl portion of the reaction mixture by HPLC.

As a control, use is made of a reaction mixture prepared by the same method but substituting the endo-sulfated-fucose-containing polysaccharide-F degrading enzyme by the buffer used to prepare the endo-sulfated-fucose-containing polysaccharide degrading enzyme solution. This control is also analyzed by HPLC.

The HPLC is performed under the following conditions:

| | |
|---|---|
| apparatus | Model L-6200 (mfd. by Hitachi, Ltd.); |
| column | OHpak KB-804 (8 mm × 300 mm, mfd. by Showa Denko K.K.); |
| eluent | 25 mM imidazole buffer (pH 8) containing 5 mM of sodium azide, 25 mM of calcium chloride and 50 mM of sodium chloride; |
| detection | differential refractometric detector (Shodex RI-71, mfd. by Showa Denko K.K.); |
| flow rate | 1 ml/min; |
| column temperature | 25° C. |

As a result, the sulfated-fucose-containing polysaccharide-U is not degraded at all by the sulfated-fucose-containing polysaccharide-F degrading enzyme.

As such, degradation products of the sulfated-fucose-containing polysaccharide-F can be prepared by treating a material containing the sulfated-fucose-containing polysaccharide-F with the sulfated-fucose-containing polysaccharide-F degrading enzyme. As the material containing the sulfated-fucose-containing polysaccharide-F, use can be made of, for example, a purified sulfated-fucose-containing polysaccharide-F product, the above-mentioned sulfated-fucose-containing polysaccharide mixture or an extract of brown algae with an aqueous solvent. The material containing the sulfated-fucose-containing polysaccharide-F may be dissolved in a conventional manner. Although the sulfated-fucose-containing polysaccharides may be dissolved in the solution at the highest concentration, the concentration is usually determined by taking the workability and enzyme titer into consideration.

The solvent for the sulfated-fucose-containing polysaccharide-F solution may be appropriately selected from among water, buffers and the like depending on the purpose. The pH value of the solution usually falls within the neutral region and the enzymatic reaction is generally effected at about 30° C. The molecular weights of the degradation products can be regulated by controlling the amount of the enzyme, reaction time, etc.

Next, the degradation products are subjected to molecular weight fractionation to thereby give the degradation products of the sulfated-fucose-containing polysaccharide-F with more uniform molecular weight distribution. The molecular weight fractionation may be carried out by using commonly employed procedures such as gel filtration or the use of a molecular weight fractionation membrane. The degradation products may be further subjected to purifying treatments with, for example, an ion exchange resin or activated carbon, if needed. It is also possible that the degradation products are desalted, sterilized and freeze-dried to thereby give a dry preparation of the degradation products of the present invention, if necessary.

Sulfated-fucose-containing polysaccharide-U may, for example, be prepared as mentioned in Referential Examples 5 and 6. As hereunder, physicochemical properties of this sulfated-fucose-containing polysaccharide-U will be given although the sulfated-fucose-containing polysaccharide-U used in the present invention is not limited to said examples only. Incidentally, the physicochemical properties of the sulfated-fucose-containing polysaccharide-U were measured by the same method as mentioned in the above-given measuring method for sulfated-fucose-containing polysaccharide-F.

Figure 10:
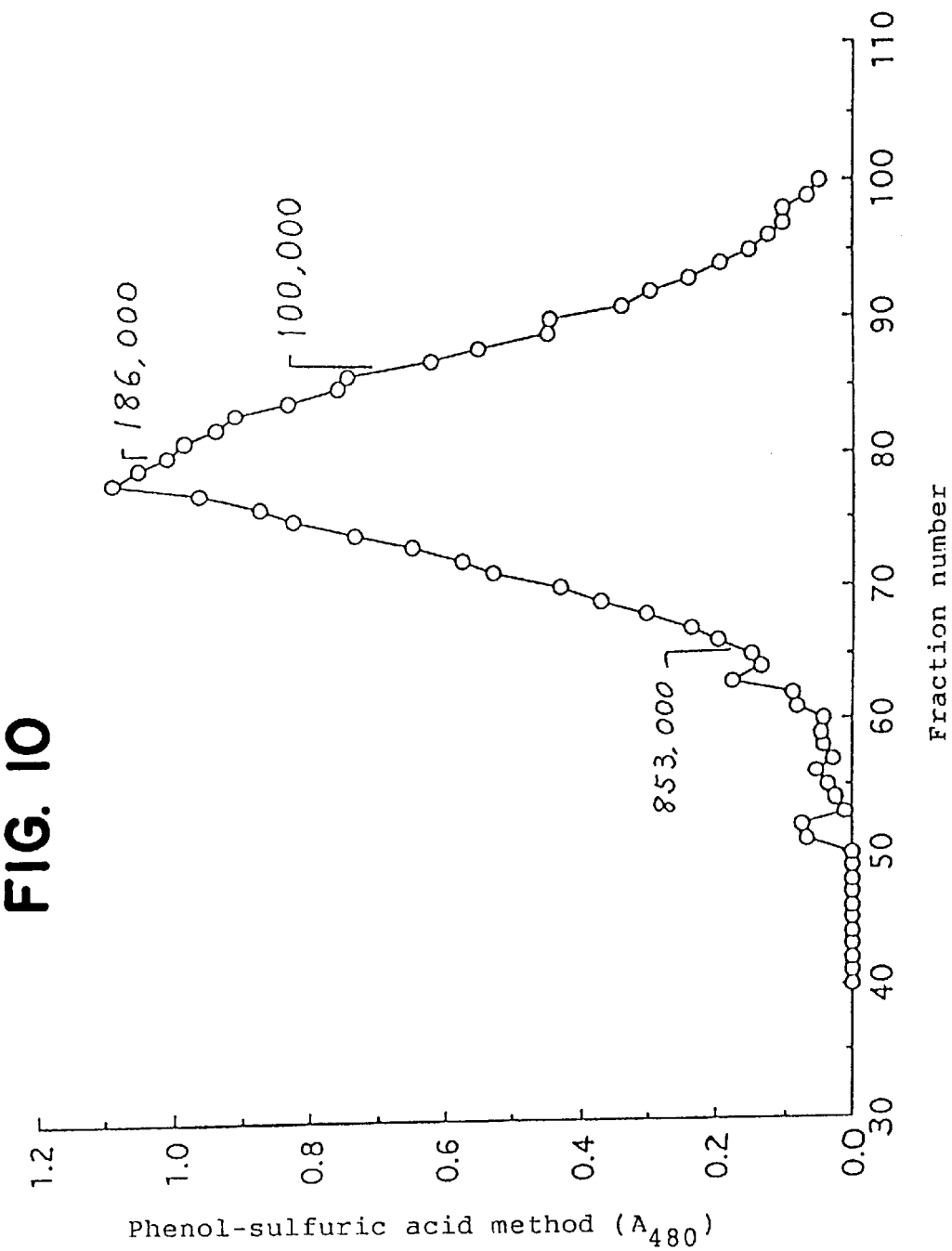
FIG. 10 shows the molecular weight distribution of the sulfated-fucose-containing polysaccharide-U determined by the gel filtration method with the use of Sephacryl S-500.

The molecular weight of the sulfated-fucose-containing polysaccharide-U to be used in the present invention thus obtained is determined by the gel filtration method with the use of Sephacryl S-500. As a result, it shows a molecular weight distribution around about 190,000 (FIG. 10). In FIG. 10, the ordinate refers to the saccharide content of the sample determined by the phenol-sulfuric acid method which is expressed in the absorbance at 480 nm while the abscissa refers to the fraction number.

Next, the components of the sulfated-fucose-containing polysaccharide-U of the present invention thus obtained are analyzed.

It is found out that the constituting saccharides of the sulfated-fucose-containing polysaccharide-U obtained above are fucose, mannose, galactose, glucose, rhamnose, xylose and uronic acid and no other neutral saccharide is substantially contained therein. The composition ratio by mol of the major components is as follows; fucose: mannose: galactose: uronic acid: sulfate group=about 10:7:4:5:20.

Figure 11:
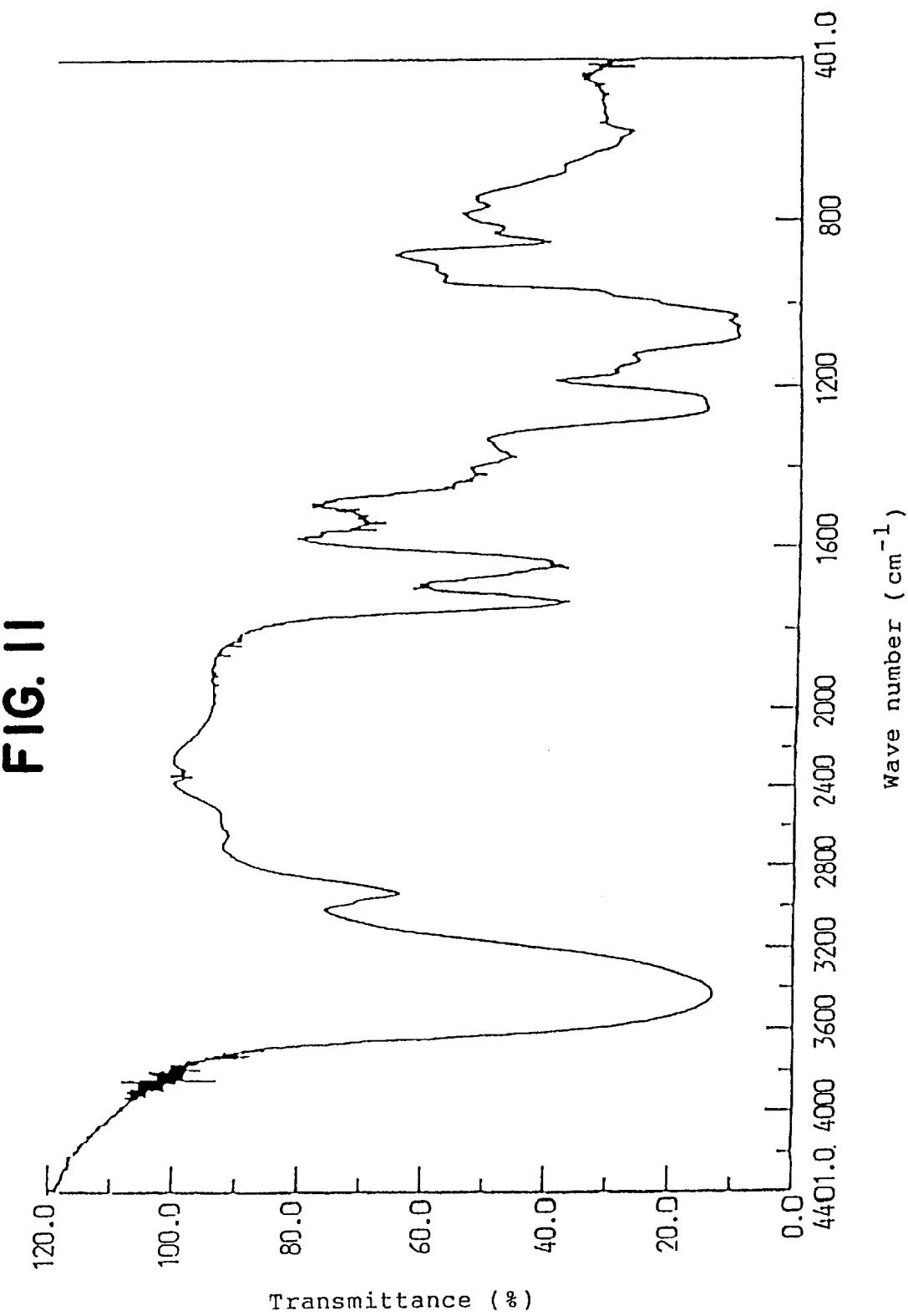
FIG. 11 is the IR spectrum of the sulfated-fucose-containing polysaccharide-U.

Then the IR spectrum of the sulfated-fucose-containing polysaccharide-U is measured. Thus the spectrum as shown in FIG. 11 is obtained. In FIG. 11, the ordinate refers to the transmittance (%) while the abscissa refers to the wave number ($cm^{-1}$)

Next, the NMR spectrum of calcium salt of the sulfated-fucose-containing polysaccharide-U is measured. Thus the spectrum as shown in FIG. 12 is obtained.

Figure 12:
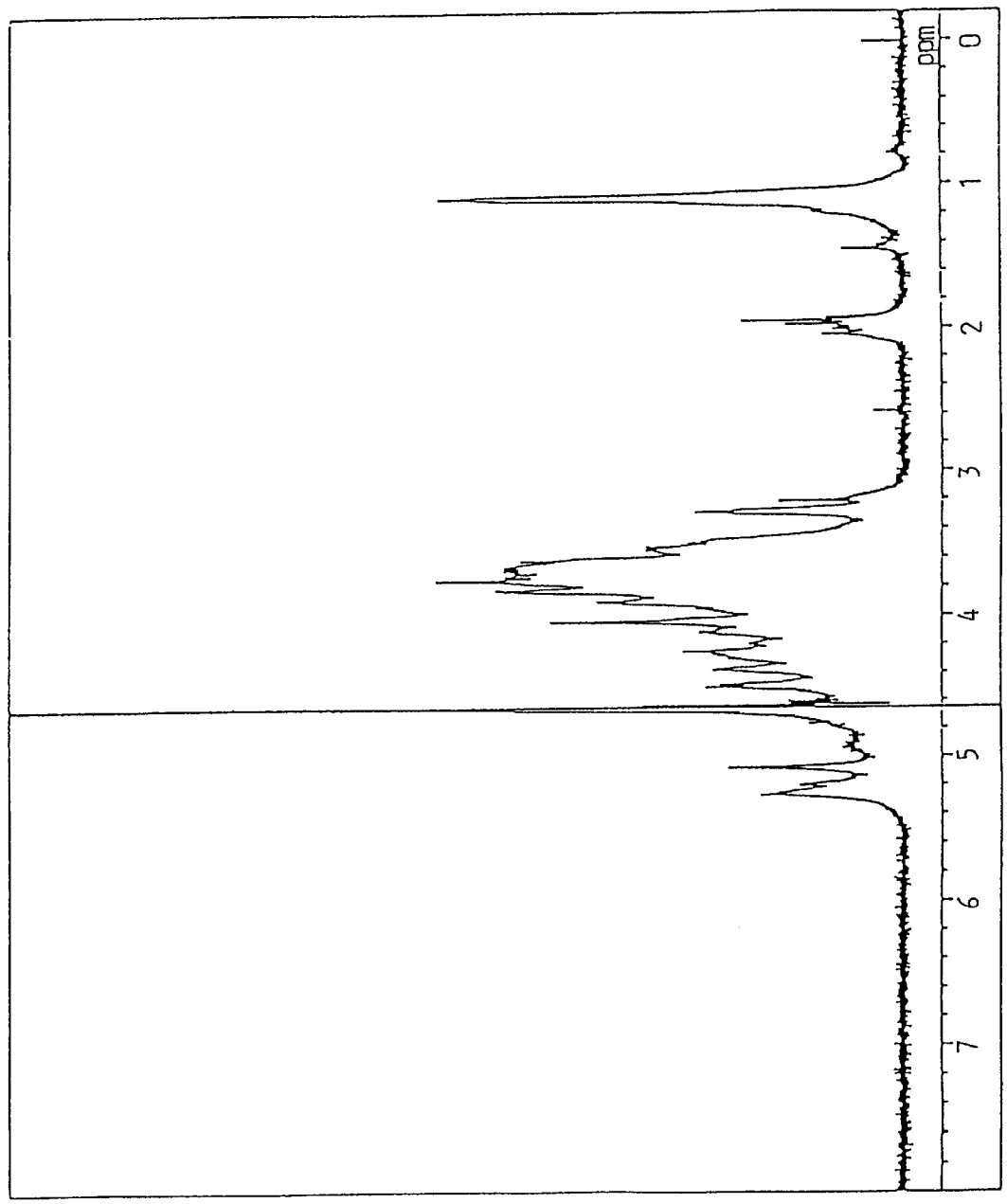
FIG. 12 is the $^1$H-NMR spectrum of the sulfated-fucose-containing polysaccharide-U.

In FIG. 12, the ordinate refers to the signal intensity while the abscissa refers to the chemical shift (ppm). The chemical shifts in $^1$H-NMR are expressed by taking the chemical shift of HOD as 4.65 ppm.

$^1$H-NMR (D2O):

δ 5.27 (H at the 1-position of mannose), 5.07 (H at the 1-position of fucose), 4.49 (H at the 3-position of fucose), 4.37 (H at the 1-position of glucuronic acid), 4.04 ((H at the 4-position of fucose), 3.82 (H at the 2-position of fucose), 3.54 (H at the 3-position of glucuronic acid), 3.28 (H at the 2-position of glucuronic acid), 1.09 (H in $CH_3$ at the 5-position of fucose).

When measured with a high-speed, high-sensitivity polarimeter SEPA-300 (mfd. by Horiba Seisakusho), the freeze-dried product of the sulfated-fucose-containing polysaccharide-U has a specific rotation of −53.6°.

Structure of sulfated-fucose-containing polysaccharide-U has been elucidated already as mentioned in the specification of the Japanese Patent Application No. 45583/1996.

Degradation of sulfated-fucose-containing polysaccharide-U with degrading enzyme capable of degrading sulfated-fucose-containing polysaccharide-U and purification of the degradation product:

The purified sulfated-fucose-containing polysaccharide-U is treated with an endofucoidanase described in WO96/34004 and the degradation products are purified.

Namely, 16 ml of a 1% solution of the sulfated-fucose-containing polysaccharide-U, 12 ml of a 50 mM phosphate buffer (pH 8.0), 4 ml of a 4 M solution of sodium chloride and 8 ml of a 32 mU/ml solution of the endofucoidanase are mixed together and reacted at 25° C. for 48 hours. It is confirmed that the absorbance of the reaction mixture at 230 nm is elevated as the reaction proceeds, thus proving that the degradation of the sulfated-fucose-containing polysaccharide-U with this enzyme is in progress. After desalting with a Micro Acilyzer G3 (mfd. by Asahi Chemical Industry Co., Ltd.), the reaction mixture is separated into three fractions (a), (b) and (c) and purified with a DEAE-Sepharose FF.

The strain to be used in the production of the above-mentioned endofucoidanase may be an arbitrary one, so long as it is capable of producing the endofucoidanase. As a particular example thereof, citation can be made of Flavobacterium sp. SA-0082 (FERM BP-5402) described in WO96/34004.

Analysis on the Structure of Enzyme Reaction Product:

The above-mentioned endofucoidanase is an enzyme which exclusively degrades the α 1→4 bond between D-mannose and D-glucuronic acid in the sulfated-fucose-containing polysaccharide-U. When the sulfated-fucose-containing polysaccharide-U obtained above is treated with this enzyme, oligosaccharides having the structures represented by the following formulae (I), (II) and (III) are formed:

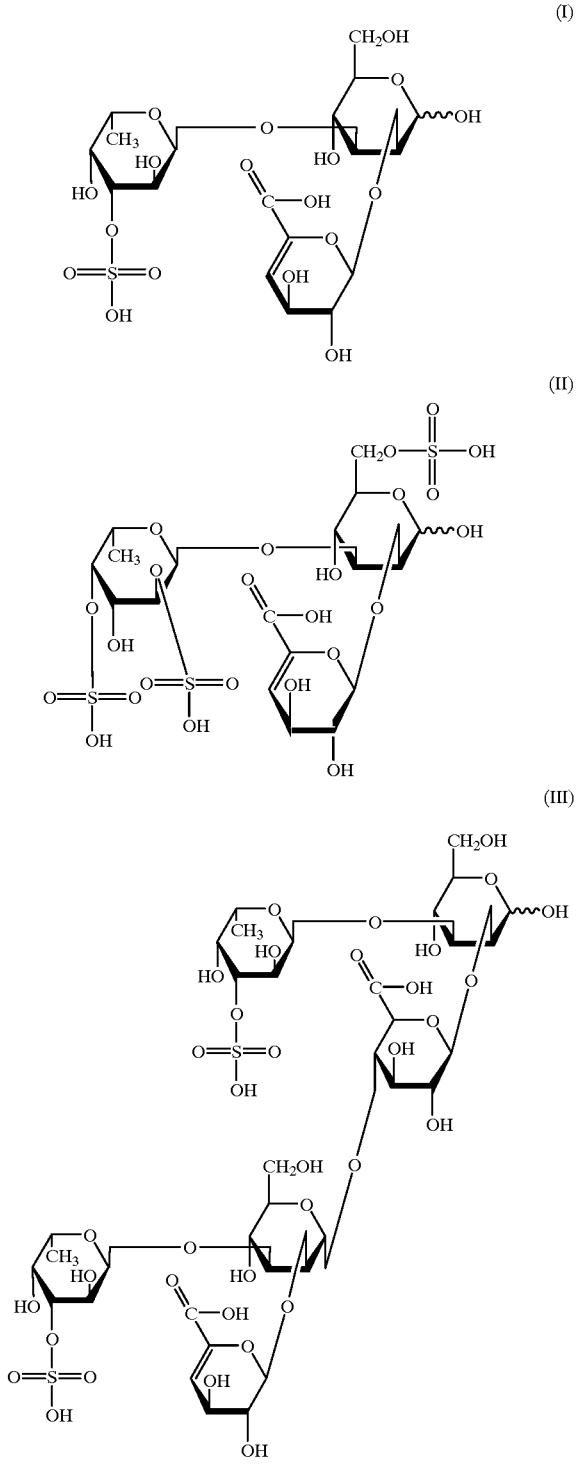

(I)
(II)
(III)

Now, detailed description will be given.

A portion of each of the above-mentioned three fractions (a), (b) and (c) separated and purified by DEAE-Sepharose FF is pyridyl-(2)-aminated (PA) at the reducing end by using GlycoTAG and GlycoTAG Reagent Kit to thereby give PA saccharides (PA-a), (PA-b) and (PA-c), which are then analyzed by HPLC.

The HPLC is performed under the following conditions:
(i) HPLC analysis by using molecular weight fractionation column:

| apparatus | Model L-6200 (mfd. by Hitachi, Ltd.); |
|---|---|
| column | SHODEX SB-803 (4.6 × 250 mm, mfd. by Showa Denko, K.K.); |
| eluent | 0.2M sodium chloride: dimethyl sulfoxide = 9:1; |
| detection | Fluorometric Detector F-1150 (mfd. by Hitachi, Ltd.), excitation wavelength: 320 nm, fluorescent wavelength: 400 nm; |
| flow rate | 1 ml/min; and |
| column temperature | 50° C. |

(ii) HPLC analysis with the use of reversed phase column:

| apparatus | Model L-6200 (mfd. by Hitachi, Ltd.); |
|---|---|
| column | L-column (4.6 × 250 mm, mfd. by Kagaku Yakuhin Kensa Kyokai); |
| eluent | 50 mM acetic acid-triethylamine (Ph 5.5); |
| detection | Fluorometric Detector F-1150 (mfd. by Hitachi, Ltd.), excitation wavelength: 320 nm, fluorescent wavelength: 400 nm; |
| flow rate | 1 ml/min; and |
| column temperature | 40° C. |

Figure 13:
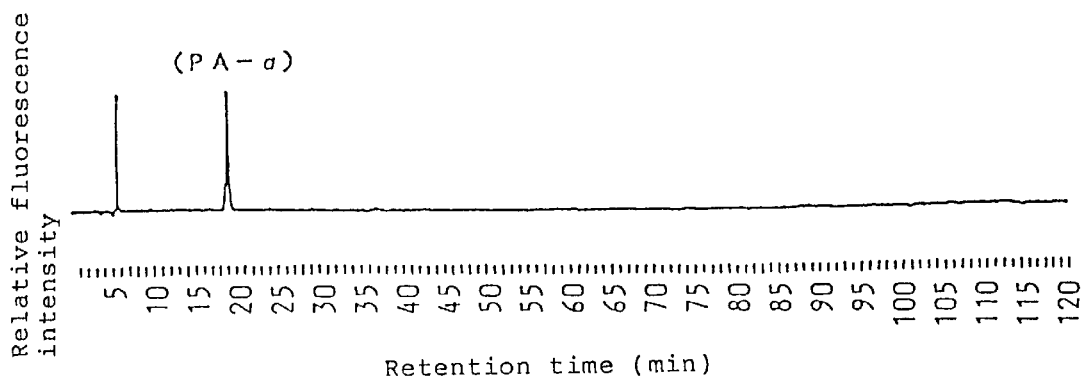
FIG. 13 shows the elution pattern of the saccharide compound (a) having been pyridyl-(2)-aminated (PA-a) which is eluted from an L-column.
Figure 14:
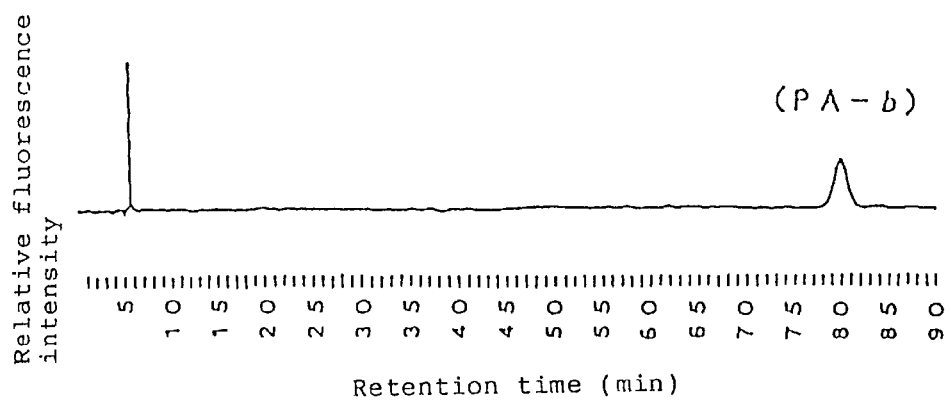
FIG. 14 shows the elution pattern of the saccharide compound (b) having been pyridyl-(2)-aminated (PA-b) which is eluted from an L-column.
Figure 15:
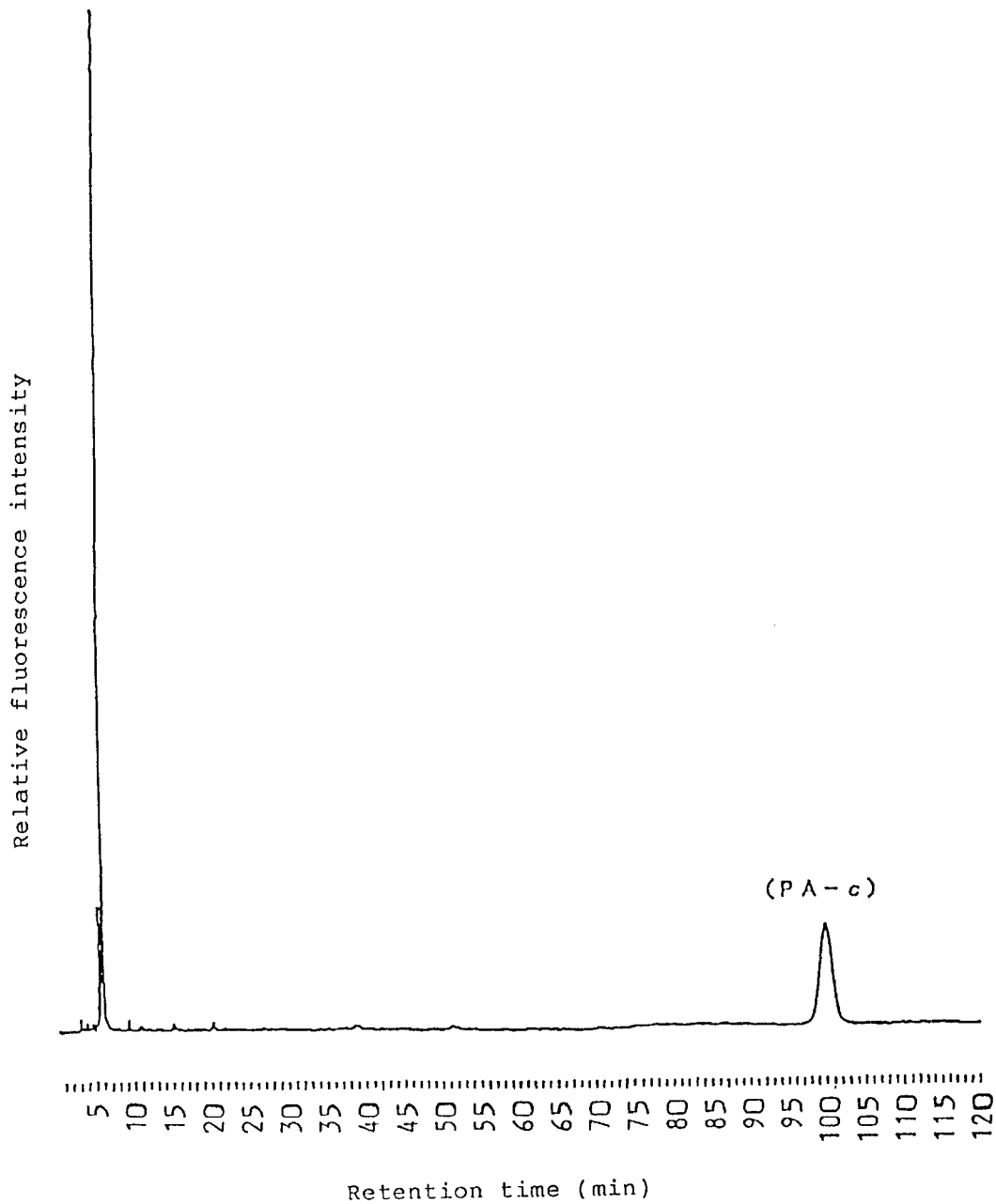
FIG. 15 shows the elution pattern of the saccharide compound (c) having been pyridyl-(2)-aminated (PA-c) which is eluted from an L-column.

FIGS. 13, 14 and 15 respectively show the HPLC elution patterns of the pyridyl-(2)-aminated saccharide compounds (PA-a), (PA-b) and (PA-c). In each figure, the ordinate refers to the relative fluorescence intensity while the abscissa refers to the retention time (min).

Next, the physical properties of the compounds (a), (b) and (c), i.e., those represented by the formulae (I), (II) and (II) will be illustrated.

Figure 16:
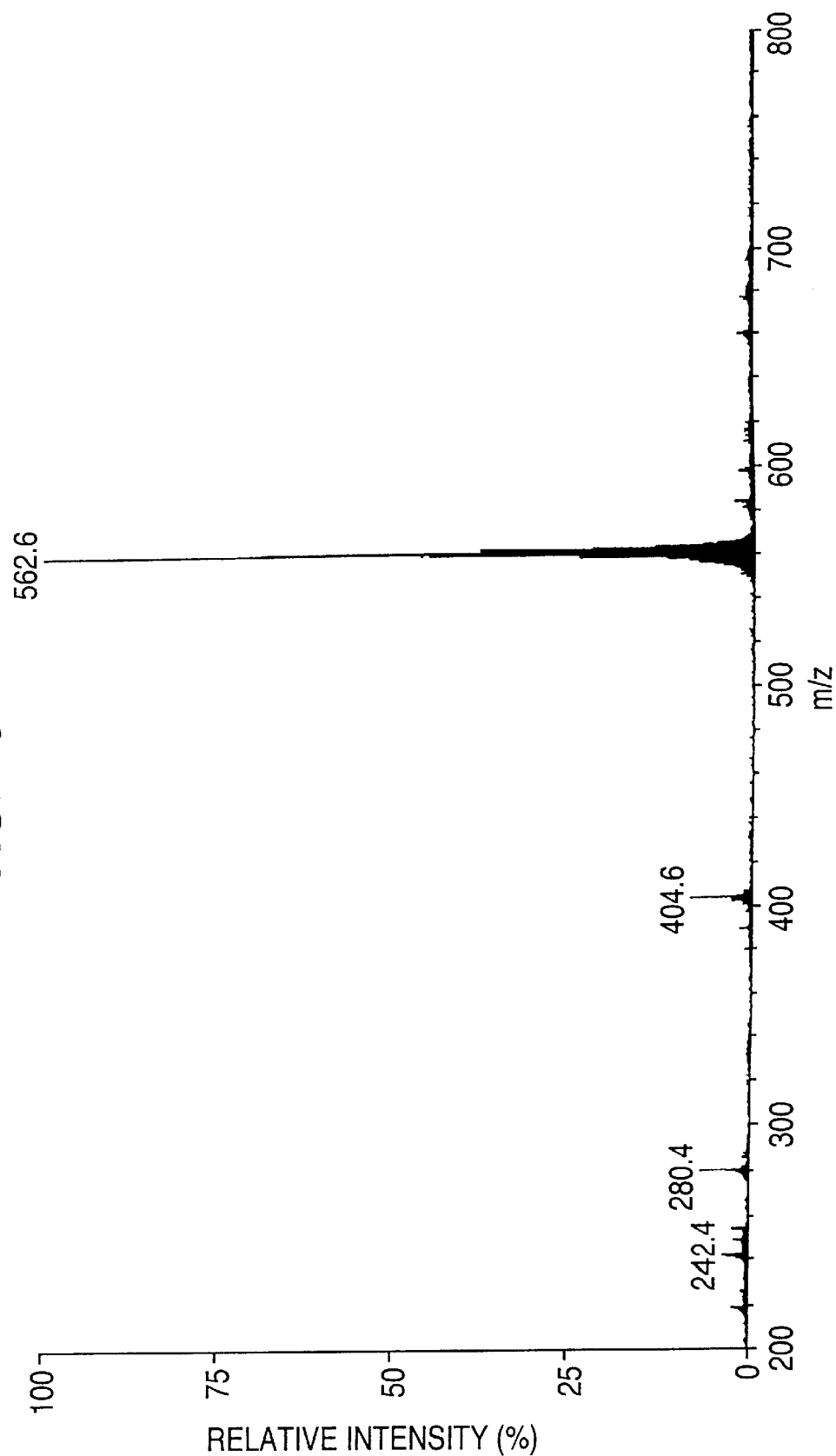
FIG. 16 is the mass spectrogram (negative measurement) of the saccharide compound (a).
Figure 17:
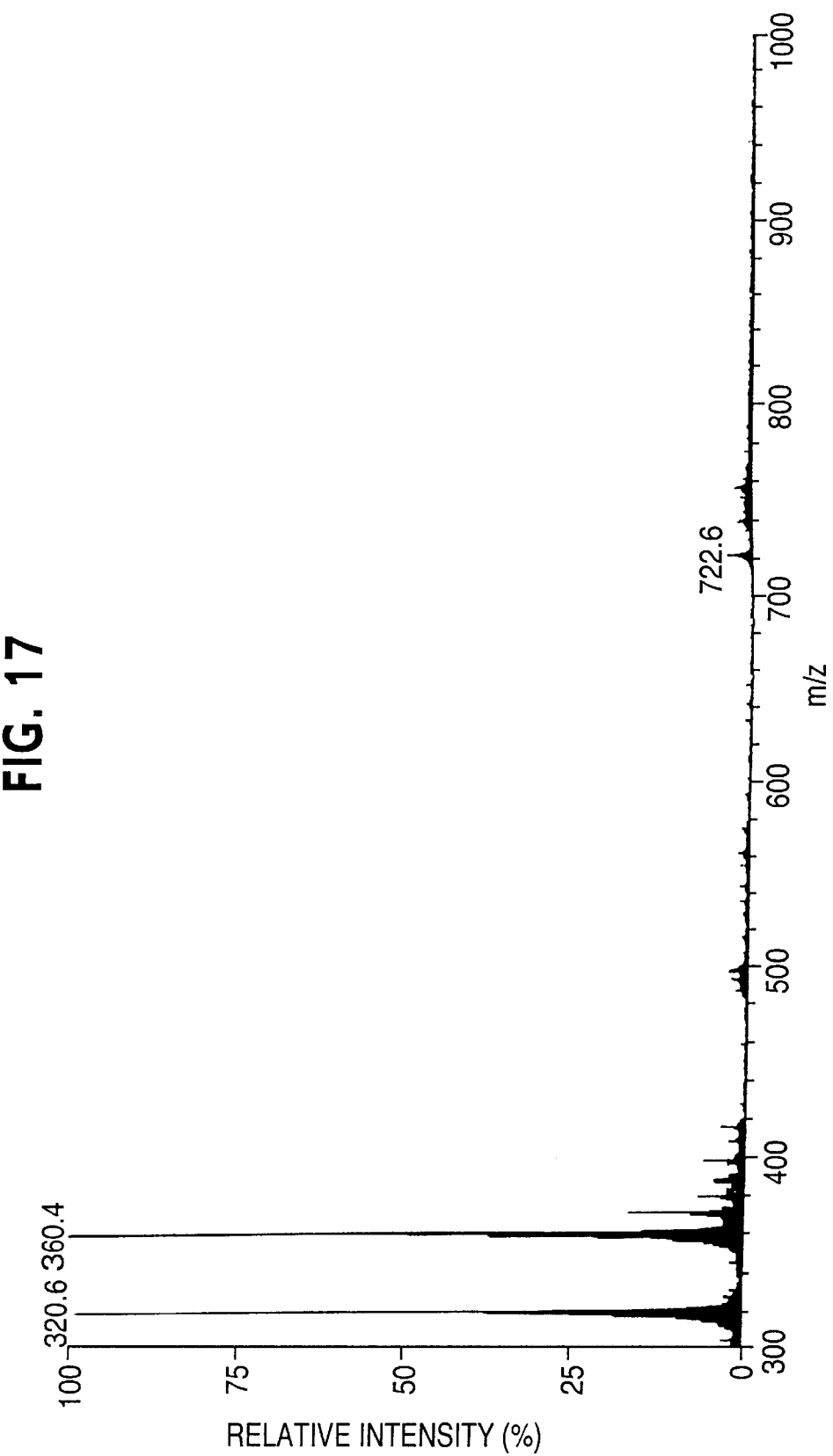
FIG. 17 is the mass spectrogram (negative measurement) of the saccharide compound (b).
Figure 18:
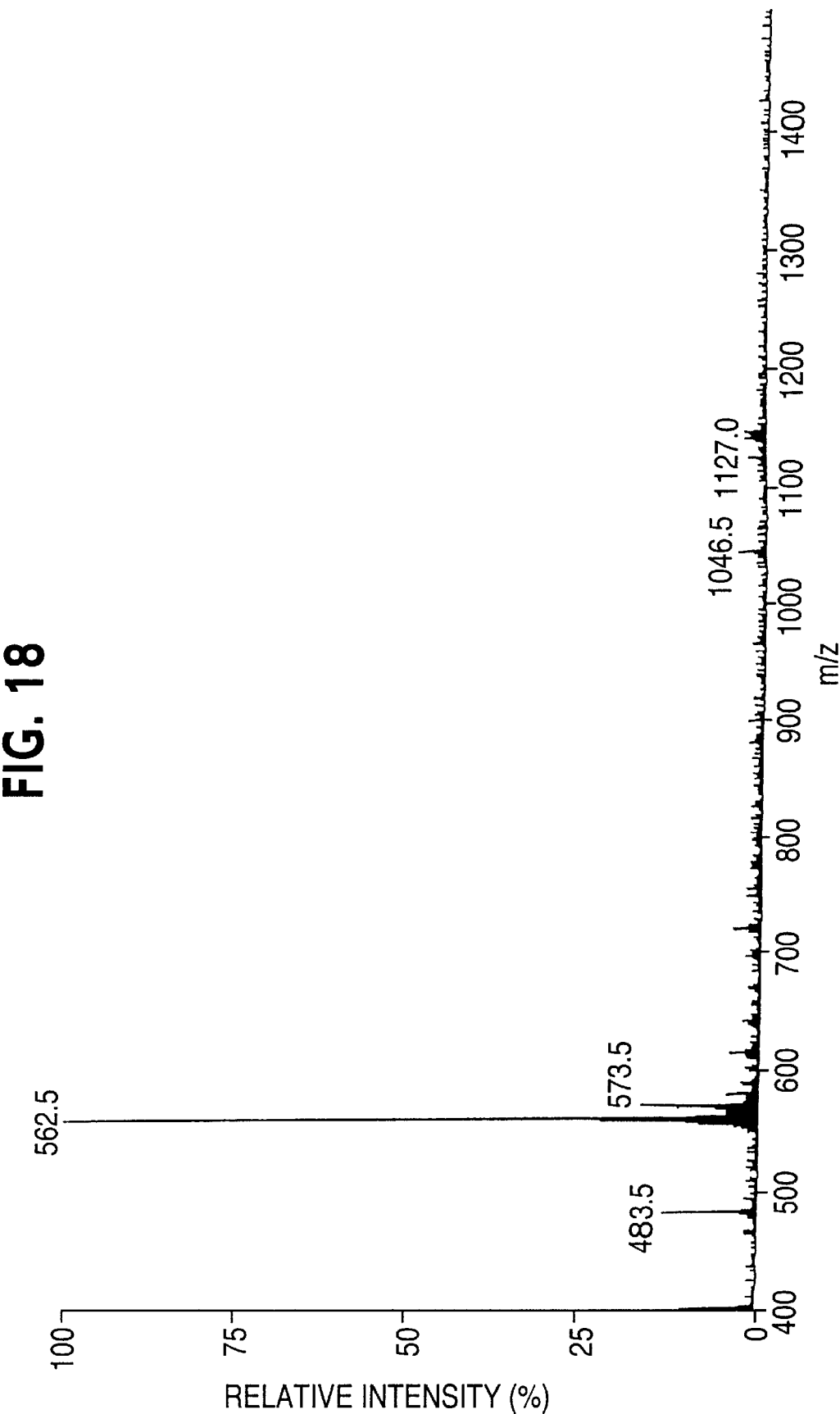
FIG. 18 the mass spectrogram (negative measurement) of the saccharide compound (c).
Figure 19:
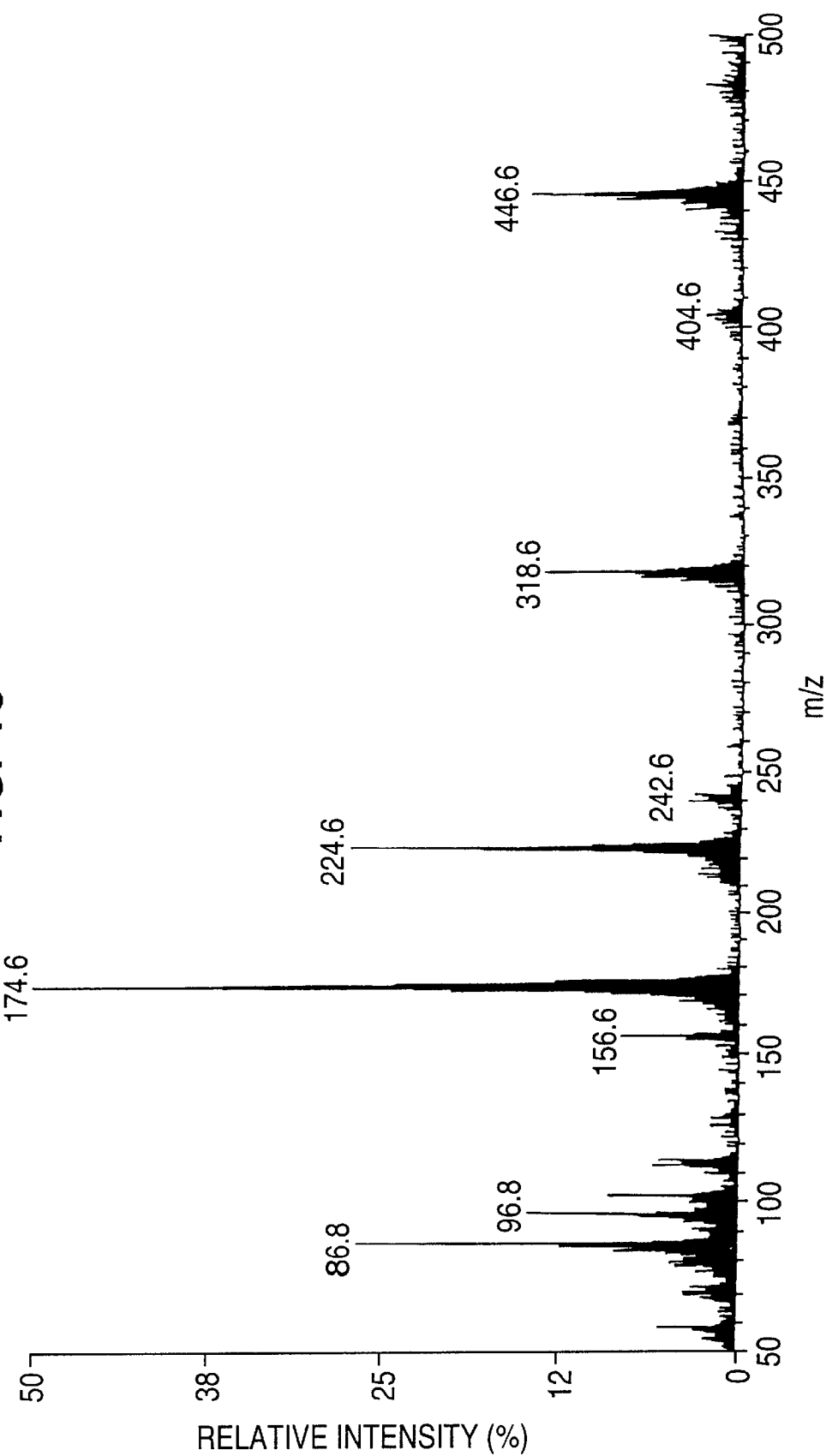
FIG. 19 is the mass-mass spectrogram (negative measurement) of the saccharide compound (a).
Figure 20:
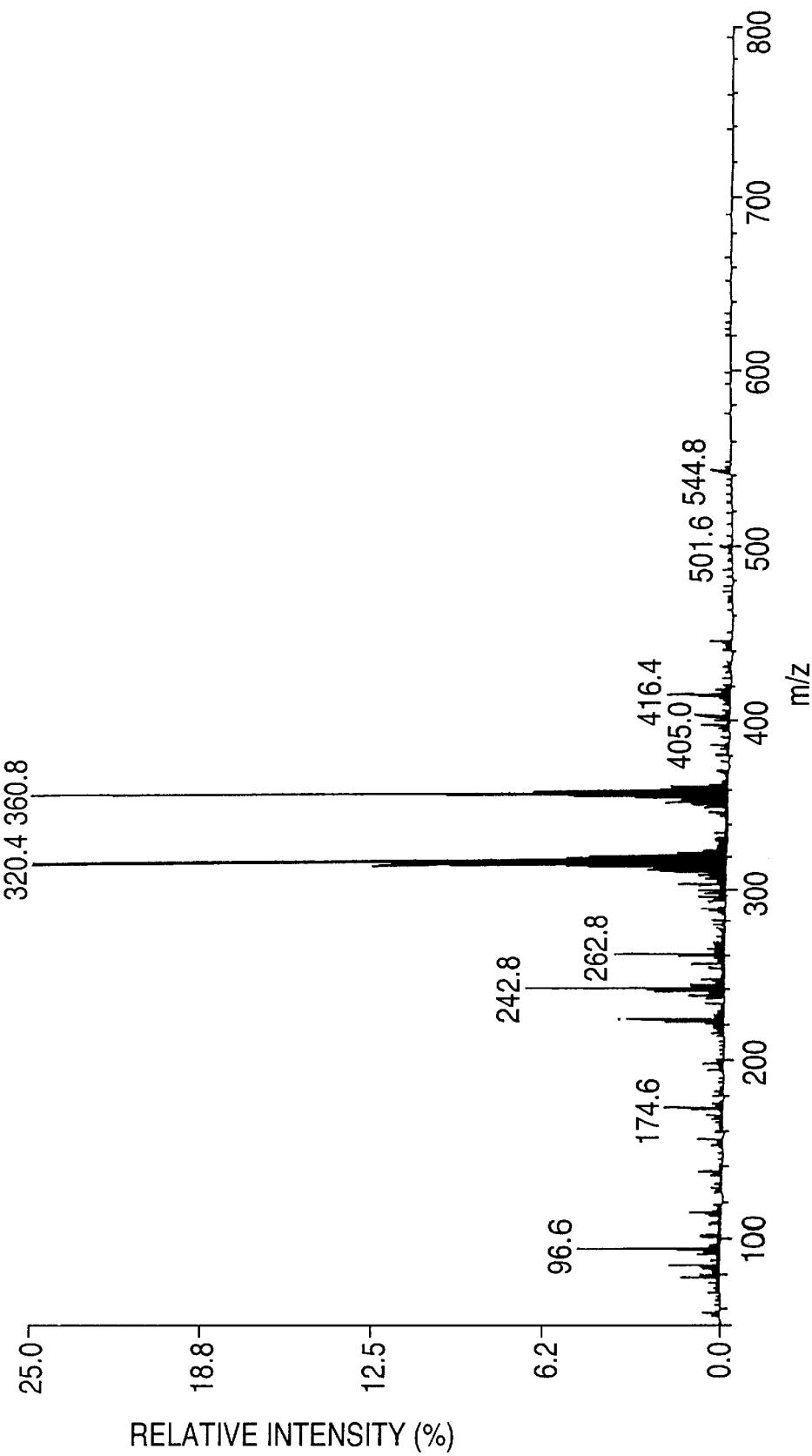
FIG. 20 is the mass-mass spectrogram (negative measurement) of the saccharide compound (b).
Figure 21:
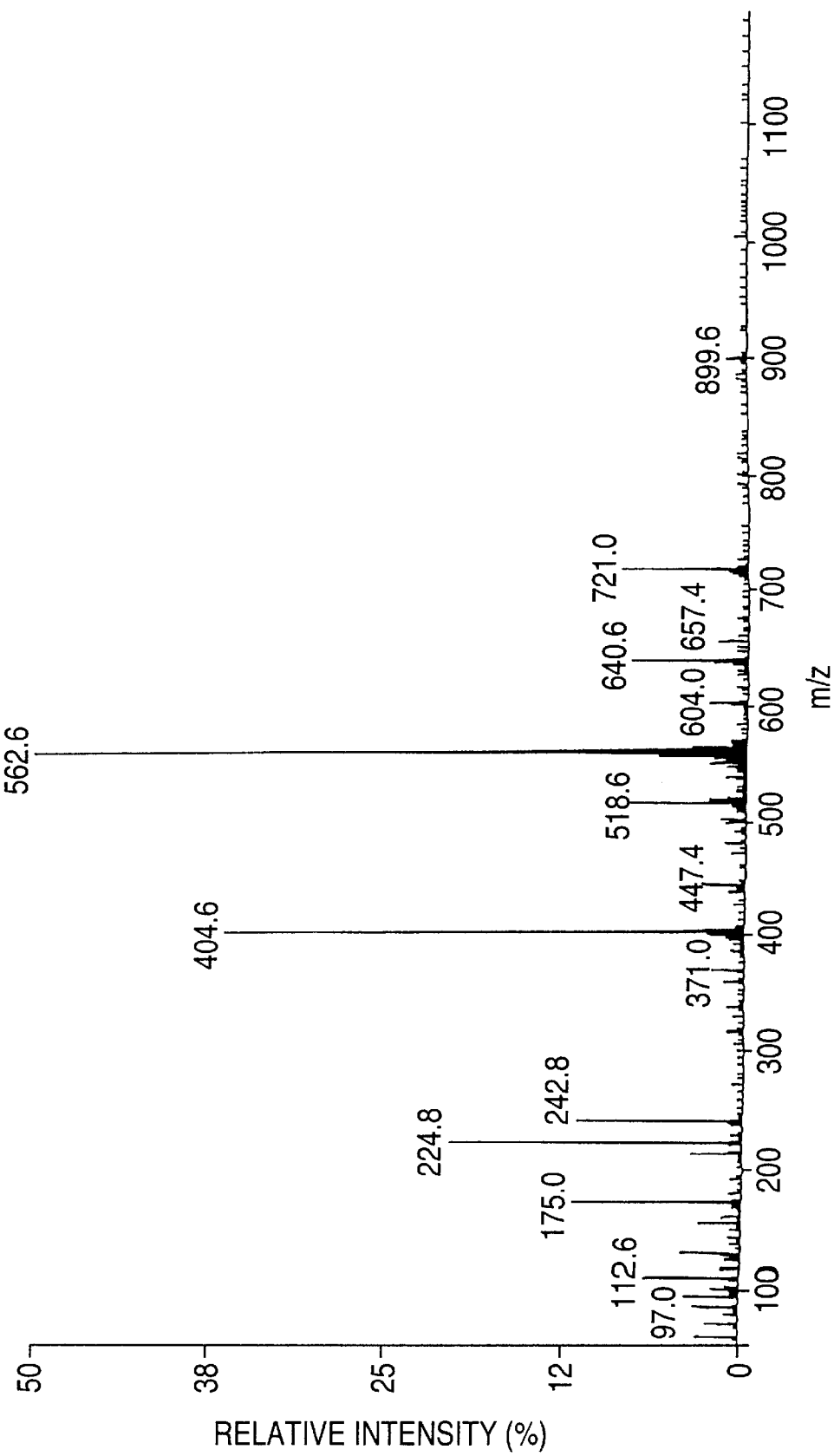
FIG. 21 is the mass-mass spectrogram (negative measurement) of the saccharide compound (c).

FIGS. 16, 17 and 18 respectively show the mass spectra of the compounds (a), (b) and (c), while FIGS. 19, 20 and 21 respectively show the mass-mass spectra of the compounds (a), (b) and (c). In each figure, the ordinate refers to the relative intensity (%) while the abscissa refers to the m/z value.

Figure 22:
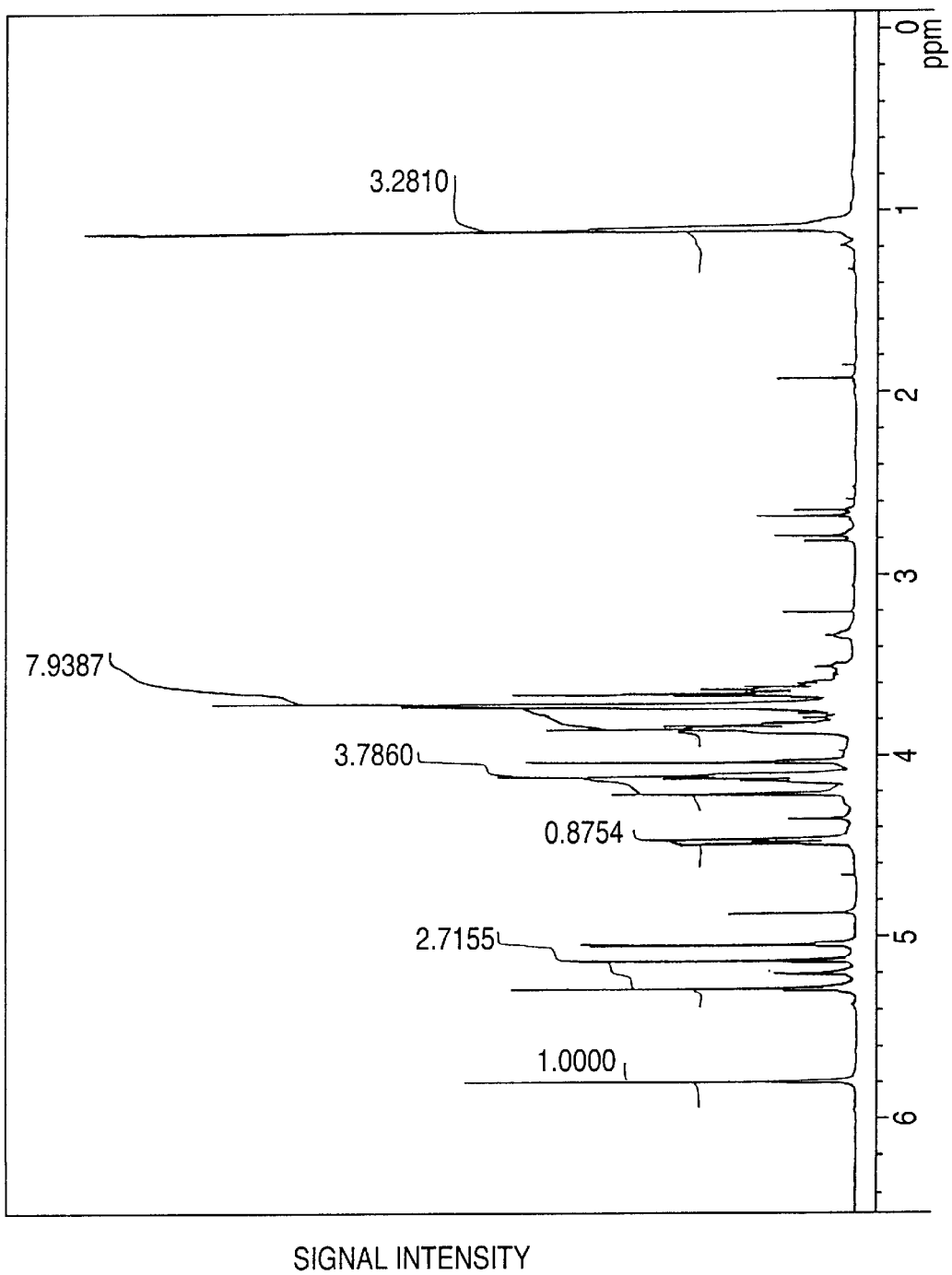
FIG. 22 is the $^1$H-NMR spectrum of the saccharide compound (a).
Figure 23:
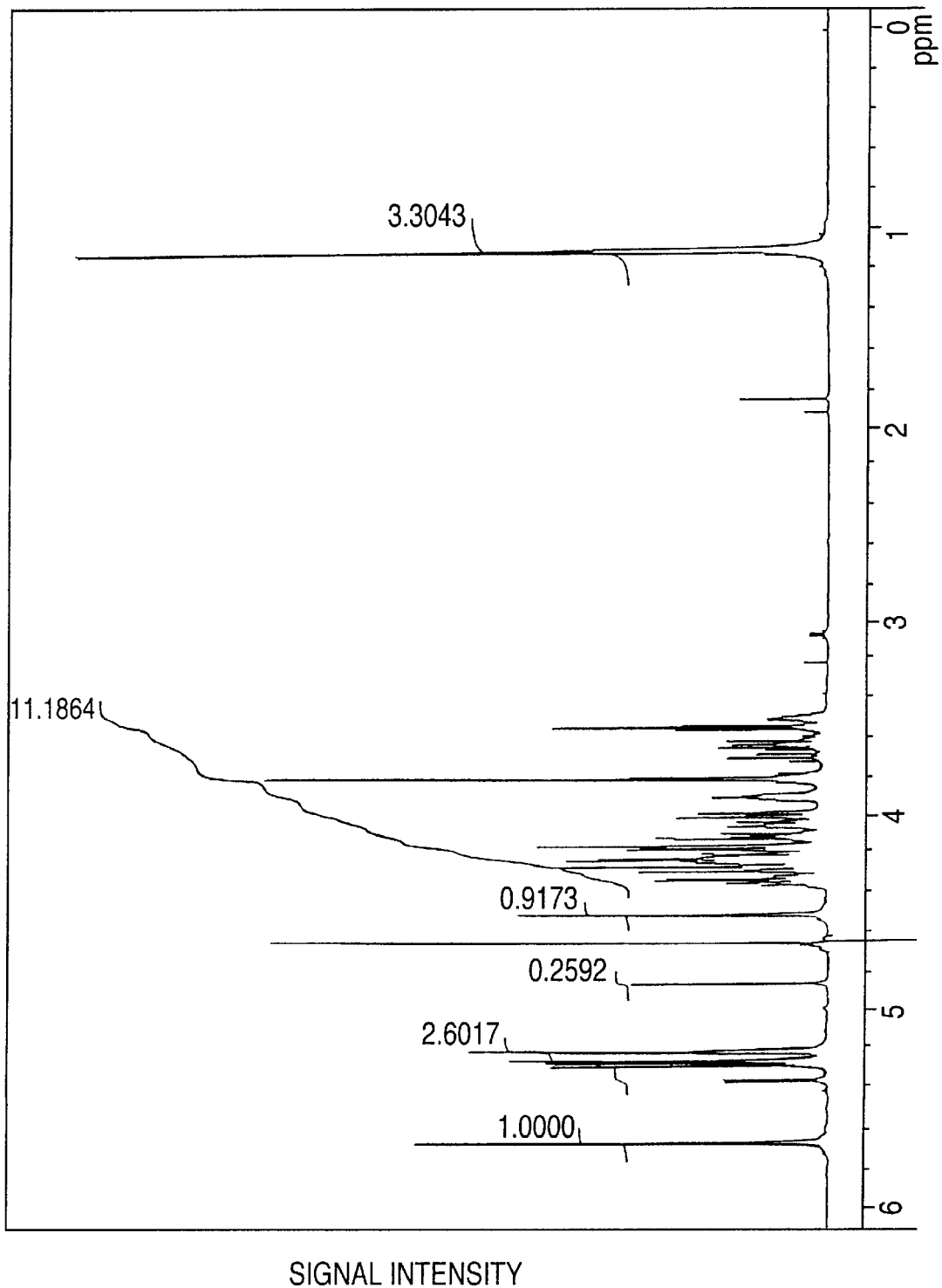
FIG. 23 is the $^1$H-NMR spectrum of the saccharide compound (b).
Figure 24:
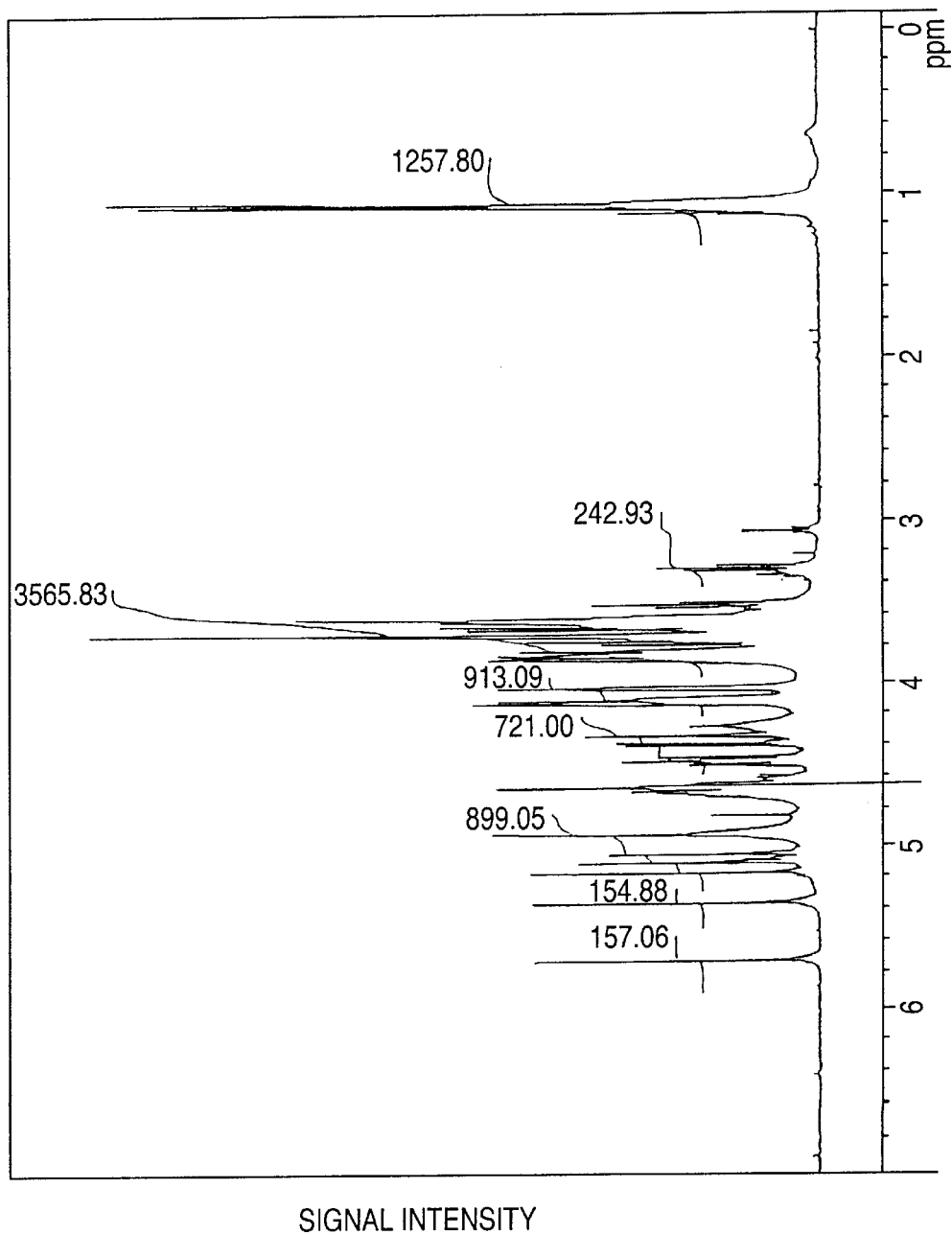
FIG. 24 is the $^1$H-NMR spectrum of the saccharide compound (c).

Moreover, FIGS. 22, 23 and 24 respectively show the $^1$H-NMR spectra of the compounds (a), (b) and (c) In each figure, the ordinate refers to the signal intensity while the abscissa refers to the chemical shift (ppm).

The chemical shifts in $^1$H-NMR are expressed by taking the chemical shift of HOD as 4.65 ppm.

Physical properties of the compound (a):

| Molecular weight | 564. |
|---|---|
| MS m/z | 563 [M-H$^+$]$^-$. |
| MS/MS m/z | 97 [HSO$_4$]$^-$, 157 [unsaturated D-glucuronic acid-H$_2$O-H$^+$]$^-$, 175 [unsaturated D-glucuronic acid-H$^+$]$^-$, 225 [L-fucose sulfate-H$_2$O—H$^+$]$^-$, 243 [L-fucose sulfate-H$^+$]$^-$, 319 [unsaturated D-glucuronic acid bonded to D-mannose-H$_2$O—H$^+$]$^-$, 405 [M-unsaturated D-glucuronic acid-H$^+$]$^-$, 483 [M-SO$_3$—H$^+$]$^+$. |
| $^1$H-NMR (D$_2$O) | |

1H-NMR (D$_2$O); δ 5.78(1H, d, J=3.7 Hz, 4"-H), 5.26(1H, d, J=1.2 Hz, 1-H), 5.12(1H, d, J=4.0 Hz, 1'-H), 5.03(1H, d, J=6.1 Hz, 1"-H), 4.47(1H, d-d, J=3.4, 10.4 Hz, 3'-H), 4.21

(1H, br-s, 2-H), 4.12(1H, m, 5'-H), 4.10(1H, d-d, J=3.7, 5.8 Hz, 3"-H), 4.03(1H, d, J=3.4 Hz, 4'-H), 3.86(1H, m, 3-H), 3.83(1H, d-d, J=4.0, 10.4 Hz, 2'-H), 3.72(1H, m, 4-H), 3.72(1H, m, 5-H), 3.70($H_2$ of 2H, m, 5-$CH_2$), 3.65(1H, d-d, J=5.8, 6.1 Hz, 2"-H), 1.08($H_3$ of 3H, d, J=6.7 Hz, 5'-$CH_3$).

Saccharide Composition:

L-fucose:unsaturated D-glucuronic acid: D-mannose= 1:1:1 (each one molecule).

Sulfate:

one molecule (at the 3-position of L-fucose).

The peaks in $^1$H-NMR are assignable respectively to the positions shown by the numerical values in the following formula (IV):

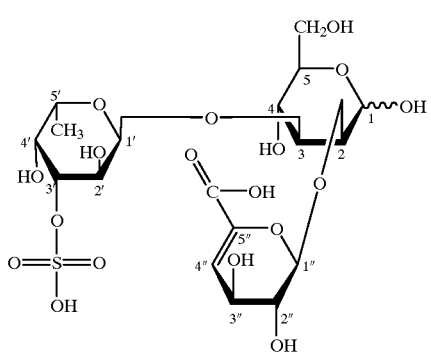

(IV)

Physical properties of the compound (b):

| Molecular weight | 724. |
|---|---|
| MS m/z | 723 [M-H$^+$]$^-$, 361 [M-2H$^+$]$^{2-}$. |
| MS/MS m/z | 97 [HSO$_4$]$^-$, 175 [unsaturated D-glucuronic acid-H$^+$]$^-$, 243 [L-fucose sulfate-H$^+$]$^-$, 321 [M-SO$_3$-2H$^+$]$^{2-}$, 405 [M-unsaturated D-glucuronic acid-SO$_3$—H$^+$]$^-$, 417 [M-L-fucose-2SO$_3$-2H$^+$]$^+$. |
| $^1$H-NMR (D$_2$O) | |

$^1$H-NMR (D$_2$O); δ 5.66(1H, d, J=3.4 Hz, 4"-H), 5.27(1H, d, J=7.3 Hz, 1"-H), 5.22(1H, d, J=1.8 Hz, '-H), 5.21(1H, d, J=3.7 Hz, 1'-H), 4.50(1H, d, J=3.1Hz, 4'-H), 4.32(1H, q, J=6.7 Hz, 5'-H), 4.27(1H, d-d, J=3.7, 10.4 Hz, 2'-H), 4.21 (1H, d-d, J=3.4, 6.7 Hz, 3"-H), 4.18(H of 1H, d-d, J=1.8, 11.0 Hz, 5-CH), 4.15(1H, br-s, 2-H), 4.10(H of 1H, d-d, J=5.8, 11.0 Hz, 5-CH), 3.99(1H, d-d, J=3.1, 10.4 Hz, 3'-H), 3.90(1H, m, 5-H), 3.82(1H, m, 3-H), 3.82(1H, m, 4-H), 3.54(1H, br-t, J=7.3 Hz, 2"-H), 1.11 (H$_3$ of 3H, d, J=6.7 Hz, 5'-$CH_3$).

Saccharide Composition:

L-fucose:unsaturated D-glucuronic acid: D-mannose= 1:1:1 (each one molecule).

Sulfate:

three molecules (at the 2- and 4-positions of L-fucose and the 6-position of D-mannose).

The peaks in $^1$H-NMR are assignable respectively to the positions shown by the numerical values in the following formula (V):

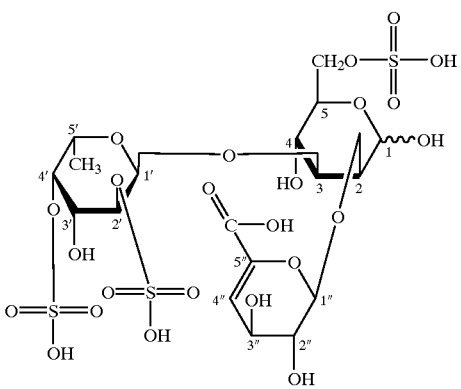

(V)

Physical properties of the compound (c):

| Molecular weight | 1128. |
|---|---|
| MS m/z | 1127 [M-H$^+$]$^-$. |
| MS/MS m/z | 97 [HSO$_4$]$^-$, 175 [unsaturated D-glucuronic acid-H$^+$]$^-$, 225 [L-fucose sulfate-H$_2$O-H$^+$]$^-$, 243 [L-fucose sulfate-H$^+$]$^-$, 371 [M-unsaturated D-glucuronic acid-L-fucose-SO$_3$-2H$^+$]$^{2-}$, 405 [sulfated L-fucose bonded to D-mannose-H$^+$]$^-$, 721 [M-D-mannose-L-fucose-SO$_3$-H$_2$O-H$^+$]$^-$. |
| $^1$H-NMR (D$_2$O) | |

$^1$H-NMR (D$_2$O); δ 5.69(1H, d, J=3.7 Hz, (4)"-H), 5.34 (1H, s, (1)-H), 5.16(1H, s, 1-H), 5.10(1H, d, J=4.0 Hz, (1)'-H), 5.50(1H, d, J=3.7 Hz, 1'-H), 4.93(1H, d, J=6.4 Hz, (1)"-H), 4.50(1H, d-d, J=3.4, 10.7 Hz, 3'-H), 4.47(1H, d-d, J=3.4, 10.4 Hz, (3)'-H), 4.39(1H, d, J=7.9 Hz, 1"-H), 4.33 (1H, br-s, (2)-H), 4.14(1H, m, 2-H), 4.12(1H, m, (3)"-H), 4.12(1H, m, 5'-H), 4.12(1H, m, (5)'-H), 4.04(1H, m, 4'-H), 4.03(1H, m, (4)'-H), 3.85(1H, m, 2'-H), 3.85(1H, m, (2)'-H), 3.82(1H, m, 3-H), 3.82(1H, m, (3)-H), 3.73(1H, m, 4-H), 3.73(1H, m, 5-H), 3.73(1H, m, (4)-H), 3.70(H$_2$ of 2H, m, 5-CH$_2$), 3.70(H$_2$ of 2H, m, (5)-CH$_2$), 3.67(1H, m, 5"-H), 3.62(1H, m, 4"-H), 3.62(1H, m, (2)"-H), 3.62(1H, m, (5)-H), 3.51(1H, t, J=8.9 Hz, 3"-H), 3.28(1H, t, J=7.9 Hz, 2"-H), 1.09(H$_3$ of 3H, d, J=6.7 Hz, (5)'-$CH_3$), 1.07(H$_3$ of 1H, d, J=6.7 Hz, 5'-$CH_3$).

Saccharide Composition:

L-fucose: unsaturated D-glucuronic acid: D-glucuronic acid: D-mannose=2:1:1:2 (two L-fucose molecules, two D-mannose molecules, one unsaturated D-glucuronic acid molecule and one D-glucuronic acid molecule).

Sulfate:

two molecules (at the 3-position of each L-fucose).

The peaks in $^1$H-NMR are assignable respectively to the positions shown by the numerical values in the following formula (VI):

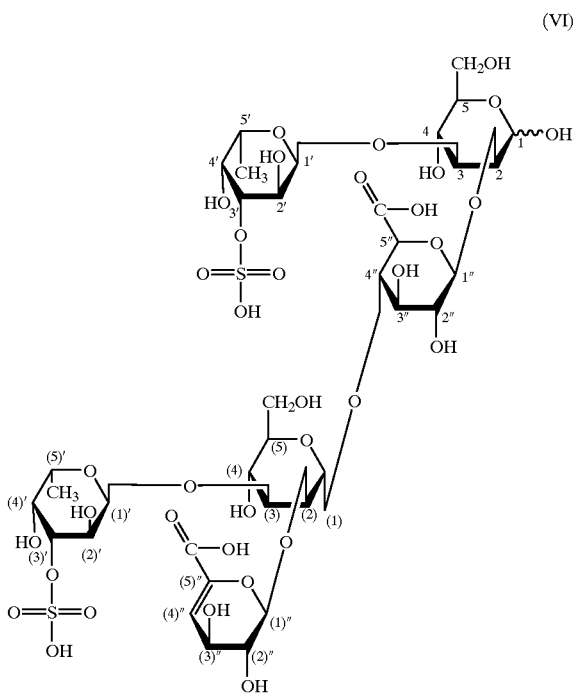
(VI)

When the sulfated-fucose-containing polysaccharide-U thus obtained is treated with the above-mentioned endofucoidanase, elimination occurs as the reaction proceeds and thus the absorbance at 230 nm is increased. All of the main reaction products carry unsaturated hexuronate groups, which suggests that the obtained sulfated-fucose-containing polysaccharide-U has a sugar chain composed of hexuronic acid and mannose alternately bonded to each other. Because of containing fucose as the main constituting saccharide, the obtained sulfated-fucose-containing polysaccharide-U is liable to be degraded with acids, compared with common polysaccharides. On the other hand, it is known that the bonds of hexuronic acids and mannose are relatively highly tolerant to acids. In order to identify the hexuronic acid in the sugar chain which is composed of hexuronic acid and mannose alternately bonded to each other and contained in the sulfated-fucose-containing polysaccharide mixture originating from *Kjellmaniella crassifolia*, the method described in Carbohydrate Research, 125, 283–290 (1984) was used as reference in the following manner. First, the sulfated-fucose-containing polysaccharide mixture is dissolved in 0.3 M oxalic acid and treated at 100° C. for 3 hours. Then it is subjected to molecular weight fractionation and fractions of molecular weight of 3,000 or more are combined. Then it is further treated with an anion exchange resin and the adsorbed matters are collected. The substance thus obtained is freeze-dried and hydrolyzed with 4 N hydrochloric acid. After adjusting the pH value to 8, it is pyridyl-(2)-aminated and uronic acid is analyzed by HPLC. The HPLC is performed under the following conditions:

| | |
|---|---|
| apparatus | Model L-6200 (mfd. by Hitachi, Ltd.); |
| column | PALPAK Type N (4.6 mm × 250 mm, mfd. by Takara Shuzo, Co., Ltd.); |
| eluent | 200 mM acetic acid-triethylamine buffer (pH 7.3): acetonitrile = 25:75; |
| detection | Fluorometric Detector F-1150 (mfd. by Hitachi, Ltd.), excitation wavelength: 320 nm, fluorescent wavelength: 400 nm; |
| flow rate | 0.8 ml/min; |
| column temperature | 40° C. |

As the standards for PA hexuronic acids, use is made of those prepared by pyridyl-(2)-aminated glucuronic acid manufactured by Sigma Chemical Co., galacturonic acid manufactured by Wako Pure Chemical Industries, Ltd., induronic acid obtained by hydrolyzing 4-methylumbelliferyl-α-L-iduronide manufactured by Sigma Chemical Co., and mannuronic acid and guluronic acid obtained by hydrolyzing alginic acid (mfd. by Wako Pure Chemical Industries, Ltd.) followed by the separation with an anion exchange resin with reference to the method described in Acta Chemica Scandinavica, 15, 1397–1398 (1961).

As a result, it is found out that glucuronic acid alone is contained as the hexuronic acid in the sugar chain in the above-mentioned sulfated-fucose-containing polysaccharide mixture.

Further, the glucuronic acid in the hydrolyzate of the above-mentioned sugar chain is separated from D-mannose by using an anion exchange resin and freeze-dried. Then the specific rotation thereof is measured. It is thus clarified that the glucuronic acid is a dextrorotatory one, i.e., D-glucuronic acid.

Further, the sulfated-fucose-containing polysaccharide mixture originating from *Kjellmaniella crassifolia* is treated with the above-mentioned endofucoidanase and then hydrolyzed with the use of oxalic acid similar to the above case. However, no polymer having D-glucuronic acid and D-mannose alternately bonded to each other is found out. Based on these results, it is clarified that the above-mentioned endofucoidanase cleaves via the elimination reaction sulfated-fucose-containing polysaccharides having a skeleton structure composed of D-glucuronic acid and D-mannose alternately bonded to each other.

Further, the polymer obtained by the degradation with oxalic acid is subjected to NMR analysis to thereby examine the anomeric configuration of the binding sites of D-glucuronic acid and D-mannose and the glycoside bond.

The NMR analytical data of the polymer are as follows. The chemical shifts in [1] H-NMR are expressed by taking the chemical shift of the methyl group in triethylamine as 1.13 ppm, while those in $^{13}$C-NMR are expressed by taking the chemical shift of the methyl group in triethylamine as 9.32 ppm.

$^1$H-NMR ($D_2O$); δ 5.25(1H, br-s, 1-H), 4.32(1H, d, J=7.6 Hz, 1'-H), 4.00(1H, br-s, 2-H), 3.71(1H, m, 5'-H), 3.69(H of 1H, m, 5-CH), 3.68(1H, m, 3-H), 3.63(H of 1H, m, 5-CH), 3.63(1H, m, 4'-H), 3.57(1H, m, 4-H), 3.54(1H, m, 3'-H), 3.53(1H, m, 5-H), 3.25(1H, t, J=8.5 Hz, 2'-H).

$^{13}$C-NMR (D$_2$O); δ 175.3 (C of 5'-COOH), 102.5(1'-C), 99.6(1-C), 78.5(2-C), 77.9(4'-C), 77.0(3'-C), 76.7(5'-C), 73.9(5-C), 73.7(2'-C), 70.6(3-C), 67.4(4-C), 61.0(C of 5-CH$_2$OH).

The peaks are assignable respectively to the positions shown by the numerical values in the following formula (VII):

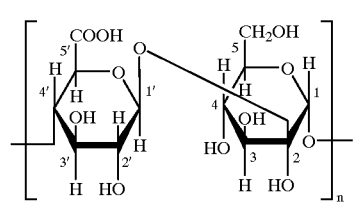

(VII)

Regarding the configuration at the 1-position of the D-glucuronic acid, it is identified as β-D-glucuronic acid because of its vicinal binding constant of 7.6 Hz.

Regarding the configuration at the 1-position of the D-mannose, it is identified as α-D-mannose because of its chemical shift of 5.25 ppm.

The binding manners of the constituting saccharides are analyzed by the HMBC method, i.e., the $^1$H-heteronculear bond detection method. The DQF-COSY and HOHAHA methods are employed in the assignment in $^1$H-NMR while the HSQC method is employed in the assignment in $^{13}$C-NMR.

In the HMBC spectrum, crossed peaks are observed between 1-H and 4'-C with between 4'-H and 1-C, and between 1'-H and 2-C with between 2-H and 1'-C. These facts indicate that D-glucose is bonded to the 2-position of D-mannose via a β-bond while D-mannose is bonded to the 4-position of D-glucuronic acid via an α-bond.

By taking the above-mentioned results together into consideration, it is revealed that the compound (a) has a structure wherein unsaturated D-glucuronic acid and L-fucose having a sulfate group bonded thereto are bonded to D-mannose which is the reducing end; the compound (b) has a structure wherein unsaturated D-glucuronic acid and L-fucose having two sulfate groups bonded thereto are bonded to D-mannose which is the reducing end and has a sulfate group bonded thereto; and the compound (c) has a structure wherein D-glucuronic acid and L-fucose having a sulfate group bonded thereto are bonded to D-mannose which is the reducing end, and to this D-glucuronic acid is bonded D-mannose and, in turn, to this D-mannose are further bonded unsaturated D-glucuronic acid and L-fucose having a sulfate group bonded thereto.

As discussed above, the obtained sulfated-fucose-containing polysaccharide-U has a structure wherein D-glucuronic acid and D-mannose are alternately bonded to each other and L-fucose is bonded to at least one D-mannose.

Also, it has a partial structure represented by the following general formula (VIII) wherein at least one of alcoholic hydroxyl groups has been sulfated and n stands for an integer of 1 or more:

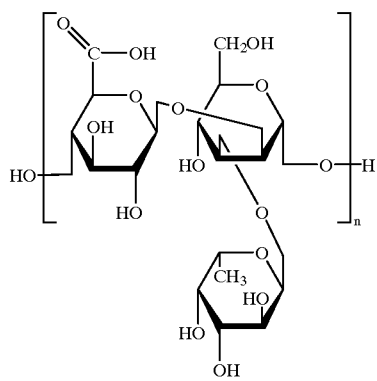

(VIII)

As such, the sulfated-fucose-containing polysaccharide-U, which is separated from the sulfated-fucose-containing polysaccharide-F of the present invention and purified, is provided. The sulfated-fucose-containing polysaccharide-U to be used in the present invention contains uronic acid as its constituting saccharide and is degraded by the fucoidanase produced by Flavobacterium sp. SA-0082 (FERM BP-5402) to thereby give at least one compound selected from those represented by the above formulae (I), (II) and (III). The sulfated-fucose-containing polysaccharide-U to be used in the present invention is not restricted in the molecular weight, molecular weight distribution or saccharide composition. Namely, sulfated-fucose-containing polysaccharide-U having arbitrary molecular weight and molecular weight distribution may be prepared and sulfated-fucose-containing polysaccharides having definitely clarified physicochemical properties can be provided.

When this sulfated-fucose-containing polysaccharide-U is chemically, physically or enzymatically treated, its degraded product can be prepared and the oligosaccharides having, for example, the above formulae (I), (II) and (III) may be used in the present invention as well.

The sulfated-fucose-containing polysaccharide(s) and/or degradation product(s) thereof used in the present invention have/has high affinity to virus and, when such sulfated-fucose-containing polysaccharide(s) and/or degradation product(s) thereof are/is utilized as a carrier for adsorption of virus, purification and removal of virus can be easily and conveniently conducted.

A carrier for adsorption of virus which contains sulfated-fucose-containing polysaccharide(s) and/or degradation product(s) thereof may be anything so far as it contains an effective amount of the sulfated-fucose-containing polysaccharide(s) and/or degradation product(s) thereof and any virus-adsorbing carrier may be prepared depending upon the particular object.

Removal or purification of virus can be conducted easily and conveniently when the virus-adsorbing carrier is contacted with a sample containing virus so that desired virus is adsorbed with the sulfated-fucose-containing polysaccharide(s) and/or degradation product(s) thereof and then the sulfated-fucose-containing polysaccharide(s) and/or degradation product(s) thereof are/is selectively fractionated. In fractionating the sulfated-fucose-containing polysaccharide(s) and/or degradation product(s) thereof after absorbing the virus, the above-mentioned fractionating method for the sulfated-fucose-containing polysaccharide(s) and/or degradation product(s) thereof may be used for example. As a result of fractionation of the sulfated-fucose-containing polysaccharides and degradation products from the sample as such, removal of virus from the sample is achieved. When purification of virus is an object, the adsorbed virus is eluted and recovered by an appropriate method from the fractionated sulfated-fucose-containing polysaccharide(s) and/or degradation product(s) thereof.

Incidentally, the carrier for adsorption of virus according to the present invention may be a suitably modified sulfated-fucose-containing polysaccharide(s) and/or degradation product(s) thereof which is suitably modified. For example, when a carrier where avidin is immobilized is used in case a virus-adsorbing carrier containing biotin-bonded sulfated-fucose-containing polysaccharide(s) and/or degradation product(s) thereof are/is used, then the virus-adsorbed sulfated-fucose-containing polysaccharide(s) and/or degradation product(s) thereof can be recovered on an avidin-immobilized carrier. In modifying the sulfated-fucose-containing polysaccharide(s) and/or degradation product(s) thereof, known chemical or enzymatic modifying method may be used.

On the other hand, a carrier for adsorption of virus can be prepared by immobilizing the sulfated-fucose-containing polysaccharide(s) and/or degradation product(s) thereof on a carrier. The carrier for adsorption of virus prepared by the use of insoluble carrier can be used for purification and removal of virus in liquid sample, air, etc. without a special fractionating operation.

There is no particular limitation for the carrier used for immobilization of sulfated-fucose-containing polysaccharide(s) and/or degradation product(s) thereof and, for example, carrier in a form of gel or particles may be used. As to the carrier in a form of particles, porous one where surface area of the particle is big is suitable. A support in a form of thin film or hollow fiber may be used as a carrier for immobilization. Materials of the carrier used for immobilization may be suitably selected, depending upon the object and method of use, from polysaccharides such as agarose, cellulose and dextran, synthetic polymers such as polyacrylamide, acrylic acid polymer, styrene-divinylbenzene polymer and polymethacrylate, and inorganic polymers such as silica gel and glass.

Immobilization of sulfated-fucose-containing polysaccharide(s) and/or degradation product(s) thereof may be conducted by a common method [refer, for example, to "Shin Seikagaku Jikken Koza—Tampakushitsu I(New Biochemical Experiment Practice—Protein I)" 227–237 (1990); published by Tokyo Kagaku Dojin] depending upon the type of the carrier used and, when polysaccharide gel, for example, is used as a carrier for immobilization, it is conducted by such a manner that the introducing group of the polysaccharide gel is subjected to a covalent bond to a functional group of the sulfated-fucose-containing polysaccharide(s) and/or degradation product(s) thereof.

In immobilization of the sulfated-fucose-containing polysaccharide(s) and/or degradation product(s) thereof in polysaccharide gel, it is necessary to select a polysaccharide gel having an introducing group which is suitable for binding to a functional group in sulfated-fucose-containing polysaccharide(s) and/or degradation product(s) thereof. For example, when a carboxyl group existing in sulfated-fucose-containing polysaccharide(s) and/or degradation product(s) thereof is utilized, a polysaccharide gel having ω-aminoalkyl group or thiol group is used or, when a hydroxyl group is utilized, a polysaccharide gel having epoxy group is used where an immobilization can be conducted. When a polysaccharide gel has no appropriate introducing group, it may be used for immobilization after adding a suitable introducing group thereto.

The virus-adsorbing carrier where the sulfated-fucose-containing polysaccharide(s) and/or degradation product(s) thereof are/is immobilized to the carrier by means of covalent bond as such is stable both physically and chemically and, during the adsorption of virus and/or during the elution of virus, detachment of the sulfated-fucose-containing polysaccharide(s) and/or degradation product(s) thereof into the sample is not observed. Therefore, said carrier can be well used for the manufacture of, for example, pharmaceuticals without difficulty.

Purification or removal of virus can be conducted using a virus-adsorbing carrier containing the sulfated-fucose-containing polysaccharide(s) and/or degradation product(s) thereof prepared as mentioned above. Examples of the virus-containing sample applicable to the method of the present invention are supernatant fluid of cultured cells infected by virus or disrupted cells thereof, substances in living body such as blood and serum, pharmaceutical agent, and liquid sample such as drinking water. It is also possible to remove the virus floating in gas such as air by the method of the present invention.

The virus-adsorbing carrier of the present invention has a binding ability to various viruses and it is possible to purify or remove viruses such as retrovirus, adenovirus, adeno-associated virus (AAV), influenza virus, herpes virus and baculovirus by the method of the present invention.

As such, the virus-adsorbing carrier containing the sulfated-fucose-containing polysaccharide(s) and/or degradation product(s) thereof according to the present invention is useful as a carrier for removal or for purification of virus.

The method of the present invention is useful as a process for purification of virus and it achieves an effect when highly pure virus is needed as an object of research or for the manufacture of vaccine. In the case of a sample where concentration of virus is low, this method is important as a means for concentrating the virus. In addition, when contamination with virus is not desirable such as in the case of pharmaceuticals or reagents for research such as a medium used for the culture of cells, the method of the present invention can be utilized for removing the virus. Further, in detecting the virus, sensitivity of the detection can be improved by combining with a concentrating operation of virus utilizing the method of the present invention.

In the detection of virus in a sample, the biggest factor for deciding the sensitivity is the concentration of virus in the sample. When the present invention is utilized, detection of virus in higher sensitivity as compared with the conventional methods is possible. Thus, after the virus to be detected in a sample is caught on a virus-adsorbing carrier of the present invention, the carrier itself is or, after the virus on the carrier is recovered by means of an suitable operation, it is subjected to a detecting operation for virus whereby virus can be detected in a high sensitivity. There is no particular limitation for the sample wherefrom virus is detected and, in addition to samples derived from living body such as tissues, blood and urine, various samples such as pharmaceuticals, food, drinking water, drained water, air or others in natural environments may be subjected to the method of the present invention. Moreover, there is no particular limitation for the method of detection of virus and a method where an antibody which recognizes the virus to be detected is a method where nucleic acid in the virus is detected, etc. may be appropriately selected and used. For example, after gargling with a solution containing the virus-adsorbing carrier of the present invention, the virus-adsorbed carrier is recovered from the gargled liquid and then said carrier itself or virus sample eluted and concentrated from the carrier is used for the virus detecting operation whereupon the presence/absence and the amount of the virus in mouth can be checked.

Purification of virus, e.g. purification of virus in a liquid sample by a column chromatography using a virus-adsorbing carrier prepared by immobilizing the sulfated-fucose-containing polysaccharide(s) and/or degradation product(s) thereof in polysaccharide gel, may be conducted as follows. First, a column filled with the above carrier is prepared and then the column is equilibrated with a suitable initiation buffer. Then the sample containing the virus is loaded in the above column and the substances which are not adsorbed are washed out using an initiation buffer or the like. If necessary, the column is washed by changing the composition of the buffer under the condition where the adsorbed virus is not eluted whereby the adsorbed things other than virus can be reduced. After that, a suitable eluting operation such as the use of buffer containing high concentration of salt is conducted to recover the virus in an eluate. Virus-adsorbing carrier in a form of gel or particles can be used in other methods than the above column chromatography such as purification by a batch method. In addition, the virus-adsorbing carrier prepared from a support in the form of thin film or hollow fiber can be used by a method suitable for each of the carriers such as after attaching to a suitable device.

The method for the purification of virus according to the present invention makes purification and removal of virus in a simple and easy manner and also under the state near the physiological condition.

As conventional methods for purification of virus, a precipitating method using polyethylene glycol or ammonium sulfate is available but, in said method, lowering of infecting ability of virus is a big problem and, especially in hemorrhagic fever with renal syndrome (HFRS) virus, infecting ability is entirely lost. Methods for purification of virus by means of ultracentrifugation or ultrafilter have been known as well but operations are complicated in said methods and it is unavoidable that infecting ability is lost to some extent. In the method of the present invention however, purification and concentration of virus are possible without inactivation of the virus in the sample and this method is useful in the manufacture of and in conducting investigations of virus.

As to a carrier for chromatography applicable to purification of virus, sulfated cellulose has been known to be applicable for purification of Japanese encephalitis virus (Japanese Examined Patent Publication No. 33879/1987), influenza virus (Japanese Examined Patent Publication No. 30752/1987), hydrophobia virus (Japanese Examined Patent Publication No. 30753/1987), retrovirus (U.S. Pat. No. 5,447,859), adeno-associated virus [Human Gene Therapy, 7, 507–513, (1996)], etc. However, as shown in the following example, the virus-adsorbing carrier has a high virus-adsorbing capacity as compared with sulfate cellulose. Moreover, when the adsorbed amount of retrovirus per sulfate group existing on the carrier is compared, the virus-adsorbing carrier of the present invention is better than the sulfate cellulose. Accordingly, when the virus-adsorbing carrier of the present invention is used, it is now possible to conduct purification, concentration or removal of virus more efficiently. Further, although adenovirus is not adsorbed with sulfate cellulose [Bio/Technology, 11, 173–178, (1993)], the virus-adsorbing carrier of the present invention exhibits an adsorbing ability even to adenovirus and can be applied to virus species of broader ranges.

In addition, when the virus-adsorbing carrier of the present invention is used, contaminated virus can be removed without deteriorating the effective components in the sample whereby said carrier is useful especially in the manufacture of pharmaceuticals.

EXAMPLES

The present invention will be further illustrated by way of the following examples although the present invention is never limited by these examples.

Referential Example 1

Extraction of Sulfated-Fucose-Containing Polysaccharide Mixture of *Kjellmaniella carssifolia:*

2 kg of thoroughly dried *Kjellmaniella crassifolia* was ground with a free mill (mfd. by Nara Kikai Seisakusho). The dry powder thus obtained was suspended in 9 l of 80% ethanol and treated at 80° C. for 2 hours. Then the mixture was filtered through a filter paper to thereby give the residue. This residue was repeatedly washed with ethanol and filtered thrice in the same manner as described above to thereby give the residue after ethanol-washing. This residue was suspended in 36 l of a 0.2 M solution of calcium acetate, treated at 95° C. for 2 hours and filtered. The residue was washed with 4 l of a 0.2 M solution of calcium acetate to thereby give 36 l of an extract containing the sulfated-fucose-containing polysaccharides of *Kjellmaniella carssifolia.*

Referential Example 2

Purification of Sulfated-Fucose-Containing Polysaccharide Mixture of *Kjellmaniella carssifolia:*

To the filtrate obtained in Referential Example 1 was added 5% cetylpyridinium chloride until no precipitates were formed any more. Then the precipitates were collected by centrifugation and suspended in 3 l of a 0.4 M aqueous solution of sodium chloride followed by centrifugation and washing. After repeating this washing procedure thrice, 1 l of 4 M aqueous solution of sodium chloride was added to the precipitate and the mixture was well stirred. Then ethanol was added thereto so as to give a concentration of 80% and the mixture was stirred and centrifuged to thereby give the precipitate. The obtained precipitate was suspended in 80% ethanol and centrifuged. These procedures were repeated until the absorbance of the supernatant at 260 nm reached 0. The precipitate was dissolved in 3 l of a 2 M aqueous solution of sodium chloride. After removing the insoluble matters by centrifugation, 100 ml of DEAE-Cellulofine A-800 (mfd. by Seikagaku Kogyo) equilibrated with a 2 M aqueous solution of sodium chloride was added thereto and stirred. Next, the resin added above was removed by filtration. The filtrate was fed into a DEAE-Cellulofine A-800 column equilibrated with a 2 M aqueous solution of sodium chloride and the unadsorbed fraction was subjected to ultrafiltration by using an ultrafilter provided with a hollow fiber of exclusion molecular weight of 100,000 or less to thereby completely eliminate the coloring matters and sodium chloride. Next, the insoluble matters were eliminated by centrifugation and filtration followed by freeze-drying. The freeze-dried sulfated-fucose-containing polysaccharide mixture weighed 90 g.

Referential Example 3
Method for Production of Sulfated-Fucose-Containing Polysaccharide-F:

1.2 g of the sulfated-fucose-containing polysaccharide mixture obtained in Referential Example 2 was weighed out and dissolved in a 1.5 M solution of sodium chloride in such a manner as to give a final concentration of 0.2%. Next, 1.25% of cetylpyridinium chloride in a 1.5 M sodium chloride solution was added thereto until no precipitates were formed any more. Then the precipitates were collected by centrifugation and suspended in 500 ml of a 1.5 M aqueous solution of sodium chloride followed by centrifugation and washing. After repeating this washing procedure thrice, 1 l of a 4 M aqueous solution of sodium chloride was added to the precipitate and the mixture was well stirred. Then ethanol was added thereto so as to give a concentration of 80% and the mixture was stirred and centrifuged to thereby give the precipitate. The obtained precipitate was suspended in 80% ethanol and centrifuged. These procedures were repeated until the absorbance of the supernatant at 260 nm reached 0. The precipitate was dissolved in 500 ml of a 2 M aqueous solution of sodium chloride. After removing the insoluble matters by centrifugation, 1 ml of DEAE-Cellulofine A-800 (mfd. by Seikagaku Kogyo) equilibrated with a 2 M aqueous solution of sodium chloride was added thereto and stirred. Next, the resin added above was removed by filtration. The filtrate was fed into a DEAE-Cellulofine A-800 column equilibrated with a 2 M aqueous solution of sodium chloride and the unadsorbed fraction was subjected to ultrafiltration by using an ultrafilter provided with a hollow fiber of exclusion molecular weight of 100,000 or less to thereby completely eliminate the coloring matters and sodium chloride. Next, the insoluble matters were eliminated by centrifugation followed by ultrafiltration and freeze-drying. The freeze-dried sulfated-fucose-containing polysaccharide-F weighed 710 mg.

Referential Example 4
Method for Incubative Purification of Sulfated-Fucose-Containing Polysaccharide-F:

The sulfated-fucose-containing polysaccharide mixture obtained in Referential Example 2 is a mixture of two types of sulfated-fucose-containing polysaccharides. 60 g of this mixture was weighed out and dissolved in 20 l of artificial seawater. Next, 200 g of peptone and 4 g of yeast extract were added thereto. After feeding into a 30 l jar fermenter and sterilizing, it was inoculated with the above-mentioned Flavobacterium sp. SA-0082 (FERM BP-5402), described in WO96/34004, which was then incubated at 25° C. for 24 hours. After centrifuging to thereby eliminate the cells, the culture medium was ultrafiltered with an ultrafilter provided with a hollow fiber of exclusion molecular weight of 100,000 or less. After completely removing low-molecular weight substances, the insoluble matters were eliminated by centrifugation and filtration followed by freeze-drying. The freeze-dried sulfated-fucose-containing polysaccharide-F weighed 36 g.

Referential Example 5
Fractional Purification of Sulfated-fucose-containing Polysaccharide-U and Sulfated-Fucose-Containing Polysaccharide-F:

The freeze-dried sulfated-fucose-containing polysaccharide mixture (7 g) mentioned in Referential Example 2 was weighed and dissolved in 0.2 M calcium chloride. Then, the solution was treated with a column of 4,000 ml of DEAE-Sepharose FF (mfd. by Pharmacia) equilibrated with 0.2 M calcium chloride, well washed with 0.2 M calcium chloride and eluted with sodium chloride with a gradient of 0 to 4 M. Among the eluted fractions, those where sodium chloride concentrations were 0.05 to 0.8 M were collected, desalted by means of dialysis and freeze-dried to give 2.1 g of sulfated-fucose-containing polysaccharide-U which was separated from sulfated-fucose-containing polysaccharide-F.

Further, among the above eluted fraction, those where sodium chloride concentrations were 0.9 to 1.5 M were collected, desalted by means of dialysis and freeze-dried to give 4.7 g of sulfated-fucose-containing polysaccharide-F which was separated from sulfated-fucose-containing polysaccharide-F.

Referential Example 6

2 kg of thoroughly dried *Kjellmaniella crassifolia* was ground with a free mill (mfd. by Nara Kikai Seisakusho). The dry powder thus obtained was suspended in 9 l of 80% ethanol and treated at 80° C. for 2 hours. Then the mixture was filtered through a filter paper to thereby give the residue. This residue was repeatedly washed with ethanol and filtered thrice in the same manner as described above to thereby give the residue after ethanol-washing. This residue was suspended in 36 l of a 0.2 M solution of calcium acetate, treated at 95° C. for 2 hours and filtered. The residue was washed with 4 l of a 0.2 M solution of calcium acetate to thereby give 36 l of an extract containing the sulfated-fucose-containing polysaccharides of *Kjellmaniella carssifolia*.

This filtrate was concentrated to 2 l with the use of an ulterfilter provided with an ultrafiltration membrane of exclusion molecular weight of 100,000. Next, sodium chloride was added thereto so as to give a final concentration of 1.5 M. Further, 5% cetylpyridinium chloride was added thereto until no precipitates were formed any more. Then the precipitates were removed by centrifugation and the supernatant thus obtained was concentrated to 1 l by ultrafiltration. After adding 4 l of ethanol, the precipitates thus formed were collected by centrifugation. To this precipitate was added 100 ml of a 4 M aqueous solution of sodium chloride followed by stirring well. Then ethanol was added thereto to give a concentration of 80% and the mixture was stirred and centrifuged. The obtained precipitate was suspended in 80% ethanol and centrifuged. These procedures were repeated until the absorbance of the supernatant at 260 nm reached 0. The precipitate was dissolved in 2 l of a 2 M aqueous solution of sodium chloride. After removing the insoluble matters by centrifugation, 50 ml of DEAE-Cellulofine A-800 (mfd. by Seikagaku Kogyo) equilibrated with a 2 M aqueous solution of sodium chloride was added thereto and stirred. Next, the resin added above was removed by filtration. The filtrate was fed into a DEAE-Cellulofine A-800 column equilibrated with a 2 M aqueous solution of sodium chloride and the unadsorbed fraction was subjected to ultrafiltration by using an ultrafilter provided with a hollow fiber of exclusion molecular weight of 100,000 or less to thereby completely eliminate the coloring matters and sodium chloride. Next, the insoluble matters were eliminated by centrifugation and filtration followed by freeze-drying. The freeze-dried sulfated-fucose-containing polysaccharide-U weighed 15 g.

When treated with the above-mentioned endofucoidanase, this sulfated-fucose-containing polysaccharide-U was degraded to thereby give the oligosaccharides represented by the above formulae (I), (II) and (III).

Example 1
Preparation of FF-Cellulofine:

The sulfated-fucose-containing polysaccharide-F (840 mg) mentioned in Referential Example 3 was added to 80 ml of a reaction solution (0.2 M phosphate buffer, pH 7.0, 0.01 M NaCl) containing 500 mg of NaCNBH$_4$ together with 50 g (wet weight) of Aminocellulofine (Seikagaku Corporation) and a condensation reaction was conducted at 60° C. for 60 hours. The resulting reaction product was washed with pure water, 80 ml of a reaction solution (0.2 M phosphate buffer, pH 7.0, 0.1 M NaCl) containing 420 mg of glucose and 210 mg of NaCNBH$_4$ was added thereto and a condensation reaction was conducted at 60° C. for 60 hours. The resulting reaction product was washed with 3 M NaCl and then with pure water. Hereinafter, this reaction product will be referred to as FF-Cellulofine.

The above FF-Cellulofine contained 33 $\mu$mol/ml of sulfate group.

Example 2
(1) Preparation of Supernatant Liquid of Virus:

The supernatant liquid containing recombinant retrovirus derived from mouse leukemia virus was prepared as follows. GP+E86 productive cells (ATCC CRL-9642) containing retrovirus plasmid PM5neo vector [Experimental Hematology, 23, 630–638, (1995)] were incubated in a Dulbecco-modified Eagle's medium (DMEM; mfd. by JRH Bioscience) containing 10% of fetal calf serum (FCS; mfd. by Gibco), 50 units/ml of penicillin and 50 $\mu$g/ml of streptomycin (both mfd. by Gibco). All of the DMEM used in Examples 2 to 4 contained 50 units/ml of penicillin and 50 $\mu$g/ml of streptomycin. Virus-containing supernatant liquid was prepared by adding the DMEM containing 10% of FCS to a plate where the above-produced cells were grown semiconfluently and by incubating overnight followed by collecting the supernatant liquid therefrom. The collected supernatant liquid of the medium was filtered through a filter of 0.45 $\mu$m (mfd. by Millipore) to give a supernatant liquid of retrovirus and it was stored at −80° C. until use.

Titer of the virus was measured by a standard method [Journal of Virology, 62, 1120–1124, (1988)] using NIH/3T3 cells (ATCC CRL-1658). Thus, DMEM containing 2,000 NIH/3T3 cells was added per well of a six-well tissue culture plate, incubation was conducted for one night and then sequentially-diluted supernatant liquid of virus and hexadimethrine bromide (Polybrene; Aldrich) with a final concentration of 7.5 $\mu$g/ml were added to each of the wells. This was incubated at 37° C. for 24 hours and then the medium was exchanged with that containing G418 (final concentration being 0.75 mg/ml; mfd. by Gibco) followed by continuing the incubation. The grown colonies of G418-resistant (G418$^r$) colonies after 10 to 12 days were dyed with Crystal Violet and the numbers were recorded. Based upon the colony numbers in each well and the rate of dilution of the supernatant liquid of virus added thereto, numbers of the infectious particles (cfu/ml) were counted and the titer was determined.

(2) Purification of Retrovirus Using FF-Cellulofine:

FF-Cellulofine (3 ml) prepared in Example 2 was deaerated and filled in a disposable column (Sepacol Mini; mfd. by Seikagaku Kogyo) to prepare a column having a bed volume of 3 ml. The column was well equilibrated with PBS (phosphate-buffered saline solution) and then 3 ml of the supernatant liquid of the retrovirus prepared in Example 1 was applied to the column. After that, the column was washed with 30 ml of PBS and successively treated with 15 ml of eluting buffer A (PBS containing 360 mM of NaCl), 15 ml of eluting buffer B (PBS containing 860 mM of NaCl) and 15 ml of eluting buffer C (PBS containing 1860 mM NaCl) to elute the adsorbed substances. Each 3 ml of the eluate from the column was fractionally collected including that upon application of the supernatant liquid of the virus.

Absorbances of the fractionally collected eluates were measured at 280 nm and, at the same time, amounts of the virus contained therein were determined. In determining the amount of the virus, a method for the measurement of titer of virus mentioned in Example 1 was used. From the fractionated eluates was taken 200 $\mu$l and to this were added 800 $\mu$l of DMEM and hexadimethrine bromide (final concentration being 7.5 $\mu$g/ml). This was used as a substitute for the sequentially diluted supernatant of the virus and the same operation as before was conducted to check the numbers of the G418 resistant colonies appeared thereby.

The result is shown in FIG. 1. Most of the substances having an absorption at 280 nm contained in the supernatant liquid of the virus were eluted immediately after addition to the column while most of the virus was eluted at the stage when elution was conducted using an eluting buffer A. This shows that virus is specifically adsorbed with FF-Cellulofine column and, as a result thereof, virus can be separated from many contaminants in the sample.

(3) Comparison of Adsorbing Ability of Retrovirus by FF-Cellulofine and Sulfated Cellulofine:

Comparison of the properties of FF-Cellulofine and sulfated cellulose was conducted by the operation as mentioned below. Sulfated Cellulofine (mfd. by Seikagaku Kogyo) was used as a sulfated cellulose. This sulfated Cellulofine had 8 µmol/ml of sulfate group.

Figure 2:
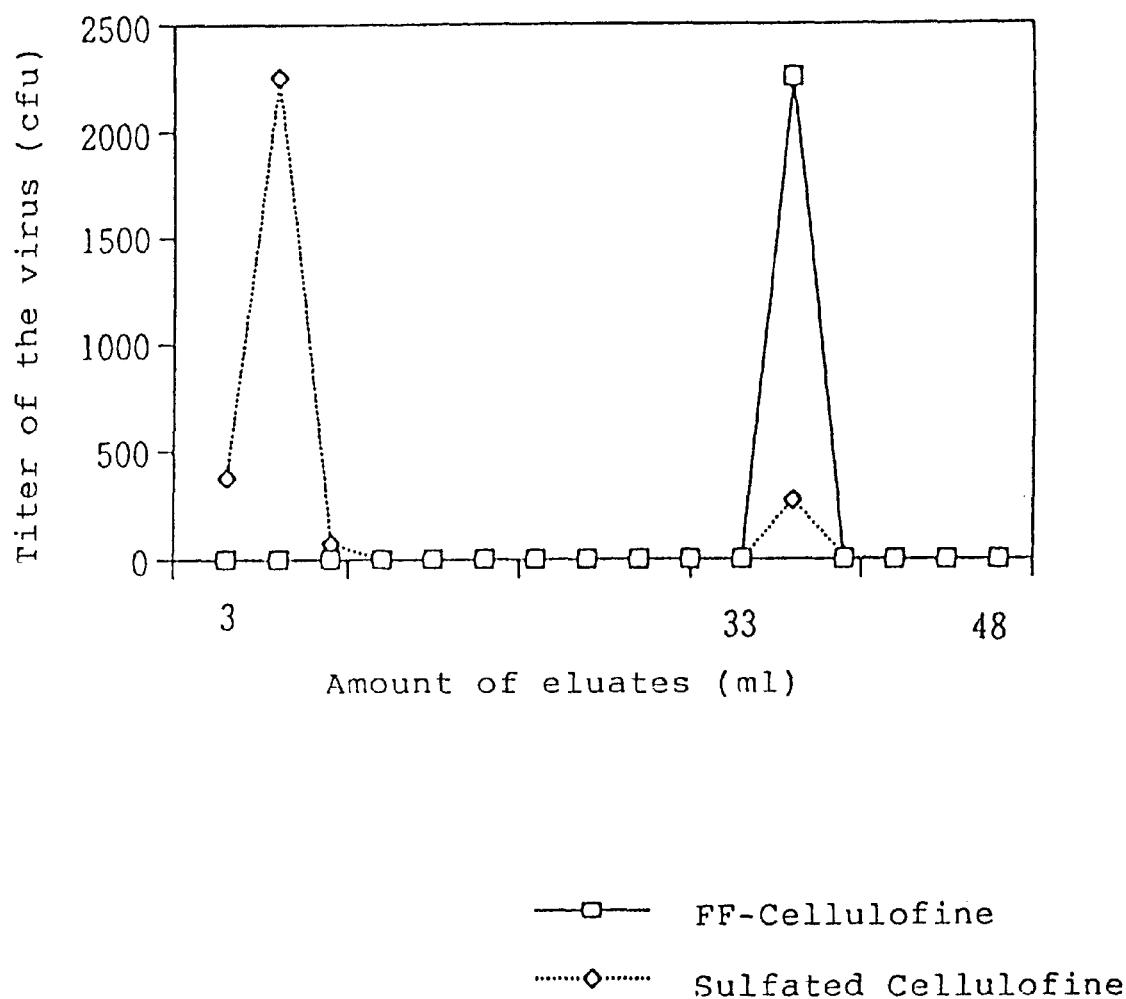
FIG. 2 shows a comparison of the retrovirus-adsorbing ability of FF-Cellulofine with that of sulfated Cellulofine.

Retrovirus as mentioned in Example 2-(2) was purified using each of FF-Cellulofine and sulfated Cellulofine. Eluting operations using an eluting buffers B and C were omitted. The result is shown in FIG. 2. When FF-Cellulofine column was used, no virus was detected in an unadsorbed fraction (just passed-through fraction and an eluted fraction upon washing with a PBS) while, in sulfated Cellulofine, leakage of virus was noted in this fraction. Amount of virus recovered by the eluting buffer A after being adsorbed with the column and the recovered amount of virus per sulfate group present in both carriers are shown in Table 1. The data by FF-Cellulofine was better than those by sulfated Cellulofine in the comparison of both of the total recovered amount of virus and the recovered amount of virus per sulfate group. This means that FF-Cellulofine exhibits higher retrovirus-adsorbing capacity than sulfated Cellulofine.

TABLE 1

| Carrier: | FF-Cellulofine | Sulfated Cellulofine |
|---|---|---|
| Amount of recovered virus | 2250 cfu | 185 cfu |
| Amount of recovered virus per sulfate group | 22.7 cfu/µ mol | 11.9 cfu/µ mol |

Example 3

(1) Preparation of Recombinant Adeno-Associated Virus:

Recombinant adeno-associated virus containing lacZ gene of Escherichia coli as a reporter gene was prepared in accordance with the operations as mentioned below. There are two XbaI sites derived from vector (pA11P) in a plasmid pAV1 containing a full length of adeno-associated virus (AAV) [ATCC No. 37215; cf. Gene, 23, 65–73, (1983)]. First, in order to remove them, pAV1 was digested with XbaI (mfd. by Takara Shuzo Co., Ltd.), the end was made blunt using a DNA blunting kit (mfd. by Takara Shuzo Co., Ltd.) and self-ligation was conducted using a ligation kit (mfd. by Takara Shuzo Co., Ltd.). XbaI linker was introduced into the resulting recombinant plasmid (wherefrom XbaI-XbaI small fragments derived from pA11P were removed) so that the domain coding for the protein on AAV genome and the terminal sequence are easily separated. Thus, the above plasmid was partly digested with NcoI (mfd. by Takara Shuzo Co., Ltd.) and mixed with XbaI linker having a base sequence as shown in SEQ ID NO:1 in the Sequence Listing to conduct a ligation. Among the resulting plasmids, that wherein the above-mentioned linker was inserted into an NcoI site existing in a position of 4481st base from the 5'-end of the AAV genome was selected, and this plasmid was further subjected to a partial digestion with AvaII (mfd. by Takara Shuzo Co., Ltd.) and mixed with XbaI linker consisting of oligonucleotide having a base sequence as shown in SEQ ID NO:2 and NO:3 in the Sequence Listing to conduct a ligation. Among the plasmids prepared as such, that where the above-mentioned linker was inserted into an AvaII site existing at the position of 190th base from the 5'-end of the AAV genome was selected. The plasmid prepared as such wherein two new XbaI sites were inserted was named pAV1x.

The plasmid pAV1x was digested with XbaI and subjected to an agarose gel electrophoresis to recover each of a DNA fragment of about 4.3 kb containing a domain coding for the protein derived from AAV genome and another DNA fragment of about 4.4 kb containing an AAV terminal sequence from the gel.

Plasmid vector pCMVβ (mfd. by Clontech) was digested with EcoRI and HindIII (both mfd. by Takara Shuzo Co., Ltd.) and subjected to an agarose gel electrophoresis to recover an DNA fragment of about 4.5 kb containing SV40 polyA signal, *E. coli* lacZ gene and CMV (cytomegalovirus) immediate early promoter. Each of the ends of said fragment and the DNA fragment of about 4.4 kb derived from the above plasmid pAV1x was blunted using a DNA blunting kit and then they were mixed to conduct a ligation whereupon a recombinant plasmid was prepared. Said plasmid was named AAV vector plasmid.

Meanwhile, plasmid vector pUC18 (mfd. by Takara Shuzo Co., Ltd.) was digested with XbaI and mixed with the above DNA fragment of about 4.3 kb derived from plasmid pAV1x to conduct a ligation whereupon a recombinant plasmid was prepared. Said plasmid was named AAV helper plasmid.

(2) Preparation of Supernatant Liquid of Adeno-Associated Virus:

AAV vector plasmid and AAV helper plasmid were introduced into 293-cells (ATCC CRL-1573) infected with human adenovirus type 5 (ATCC VR-5) by means of a calcium phosphate method. The cells were incubated for 2–3 days in DMEM containing 10% of FCS and centrifuged to recover the supernatant liquid. The supernatant liquid was filtered through a filter of 0.45 µm (mfd. by Millipore), heated at 56° C. for 30 minutes to inactivate the contaminating adenovirus and was used in the following experiments as a supernatant liquid of adeno-associated virus.

Titer of virus of the supernatant liquid of adeno-associated virus was measured by the following operations. A collagen-coated 24-well plate (mfd. by Iwaki Glass) was used and incubation was conducted after adding 15,000 of 293-cells and DMEM containing 10% of FCS to each well. On the next day, the medium was removed, 0.5 ml of DMEM containing 10% of FCS and 0.1 ml of sequentially-diluted supernatant liquid of virus were newly added and incubation was conducted at 37° C. for one night. The medium was removed from the plate, washed with PBS and allowed to stand at room temperature for 30 minutes after adding 0.5% of glutaraldehyde solution to fix the cells. The plate was washed with PBS and allowed to stand at 37° C. for one night with an X-Gal solution (0.04% of X-Gal, 5 mM of $K_3Fe(CN)_6$, 5 mM of $K_4Fe(CN)_6$ and 1mM of $MgCl_2$). Numbers of the cells dyed in blue due to the activity of β-galactosidase coded on lacZ gene were counted under a microscope and, based upon said numbers and the diluting rate of supernatant liquid of virus added to the well, numbers of the infected particles contained per ml of the supernatant liquid (pfu/ml) were calculated and defined as the titer of the supernatant liquid.

(3) Purification of Adeno-Associated Virus Using FF-Cellulofine and Sulfated Cellulofine:

FF-Cellulofine and sulfated Cellulofine were deaerated and each of them was filled in a disposable column (Sepacol Mini) to prepare a column having a bed volume of 0.5 ml. The column was well equilibrated with PBS (phosphate-buffered saline solution) and each 30 ml of supernatant liquids of the above adeno-associated virus was applied. Then the column was washed with 9 ml of PBS and 9 ml of an eluting buffer A (PBS containing 360 mM of NaCl), 9 ml of an eluting buffer B (PBS containing 860 mM of NaCl) and 9 ml of an eluting buffer C (PBS containing 1860 mM of NaCl) were successively added to elute the adsorbed substances. At that time, each 3 ml of the eluates by the eluting buffers A to C was collected.

Amount of the virus contained in the eluate was determined by a method of measuring the titer of adeno-associated virus as mentioned in Example 3-(2). Incidentally, dilution of each of the eluates was not conducted. In both eluates with FF-Cellulofine and sulfated Cellulofine, virus was present only in the first fraction of the eluate with the eluting buffer A and numbers of the infected cells in said fraction were 126 and 33 in the case of FF-Cellulofine and sulfated Cellulofine, respectively. From this result, it is clear that, as compared with sulfated Cellulofine, FF-Cellulofine has a high adsorbing capacity to adeno-associated virus.

Example 4

(1) Preparation of Supernatant Liquid of Adenovirus:

Supernatant liquid containing human adenovirus type 5 was prepared as follows. Thus, the 293 cell (ATCC CRL-1573) incubated to an extent of 50 to 70% confluence in DMEM containing 5% of FCS was infected with human adenovirus type 5 (ATCC VR-5) and incubated for 2 to 3 days with DMEM containing 1% of FCS to produce virus particles. After completion of the incubation, the recovered 293 cell were disintegrated by subjecting to three cycles of freezing and melting and then centrifuged to recover the supernatant liquid. The resulting supernatant liquid was named a supernatant liquid of adnovirus and stored at −80° C. until use.

Titer of the virus in the supernatant liquid of adenovirus was measured by means of a plaque assay using the 293 cell. Thus, a 24-well tissue culture plate was used and incubation was conducted for two days after adding 20,000 (per well) of the 293 cell and DMEM containing 5% of FCS thereto. After the wells were washed with DMEM containing 1% of FCS, 100 $\mu$l of supernatant liquid of virus which was sequentially diluted with DMEM containing 1% of FCS was added, incubation was conducted at 37° C. for 1.5 hours to effect the infection and incubation was further conducted by addition of 1 ml/well of DMEM containing 1% of FCS. After conducting the incubation for 3 to 5 days, numbers of the plaques per well were counted under a microscope and, based upon the diluting rate of the supernatant liquid of virus added to the wells, numbers of infected particles contained in 1 ml of the supernatant liquid (pfu/ml) were counted and used as a titer for the supernatant liquid. The supernatant liquid of adenovirus used in the present invention had a titer of $2.4 \times 10^9$ pfu/ml.

(2) Adsorption of Adenovirus with FF-Cellulofine:

FF-Cellulofine column was prepared by the same method as in Example 2-(2). The above-mentioned supernatant liquid of adenovirus was diluted with PBS to make $1 \times 10^5$ pfu/ml and 1 ml thereof was applied to the column. Then the column was washed with 30 ml of PBS and then the substances adsorbed with the column were successively eluted with 15 ml of an eluting buffer 1 (PBS containing 860 mM of NaCl) and 15 ml of an eluting buffer 2 (PBS containing 1,500 mM of NaCl.

The eluates from the column was divided into fractions of 3 ml each and the numbers of virus particles in each of them were counted by a method mentioned in Example 4-(1). The result was that the unadsorbed fractions (just passed-through fraction and the eluted fraction by washing with PBS) contained $1 \times 10^4$ pfu of virus particles whereby it was found that 90% of the applied adenovirus was adsorbed with the column. Eluted fractions with the eluting buffers 1 and 2 contained $2 \times 10^4$ pfu and $3 \times 10^3$ pfu of virus particles, respectively.

On the other hand, a column was prepared using sulfated Cellulofine instead of FF-Cellulofine and the above-mentioned operations of adsorption and elution of virus were conducted. In that case, nearly all of the applied virus was recovered in the unadsorbed fraction and no adsorption of the adenovirus with sulfated Cellulofine was noted.

Example 5

(1) Adsorption of Baculovirus with FF-Cellulofine:

Adsorption of Autographa carifornia multinucleocapsid nuclear polyhedrosis virus (AcMNPV) with the virus-adsorbing carrier of the present invention was investigated. Fundamental handling operations of the virus were conducted according to a method mentioned in "Baculovirus Expression Vector" by O'Reilly et al., published by W. H. Freeman & Co., 1992.

FF-Cellulofine column of a bed volume of 2 ml was prepared by a method mentioned in Example 2-(2) and the column was equilibrated with 30 ml of PBS. High-titer stock of AcMNPV of a wild type (mfd. by Invitrogen) was diluted with SF900II medium to make $1 \times 10^7$ pfu/ml and 1 ml of the diluted one was applied to the column. Then the column was washed with 16 ml of PBS and to eluates from the column was separated into fractions of 4 ml each (being named fractions A–D). The column was further washed with 20 ml of PBS and the resulting eluate was named a fraction E. The substances adsorbed with the column were eluted with each 4 ml of PBS containing 200 mM of NaCl, PBS containing 300 mM of NaCl, PBS containing 400 mM of NaCl, PBS containing 700 mM of NaCl, and PBS containing 1 M of NaCl successively. Incidentally, 0.2% (final concentration) of bovine serum albumin (BSA) was added to the PBS used for the eluting operation. Each of the eluates recovered by the PBS of each NaCl concentrations was named fractions F to J. Each 2 ml of the fractions A to J was dialyzed against the SF900II medium and filtered through a filter of 0.2 $\mu$m. TC 100 medium (3 ml) and Sf9M cells having a cell density of $1.5 \times 10^5$ cells/cm$^2$ (from Dr. Deane Mosher, Wisconsin University) were added to a well having a diameter of 35 mm and each 1 ml of the above filtrate was added to each of the wells followed by incubating. As a positive control, a well to which 1 ml of SF900II medium containing $2.5 \times 10^6$ pfu was added and, as a negative control, another cell to which 1 ml of SF900II medium was added were prepared followed by subjecting to incubation as well. After 4, 7 and 11 days, the wells were checked and appearance of plaques and also viral infection from the formation of polyhedrin in the plaques were investigated as to the infection of virus. The result is given in Table 2. In the table, (+) means that virus was infected while (−) means that no infection was noted.

TABLE 2

| Fractions | After 4 days | After 7 days | After 11 days |
|---|---|---|---|
| A (washed with PBS) | − | − | + |
| B (washed with PBS) | − | − | − |
| C (washed with PBS) | − | − | − |
| D (washed with PBS) | − | − | − |
| E (washed with PBS) | − | − | − |
| F (200 mM NaCl) | − | − | − |
| G (300 mM NaCl) | − | − | + |
| H (400 mM NaCl) | − | − | + |
| I (700 mM NaCl) | − | + | + |
| J (1M NaCl) | − | + | + |
| Positive Control | + | + | + |
| Negative Control | − | − | − |

As shown in Table 2, infection of virus was noted only in the wells of the fractions I and J after 7 days from the incubation but, after 11 days, infection was noted in the wells of the fractions A and G to J. From this result, it is clear that baculovirus is adsorbed with FF-Cellulofine and that most of baculovirus adsorbed with the column is eluted with the PBS containing 700 mM or higher concentrations of NaCl.

As fully illustrated hereinabove, purification or removal of virus can be conducted efficiently according to the present invention and its utilization in various fields is quite useful.

In accordance with the present invention, it is now possible to purify and concentrate the virus in a sample without inactivation and the present invention is useful in the manufacture of physiologically active substances derived from virus such as vaccine and reverse transcriptase and also in the research of viruses.

It is also possible to remove the contaminated virus without deteriorating the effective components in the sample and the present invention is particularly useful in the manufacture of pharmaceuticals such as virus-free blood preparations.

It is further possible to concentrate the virus easily and the present invention is quite useful in the field of diagnosis such as detection of viruses.

It is furthermore possible to highly remove the virus in air by the use of the virus-adsorbing carrier of the present invention and the present invention is particularly useful in prevention of influenza virus and in preparation of clean air.

| | |
|---|---|
| SEQ ID NO: | 1 |
| Length: | 10 |
| Type: | nucleic acid |
| Strandedness: | double |
| Topology: | linear |
| Molecule Type: | other nucleic acid (synthetic DNA) |
| Sequence Description: | |
| CATGTCTAGA | 10 |
| SEQ ID NO: | 2 |
| Length: | 7 |
| Type: | nucleic acid |
| Strandedness: | single |
| Topology: | linear |

-continued

| | |
|---|---|
| Molecule Type: | other nucleic acid (synthetic DNA) |
| Sequence Description: | |
| GTCTAGA | 7 |
| SEQ ID NO: | 3 |
| Length: | 7 |
| Type: | nucleic acid |
| Strandedness: | single |
| Topology: | linear |
| Molecule Type: | other nucleic acid (synthetic DNA) |
| Sequence Description: | |
| GACTCTA | 7 |

What is claimed is:

1. A method for purifying a virus comprising absorbing the virus from a virus-containing sample with sulfated-fucose-containing polysaccharide(s) from *Kjellmaniae crassifolia*.

2. A method for removing a virus comprising absorbing the virus from a virus-containing sample with sulfated-fucose-containing polysaccharide(s) from *Kjellmaniae crassifolia*.

3. The method as set forth in claim 1 or 2, wherein said sulfated-fucose-containing polysaccharide(s) is/are (1) substantially free from uronic acid and (2) cannot substantially be degraded by a fucoidanase produced by Flavobacterium sp. SA-0082 (FERM BP-5402).

4. The method as set forth in claim 1 or 2, wherein said virus is a retrovirus, adenovirus, adeno-associated virus, baculovirus, influenza virus or herpes virus.

5. The method as set forth in claim 1 or 2, wherein said virus-containing sample is a liquid or a gas.

6. The method as set forth in claim 1 or 2, wherein said sulfated-fucose-containing polysaccharide(s) is/are immobilized on a carrier.

7. The method as set forth in claim 6, wherein said carrier is in the form of a gel or particles.

8. The method as set forth in claim 6, wherein said carrier is in the form of a thin film.

9. The method as set forth in claim 6, wherein said carrier is in the form of a hollow fiber.

10. A composition for absorbing a virus comprising sulfated-fucose-containing polysaccharide(s) from *Kjellmaniae crassifolia*.

11. The composition as set forth in claim 10, wherein said sulfated-fucose-containing polysaccharide(s) is/are immobilized on a carrier.

12. The composition as set forth in claim 10 or 11, wherein said sulfated-fucose-containing polysaccharide(s) is/are (1) substantially free from uronic acid and (2) cannot substantially be degraded by a fucoidanase produced by Flavobacterium sp. SA-0082 (FERM BP-5402).

13. The composition as set forth in claim 11, wherein said carrier is in the form of a gel or particles.

14. The composition as set forth in claim 11, wherein said carrier is in the form of a thin film.

15. The composition as set forth in claim 11, wherein said carrier is in the form of a hollow fiber.

* * * * *